(12) United States Patent
Marsic et al.

(10) Patent No.: US 11,091,777 B2
(45) Date of Patent: Aug. 17, 2021

(54) SYNTHETIC COMBINATORIAL AAV CAPSID LIBRARY FOR TARGETED GENE THERAPY

(71) Applicant: University of Florida Research Foundation, Incorporated, Gainesville, FL (US)

(72) Inventors: Damien Marsic, Rockville, MD (US); Sergei Zolotukhin, Gainesville, FL (US); Mavis Agbandje-McKenna, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 78 days.

(21) Appl. No.: 16/208,127

(22) Filed: Dec. 3, 2018

(65) Prior Publication Data
US 2019/0249195 A1  Aug. 15, 2019

Related U.S. Application Data

(63) Continuation of application No. 15/024,431, filed as application No. PCT/US2014/057842 on Sep. 26, 2014, now abandoned.

(60) Provisional application No. 61/883,063, filed on Sep. 26, 2013.

(51) Int. Cl.
| | |
|---|---|
| *C12N 15/86* | (2006.01) |
| *C07K 14/005* | (2006.01) |
| *C12N 7/00* | (2006.01) |
| *A61K 48/00* | (2006.01) |

(52) U.S. Cl.
CPC ............ *C12N 15/86* (2013.01); *C07K 14/005* (2013.01); *C12N 7/00* (2013.01); *A61K 48/00* (2013.01); *C12N 2750/14122* (2013.01); *C12N 2750/14143* (2013.01); *C12N 2750/14145* (2013.01)

(58) Field of Classification Search
None
See application file for complete search history.

(56) References Cited

U.S. PATENT DOCUMENTS

| | | | |
|---|---|---|---|
| 6,156,303 A | 12/2000 | Russell et al. | |
| 7,186,552 B2 | 3/2007 | Wilson et al. | |
| 7,220,577 B2 | 5/2007 | Zolotukhin | |
| 7,927,585 B2 | 4/2011 | Snyder | |
| 8,445,267 B2 | 5/2013 | Zhong et al. | |
| 9,157,098 B2 | 10/2015 | Zhong et al. | |
| 9,677,088 B2 | 6/2017 | Nakai et al. | |
| 9,725,485 B2 | 8/2017 | Srivastava et al. | |
| 10,011,640 B2 | 7/2018 | Srivastava et al. | |
| 10,308,957 B2 | 6/2019 | Boye et al. | |
| 10,426,844 B2 | 10/2019 | Agbandje-McKenna et al. | |
| 10,648,000 B2 | 5/2020 | Hauswirth et al. | |
| 10,723,768 B2 | 7/2020 | Zhong et al. | |
| 10,793,606 B2 | 10/2020 | Zolotukhin et al. | |
| 10,815,279 B2 | 10/2020 | Srivastava et al. | |
| 2006/0188484 A1 | 8/2006 | Rabinowitz et al. | |
| 2007/0036760 A1 | 2/2007 | Wilson et al. | |
| 2008/0269149 A1* | 10/2008 | Bowles ................... | A61P 25/08 514/44 R |
| 2009/0075357 A1 | 3/2009 | Snyder | |
| 2009/0197338 A1 | 8/2009 | Vandenberghe et al. | |
| 2013/0109742 A1 | 5/2013 | Hewitt et al. | |
| 2014/0341852 A1 | 11/2014 | Srivastava et al. | |
| 2016/0017005 A1 | 1/2016 | Asokan et al. | |
| 2016/0369298 A1 | 3/2016 | Marsic et al. | |
| 2016/0289275 A1 | 10/2016 | Chiorini et al. | |
| 2018/0066285 A1 | 3/2018 | Ojala et al. | |
| 2018/0193489 A1 | 7/2018 | Hobbs et al. | |
| 2018/0244727 A1 | 8/2018 | Zhong et al. | |
| 2018/0245098 A1 | 8/2018 | Yazicioglu et al. | |
| 2019/0048041 A1 | 2/2019 | Asokan et al. | |
| 2019/0127424 A1 | 5/2019 | Srivastava et al. | |
| 2020/0002386 A1 | 1/2020 | Zolotukhin et al. | |
| 2020/0181644 A1 | 6/2020 | Zolotukhin et al. | |

(Continued)

FOREIGN PATENT DOCUMENTS

| | | |
|---|---|---|
| EP | 1 487 501 B1 | 12/2012 |
| JP | 2008-523813 A | 7/2008 |
| WO | WO 2004/112727 A2 | 12/2004 |

(Continued)

OTHER PUBLICATIONS

Wu et al., Mutational Analysis of the Adeno-Associated Virus Type 2 (AAV2) Capsid Gene and Construction of AAV2 Vectors with Altered Tropism. Journal of Virology, Sep. 2000, p. 8635-8647, vol. 74, No. 18. (Year: 2000).*
Xie et al., The atomic structure of adeno-associated virus (AAV-2), a vector for human gene therapy. PNAS, 2002, 99:10405-10410 (Year: 2002).*
GenBank AAS99272.1, capsid protein VP1 (Adeno-associated virus). Deposited Jan. 20, 2004, p. 1-2 (Year: 2004).*
International Search Report and Written Opinion for Application No. PCT/US2014/057842 dated Jan. 26, 2015.
International Preliminary Report on Patentability for Application No. PCT/US2014/057842 dated Apr. 7, 2016.
Partial Supplementary European Search Report for Application No. EP 14848603.8 dated Apr. 12, 2017.

(Continued)

*Primary Examiner* — Arthur S Leonard
(74) *Attorney, Agent, or Firm* — Wolf, Greenfield & Sacks, P.C.

(57) ABSTRACT

Disclosed are compositions and methods for producing modified adeno-associated virus (AAV) cap genes and combinatorial libraries of chimeric AAV vectors and virions; selecting for virions displaying cell-specific tropisms; and, in certain embodiments, producing helper vectors containing one or more modified AAV cap genes. The synthetic combinatorial AAV capsid libraries of the invention are useful in introducing into selected target host cells one or more nucleic acid molecules. The viral vectors and genetic constructs disclosed herein are also useful in a variety of diagnostic and/or therapeutic gene-therapy regimens.

23 Claims, 16 Drawing Sheets

Specification includes a Sequence Listing.

(56) References Cited

U.S. PATENT DOCUMENTS

2021/0061863 A1    3/2021    Zolotukhin et al.

FOREIGN PATENT DOCUMENTS

| | | |
|---|---|---|
| WO | WO 2005/033321 A2 | 4/2005 |
| WO | WO 2008/124724 A1 | 10/2008 |
| WO | WO 2010/011404 A2 | 1/2010 |
| WO | WO 2012/057363 A1 | 5/2012 |
| WO | WO 2012/109570 A1 | 8/2012 |
| WO | WO 2013/170078 A1 | 11/2013 |
| WO | WO 2014/193716 A2 | 12/2014 |
| WO | WO 2015/048534 A1 | 4/2015 |
| WO | WO 2015/108610 A1 | 7/2015 |
| WO | WO 2015/121501 A1 | 8/2015 |
| WO | WO 2015/134643 A1 | 9/2015 |
| WO | WO 2017/070476 A2 | 4/2017 |

OTHER PUBLICATIONS

Supplementary European Search Report for European Application No. 14 848 603.8 dated Jul. 19, 2017.
Appleyard et al., Pretreatment with the probiotic VSL#3 delays transition from inflammation to dysplasia in a rat model of colitis-associated cancer. Am J Physiol Gastrointest Liver Physiol. Dec. 2011;301(6):G1004-13. doi: 10.1152/ajpgi.00167.2011. Epub Sep. 8, 2011.
Bowles et al., Phase 1 gene therapy for Duchenne muscular dystrophy using a translational optimized AAV vector. Mol Ther. Feb. 2012;20(2):443-55. doi: 10.1038/mt.2011.237. Epub Nov. 8, 2011.
Bozzetti et al., Metabolic Bone Disease in preterm newborn: an update on nutritional issues. Ital J Pediatr. Jul. 14, 2009;35(1):20. doi: 10.1186/1824-7288-35-20.
Galindo, Alkaline Phophatase (ALP). Aug 23, 2010. Retrieved from the Internet. <URL:http://www.isu.edu/~galisusa/alp_sop.html>. 4 pages.
Gao et al., Clades of Adeno-associated viruses are widely disseminated in human tissues. J Virol. Jun. 2004;78(12):6381-8. Novel adeno-associated viruses from rhesus monkeys as vectors for human gene therapy. Proc Natl Acad Sci U S A. Sep. 3, 2002;99(18):11854-9. Epub Aug. 21, 2002.
Lan et al., IA-2, a transmembrane protein of the protein tyrosine phosphatase family, is a major autoantigen in insulin-dependent diabetes mellitus. Proc Natl Acad Sci U S A. Jun. 25, 1996;93(13):6367-70.
Lerch et al., The structure of adeno-associated virus serotype 3B (AAV-3B): insights into receptor binding and immune evasion. Virology. Jul. 20, 2010;403(1):26-36. doi: 10.1016/j.virol.2010.03.027. Epub May 4, 2010.
Lochrie et al., Mutations on the external surfaces of adeno-associated virus type 2 capsids that affect transduction and neutralization. J Virol. Jan. 2006;80(2):821-34.
Marsic et al., Vector design Tour de Force: integrating combinatorial and rational approaches to derive novel adeno-associated virus variants. Mol Ther. Nov. 2014;22(11):1900-9. doi: 10.1038/mt.2014.139. Epub Jul. 22, 2014.
Muramatsu et al., Nucleotide sequencing and generation of an infectious clone of adeno-associated virus 3. Virology. Jul. 1, 1996;221(1):208-17.
Opie et al., Identification of amino acid residues in the capsid proteins of adeno-associated virus type 2 that contribute to heparan sulfate proteoglycan binding. J Virol. Jun. 2003;77(12):6995-7006.
Ozawa, [Gene therapy using AAV]. Uirusu. Jun. 2007;57(1):47-55. Article in Japanese.
Perabo et al., Combinatorial engineering of a gene therapy vector: directed evolution of adeno-associated virus. J Gene Med. Feb. 2006;8(2):155-62.
Talbot et al., Serum phosphatase as an aid in the diagnosis of cretinism and juvenile hypothyroidism. Am J Dis Child. 1941;62(2):273-278. doi:10.1001/archpedi.1941.02000140044003.
Zhong et al., Next generation of adeno-associated virus 2 vectors: points mutations in tyrosines lead to high-efficiency transduction at lower doses. Proc Natl Acad Sci U S A. Jun. 3, 2008;105(22):7827-32. doi: 10.1073/pnas.0802866105. Ebup May 29, 2008. Erratum in Proc Natl Acad Sci U S A. Aug. 5, 2008;105(31):11032.
Partial European Search Report dated Mar. 2, 2020 in connection with Application No. EP 19207549.7.
Extended European Search Report dated Jun. 25, 2020 in connection with Application No. EP 19207549.7.
Aslanidi et al., Optimization of the capsid of recombinant adeno-associated virus 2 (AAV2) vectors: the final threshold? PLoS One. 2013;8(3):e59142. doi: 10.1371/journal.pone.0059142. Epub Mar. 19, 2013.
Choudhury et al., Novel Methodology for Creating Macaque Retinas with Sortable Photoreceptors and Ganglion Cells. Front Neurosci. Dec. 1, 2016;10:551. eCollection 2016.
Grimm et al., E Pluribus Unum: 50 Years of Research, Millions of Viruses, and One Goal—Tailored Acceleration of AAV Evolution. Mol Ther. Dec. 2015;23(12):1819-31.
Guo et al., Protein tolerance to random amino acid change. PNAS. Jun. 22, 2004;101(25):9205-10.
Gurda et al., Capsid antibodies to different adeno-associated virus serotypes bind common regions. J Virol. Aug. 2013;87(16):9111-24. doi: 10.1128/JVI.00622-13. Epub Jun. 12, 2013.
Klimczak, Molecular evolution of adeno-associated virus for improved retinal gene therapies. University of California, Berkeley. Jan. 1, 2010. Retrieved from the internet <https://digitalassets.lib.berkeley.edu/etd/ucb/text/Klimczak_berkeley_0028E_10444.pdf> 116 pages.
Koerber et al., DNA shuffling of adeno-associated virus yields functionally diverse viral progeny. Mol Ther. Oct. 2008;16(10):1703-9. doi: 10.1038/mt.2008.167. Epub Aug. 26, 2008.
Maersch et al., Optimization of stealth adeno-associated virus vectors by randomization of immunogenic epitopes. Virology. Feb. 5, 2010;397(1):167-75. doi: 10.1016/j.virol.2009.10.021. Epub Nov. 18, 2009.
Maheshri et al., Directed evolution of adeno-associated virus yields enhanced gene delivery vectors. Nat Biotechnol. Feb. 2006;24(2):198-204. doi: 10.1038/nbt1182. Epub Jan. 22, 2006.
Pang et al., AAV-mediated cone rescue in a naturally occurring mouse model of CNGA3-achromatopsia. PLoS One. 2012;7(4):e35250. doi: 10.1371/journal.pone.0035250. Epub Apr. 11, 2012.
Romero et al., Exploring protein fitness landscapes by directed evolution. Nat Rev Mol Cell Biol. Dec. 2009;10(12):866-76.
Shannon et al., ID of Optimal Gene Delivery Vectors in Primate Retina for Treatment of Human Disorders: Labels Non-Human Primate Eyes with Fluorescent Proteins and/or Fluorescent Dyes, Creating Sortable Cell Populations, Allowing for Screening of Capsid and Promoter Libraries. Office of Technology Licensing, University of Florida. Feb. 11, 2017. Retrieved from the Internet: <http://technologylicensing.research.ufl.edu/technologies/16134.pdf> on Apr. 12, 2017. 4 pages.
Tseng et al., Mapping the AAV Capsid Host Antibody Response toward the Development of Second Generation Gene Delivery Vectors. Front Immunol. Jan. 30, 2014;5:9. doi: 10.3389/fimmu.2014.00009. eCollection 2014.
U.S. Appl. No. 17/009,536, filed Sep. 1, 2020, Zolotukhin et al.
EP 19207549.7, Mar. 2, 2020, Partial European Search Report.
EP 19207549.7, Jun. 25, 2020, Extended European Search Report.
Aslanidi et al., High-efficiency transduction of human monocyte-derived dendritic cells by capsid-modified recombinant AAV2 vectors. Vaccine. Jun. 6, 2012;30(26):3908-17. doi: 10.1016/j.vaccine.2012.03.079. Epub Apr. 10, 2012.
Maguire et al., Directed evolution of adeno-associated virus for glioma cell transduction. J Neurooncol. Feb. 2010;96(3):337-47. doi: 10.1007/s11060-009-9972-7. Epub Jul. 19, 2009.
Zolotukhin et al., Improved Adeno-associated Viral Gene Transfer to Murine Glioma. J Genet Syndr Gene Ther. Apr. 29, 2013;4(133):12815. doi: 10.4172/2157-7412.

* cited by examiner

```
VR-I 263-265
        D                                              (SEQ ID NO:1)
        P                                              (SEQ ID NO:2)
        H                                              (SEQ ID NO:3)
        K                                              (SEQ ID NO:4)
        K                                              (SEQ ID NO:5)
        N                                              (SEQ ID NO:6)
        G                                              (SEQ ID NO:7)
        A                                              (SEQ ID NO:8)
        E        T                                     (SEQ ID NO:9)
        T    T   G                                     (SEQ ID NO:10)
        S    A   S    T                                (SEQ ID NO:11)
262 S   Q    S   G    A    S    N                  (SEQ ID NO:89)
    Agcvvmdcaggarscascaac                           (SEQ ID NO:97)

VR-III 381-384
        D                                              (SEQ ID NO:12)
        R    N                                         (SEQ ID NO:13)
        N    K                                         (SEQ ID NO:14)
    A   K    R                                         (SEQ ID NO:15)
    D   E    H                                         (SEQ ID NO:16)
    T   S    Q    E                                    (SEQ ID NO:17)
381 N   N    G    S    Q    A                     (SEQ ID NO:90)
    aacmcrrsmrsmaggca                              (SEQ ID NO:98)

VR-IV 450-466
                              D                V               (SEQ ID NO:18)
                   Q          E          G     D               (SEQ ID NO:19)
                   E          P          A     E               (SEQ ID NO:20)
                   R          H          P     H               (SEQ ID NO:21)
                   S     I    I          S     N               (SEQ ID NO:22)
                   R     M    K          N     S               (SEQ ID NO:23)
                   E     R    L          N     S               (SEQ ID NO:24)
              D    G     F    V    P     K     R      R        (SEQ ID NO:25)
              A    A     H    A    H     D     K      P        (SEQ ID NO:26)
              G    Q     A    S    L     M     E      G    V   (SEQ ID NO:27)
              S    T     G    H    Q     T     Q      L    S   (SEQ ID NO:28)
        F     N    T     T    L    N     T     N      G    R   (SEQ ID NO:29)
443 Y L S R T N    T     F    S    G     T     T      Q    S   R  L  Q  P  S  Q  A  G  A  (SEQ ID NO:91)
    tattacttgagcagaacaaacrtycyvsrsoggamncvhsacgwhstcavvccttvdstttttctcagsbcrgsgcg
    (SEQ ID NO:100)

VR-V 490-503
         Q                                                     (SEQ ID NO:30)
         D                                                     (SEQ ID NO:31)
         E                                                     (SEQ ID NO:32)
         P                                                     (SEQ ID NO:33)
         H                                                     (SEQ ID NO:34)
         G                                                     (SEQ ID NO:35)
         I                                                     (SEQ ID NO:36)
         M                                                     (SEQ ID NO:37)
         R                                                     (SEQ ID NO:38)
         N                                                     (SEQ ID NO:39)
         V    G    R                                           (SEQ ID NO:40)
         A    D    E                                           (SEQ ID NO:41)
    K    L    S    Q                    K              Q       (SEQ ID NO:42)
    F    T    T    G                    D              K       (SEQ ID NO:43)
    T    Q    K    N    E               N              P       (SEQ ID NO:44)
489 S   K T   S    A    D    N    N     S    E    Y    S   W  T  G  (SEQ ID NO:92)
    tcaaaamavnsrvcsrsaacaacaagtrastactcgtggmmagga
    (SEQ ID NO:101)
```

FIG. 1A

```
VR-VI 527-532
                          G
                  N       R
                  T       N
          E   S   D   K   N                           (SEQ ID NO:45)
          R   G   A   D   S                           (SEQ ID NO:46)
          G   N   K   S   K                           (SEQ ID NO:47)
    526 H K   D   D   E   K   F                       (SEQ ID NO:48)
        cacrrggacrrcmsrrsarsttt                       (SEQ ID NO:49)
                                                      (SEQ ID NO:50)
                                                      (SEQ ID NO:93)
                                                      (SEQ ID NO:99)

VR-VII 545-556
                                      F
                                      S
                                      V
                  D           D   A   G               (SEQ ID NO:51)
                  S           P   E                   (SEQ ID NO:52)
                  R           R   K                   (SEQ ID NO:53)
                  K   G       T   N                   (SEQ ID NO:54)
                  G   E   A   N   G   D               (SEQ ID NO:55)
          D   A   A   A   D   I   Y   D   H           (SEQ ID NO:56)
          S   G   T   R   S   A   A   A   S           (SEQ ID NO:57)
          E   N   T   R   T   N   D   T   E   L   T   N   (SEQ ID NO:58)
    544 K Q   G   S   E   K   T   N   V   D   I   E   K   V   (SEQ ID NO:59)
        aagsaarrcrscrvsrvarvcratrycgmsnhcrvmvragtc        (SEQ ID NO:60)
                                                          (SEQ ID NO:61)
                                                          (SEQ ID NO:94)
                                                          (SEQ ID NO:102)

VR-VIII 585-596
                      V
                      E
                      P
                      M
          E   E       M               F   G           (SEQ ID NO:62)
          P   P       M               H   E           (SEQ ID NO:63)
          H   K       S               T   I           (SEQ ID NO:64)
          T   T       R       P   N   M   S   E       (SEQ ID NO:65)
          K   K       N       S   K   Y   A   P       (SEQ ID NO:66)
          G   G       K       A   C   V       P       (SEQ ID NO:67)
          A   A   K   G       D   D   A       K       (SEQ ID NO:68)
          D   D   R   A       N   E   G       D       (SEQ ID NO:69)
          Q   Q   H   D       Y   Q   R       H       (SEQ ID NO:70)
          S   S   S   S   L   V   S   T       Q       (SEQ ID NO:71)
          N   N   Q   T       I   P   S       T       (SEQ ID NO:72)
    584 Q R   G   N   N   Q   A   A   T   A   D   V   N   T   (SEQ ID NO:73)
        cagvvsvvsmrsrvcnsgcagctdhcvvsrnsgtcvmsaca             (SEQ ID NO:74)
                                                              (SEQ ID NO:75)
                                                              (SEQ ID NO:76)
                                                              (SEQ ID NO:95)
                                                              (SEQ ID NO:103)

VR-IX 704-713
                      D
                      E
                      L
                      P
          S           H       C                       (SEQ ID NO:77)
          R       T   I       Y                       (SEQ ID NO:78)
          T       N   M       V                       (SEQ ID NO:79)
          K   E   K   K   D       R                   (SEQ ID NO:80)
          G   R   R   A   I       Q                   (SEQ ID NO:81)
          A   N   H   Q   P       V   C               (SEQ ID NO:82)
          D   D   D   P   T   G   L   L               (SEQ ID NO:83)
          F   E   Q   Q   N   S   E   W               (SEQ ID NO:84)
    703 N Y   N   K   S   V   N   V   D   F   T       (SEQ ID NO:85)
        aactwcrvsvasmvsvhsddtgtgswstksact             (SEQ ID NO:86)
                                                      (SEQ ID NO:87)
                                                      (SEQ ID NO:88)
                                                      (SEQ ID NO:96)
                                                      (SEQ ID NO:104)
```

FIG. 1B

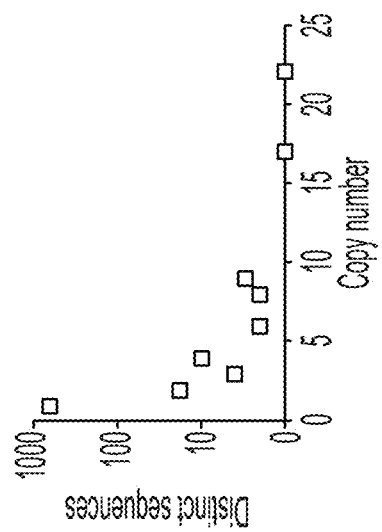
FIG. 4A
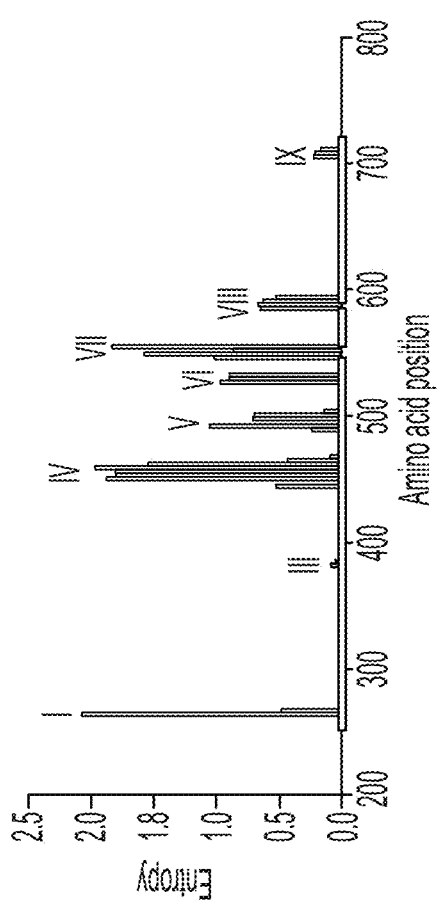
FIG. 4B
FIG. 4C
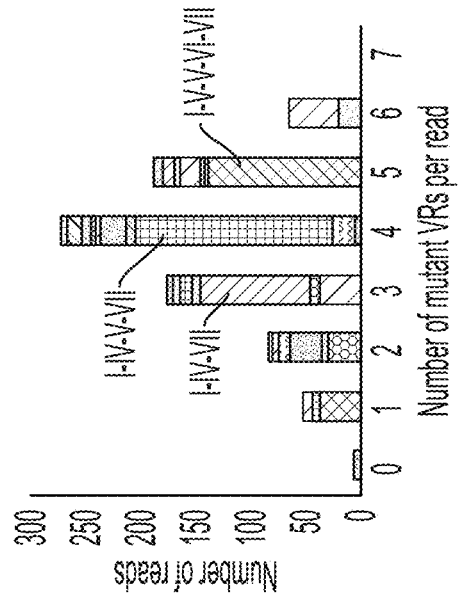
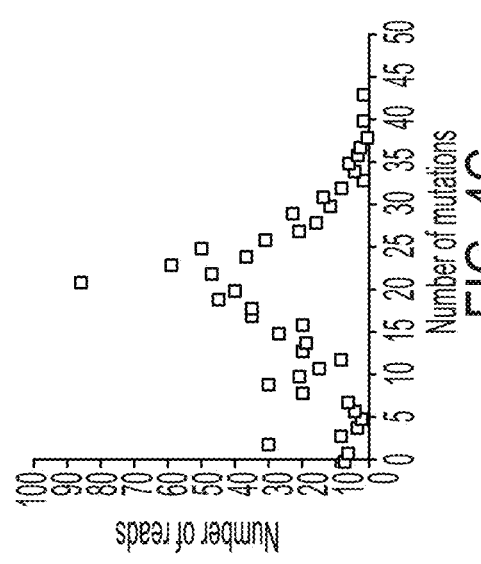
FIG. 4D

SEQ. ID NOS: 180-203

| VR | I | 444 | IV | V | Clones | Subst |
|---|---|---|---|---|---|---|
| AAV2 | SQSGASN | Y | NTPSGTTTQSRLQFS | TSADNNNSEVSWTGATKYH | | |
| Li-A | SASGASN | F | NSEGGSLTQSSLGFS | TDGENNNSDFSWTGATKYH | 24 | 14 |
| Li-B | SQSGASN | Y | NTPSGTTTQSRLQFS | TDGENNNSDFSWTGATKYH | 4 | 5 |
| Li-C | SASGASN | Y | NTPSGTTTQSRLQFS | TSADNNNSEFSWPGATYH | 3 | 4 |
| Li-D | SQSGASN | F | NSEGGSLTQSSLGFS | TDGENNNSDFSWTGATKYH | 3 | 13 |
| Li-E | SASGASN | Y | NTPSGSLTQSSLGFS | TDGENNNSDFSWTGATKYH | 2 | 10a |
| Li-F | SQSGASN | Y | NTPSGTTTQSRLQFS | TSADNNNSDFSWTGATKYM | 2 | 2 |
| Li-G | SGAGASN | F | NSEGGSLTQSSLGFS | TDGENNNSDFSWTGAYKYH | 2 | 15 |

FIG. 5A

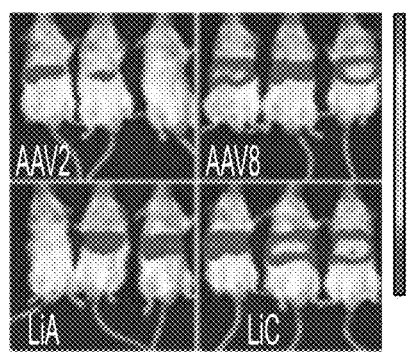

FIG. 5B

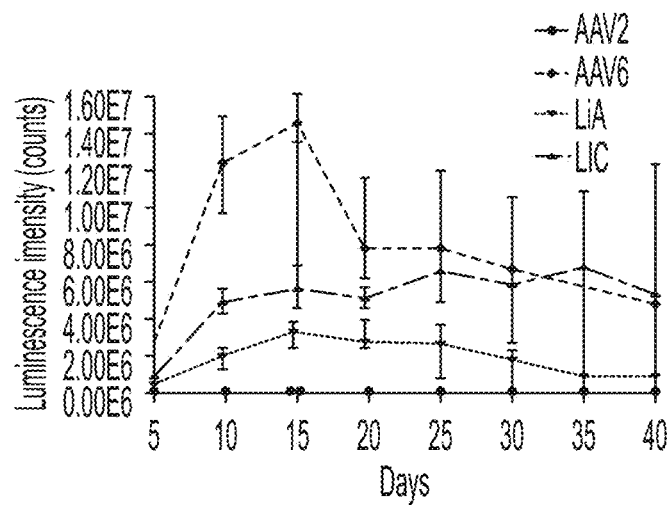

FIG. 5C

|  | VR-I<br>262-268 | VR-IV<br>443-466 | VR-V<br>489-501 | VR-VI<br>526-533 | VR-VII<br>544-557 | Mut |
|---|---|---|---|---|---|---|
| Cons | SAAGASN | YFLSRTNTESGSTTQSTLRFSQAG | SKTSADNNNSDFS | HKDDEEKF | KQGSEKTDVDIDKV | |
| 22x | STAGASN | YFLSRTNTSGIETQSTLRFSQAG | SKTDGENNNSDFS | HKDDEEKF | KQGAAADVEIDGV | 11 |
| 17x | SEAGASN | YYLSRTNTPSGTTQSRLQFSQAG | SKTSADNNNSEYS | HKDDEEKF | KQGSEKTNVDIEKV | 21 |
| 9x | SASGASN | YFLSRTNDASGSDIKSTILFSQAG | STTPSENNNSEYS | HKDDEEKF | KQGSEKTNVDIEKV | 2 |
| 9x | SAAGATN | YFLSRTNGEAGSATLSELRFSQAG | SKTSADNNNSDFS | HGDDADRF | KQGAEKSDVEVDRV | 13 |
| 9x | SDSGASN | YYLSRTNTPSGTTQSRLQFSQAG | SKTSADNNNSEYS | HKDDEEKF | KQDSGGDNTIDIDQV | 25 |
| 8x | SDAGASN | YFLSRTNTEGHDTQSTLRFSQAG | SKTSADNNNSEYS | HKDDEEKF | KEIDGGSDVAIDEV | 8 |
| 8x | SQSGASN | YYLSRTNTPSGTTQSRLQFSQAG | SKTSADNNNSEYS | HKDDEEKF | KQGSEKTNVDIEKV | 19 |
| 6x | SNAGASN | YFLSRTNTTSGIETQSTLRFSQAG | SKTDGENNNSDFS | HKDDEEKF | KQGAAADVEIDGV | 21 |
| 6x | SAAGATN | YELSRTNGEAGSATLSELRFSQPG | SKTSADNNNSDFS | HGDDADRF | KQGAEKEDVEVDRV | 26 |

SEQ ID NOS 206-255

FIG. 7

| Clone | Bar Code | Clone | Bar Code | Clone | Bar Code | Clone | Bar Code | Clone | Bar Code |
|---|---|---|---|---|---|---|---|---|---|
| BC01 | TTGTTG | BC11 | AACATC | BC21 | ACCACG | BC31 | TGACGC | BC41, 18 | ACGTTC |
| BC02 | TCCCCG | BC12 | TGGTTC | BC22 | TACTAC | BC32, 33 | ATAATG | BC42 | TGGCCG |
| BC03 | TTCCAC | BC13 | ACTCCG | BC23 | TTTTGG | BC33, 32 | ATAATG | BC43 | TTGAAC |
| BC04, 05 | AGGGAC | BC14 | ATCCCC | BC24, 19 | AGCTCC | BC34, 28 | ATGCTG | BC44 | TGGTCG |
| BC05, 04 | AGGGAC | BC15 | AACCCC | BC25 | TCCGAC | BC35 | TGGCCC | BC45 | TAATCC |
| BC06 | TCCTAG | BC16 | TAGAAG | BC26 | ACACCC | BC36 | TCTCAC | BC46 | TGCCCG |
| BC07 | AGTACC | BC17 | ATGTAC | BC27 | ACCCAC | BC37 | TCTCCC | BC47 | AGTGCC |
| BC08 | ATATGG | BC18, 41 | ACGTTC | BC28, 34 | ATGCTG | BC38 | ATCACC | BC48 | ATACCG |
| BC09 | AGCAGG | BC19, 24 | AGCTCC | BC29 | TTGGCC | BC39 | TCAGCG | BC49 | TGGGAG |
| BC10 | ACAAGC | BC20 | AGCTTC | BC30 | ACTATG | BC40 | ACAACC | BC50 | ACTGAC |

SEQ ID NOS: 256-305

FIG. 11

SEQUENCE LISTING

<160> NUMBER OF SEQ ID NOS: 274

<210> SEQ ID NO 1
<211> LENGTH: 7
<212> TYPE: PRT
<213> ORGANISM: adeno-associated virus 2

<400> SEQUENCE: 1

Ser Asp Ser Gly Ala Ser Asn
1               5

<210> SEQ ID NO 2
<211> LENGTH: 7
<212> TYPE: PRT
<213> ORGANISM: adeno-associated virus 2

<400> SEQUENCE: 2

Ser Pro Ser Gly Ala Ser Asn
1               5

<210> SEQ ID NO 3
<211> LENGTH: 7
<212> TYPE: PRT
<213> ORGANISM: adeno-associated virus 2

<400> SEQUENCE: 3

Ser His Ser Gly Ala Ser Asn
1               5

<210> SEQ ID NO 4
<211> LENGTH: 7
<212> TYPE: PRT
<213> ORGANISM: adeno-associated virus 2

<400> SEQUENCE: 4

Ser Arg Ser Gly Ala Ser Asn
1               5

<210> SEQ ID NO 5
<211> LENGTH: 7

```
<212> TYPE: PRT
<213> ORGANISM: adeno-associated virus 2

<400> SEQUENCE: 5

Ser Lys Ser Gly Ala Ser Asn
1               5

<210> SEQ ID NO 6
<211> LENGTH: 7
<212> TYPE: PRT
<213> ORGANISM: adeno-associated virus 2

<400> SEQUENCE: 6

Ser Asn Ser Gly Ala Ser Asn
1               5

<210> SEQ ID NO 7
<211> LENGTH: 7
<212> TYPE: PRT
<213> ORGANISM: adeno-associated virus 2

<400> SEQUENCE: 7

Ser Gly Ser Gly Ala Ser Asn
1               5

<210> SEQ ID NO 8
<211> LENGTH: 7
<212> TYPE: PRT
<213> ORGANISM: adeno-associated virus 2

<400> SEQUENCE: 8

Ser Ala Ser Gly Ala Ser Asn
1               5

<210> SEQ ID NO 9
<211> LENGTH: 7
<212> TYPE: PRT
<213> ORGANISM: adeno-associated virus 2

<400> SEQUENCE: 9

Ser Glu Ser Gly Thr Ser Asn
1               5

<210> SEQ ID NO 10
<211> LENGTH: 7
<212> TYPE: PRT
<213> ORGANISM: adeno-associated virus 2

<400> SEQUENCE: 10

Ser Thr Thr Gly Gly Ser Asn
1               5

<210> SEQ ID NO 11
<211> LENGTH: 7
<212> TYPE: PRT
<213> ORGANISM: adeno-associated virus 2

<400> SEQUENCE: 11

Ser Ser Ala Gly Ser Thr Asn
1               5

<210> SEQ ID NO 12
<211> LENGTH: 6
<212> TYPE: PRT
<213> ORGANISM: adeno-associated virus 2
```

```
<400> SEQUENCE: 12

Asn Asn Asp Ser Gln Ala
1               5

<210> SEQ ID NO 13
<211> LENGTH: 6
<212> TYPE: PRT
<213> ORGANISM: adeno-associated virus 2

<400> SEQUENCE: 13

Asn Asn Arg Asn Gln Ala
1               5

<210> SEQ ID NO 14
<211> LENGTH: 6
<212> TYPE: PRT
<213> ORGANISM: adeno-associated virus 2

<400> SEQUENCE: 14

Asn Asn Asn Lys Gln Ala
1               5

<210> SEQ ID NO 15
<211> LENGTH: 6
<212> TYPE: PRT
<213> ORGANISM: adeno-associated virus 2

<400> SEQUENCE: 15

Asn Ala Lys Arg Gln Ala
1               5

<210> SEQ ID NO 16
<211> LENGTH: 6
<212> TYPE: PRT
<213> ORGANISM: adeno-associated virus 2

<400> SEQUENCE: 16

Asn Asp Glu His Gln Ala
1               5

<210> SEQ ID NO 17
<211> LENGTH: 6
<212> TYPE: PRT
<213> ORGANISM: adeno-associated virus 2

<400> SEQUENCE: 17

Asn Thr Ser Gln Lys Ala
1               5

<210> SEQ ID NO 18
<211> LENGTH: 25
<212> TYPE: PRT
<213> ORGANISM: adeno-associated virus 2

<400> SEQUENCE: 18

Tyr Tyr Leu Ser Arg Thr Asn Thr Pro Ser Gly Thr Asp Thr Gln Ser
1               5                   10                  15

Arg Leu Val Phe Ser Gln Ala Gly Ala
            20                  25

<210> SEQ ID NO 19
<211> LENGTH: 25
<212> TYPE: PRT
```

```
<213> ORGANISM: adeno-associated virus 2

<400> SEQUENCE: 19

Tyr Tyr Leu Ser Arg Thr Asn Thr Asp Ser Gly Thr Glu Thr Gln Ser
1               5                   10                  15

Gly Leu Asp Phe Ser Gln Ala Gly Ala
            20                  25

<210> SEQ ID NO 20
<211> LENGTH: 25
<212> TYPE: PRT
<213> ORGANISM: adeno-associated virus 2

<400> SEQUENCE: 20

Tyr Tyr Leu Ser Arg Thr Asn Thr Glu Ser Gly Thr Pro Thr Gln Ser
1               5                   10                  15

Ala Leu Glu Phe Ser Gln Ala Gly Ala
            20                  25

<210> SEQ ID NO 21
<211> LENGTH: 25
<212> TYPE: PRT
<213> ORGANISM: adeno-associated virus 2

<400> SEQUENCE: 21

Tyr Tyr Leu Ser Arg Thr Asn Thr His Ser Gly Thr His Thr Gln Ser
1               5                   10                  15

Pro Leu His Phe Ser Gln Ala Gly Ala
            20                  25

<210> SEQ ID NO 22
<211> LENGTH: 25
<212> TYPE: PRT
<213> ORGANISM: adeno-associated virus 2

<400> SEQUENCE: 22

Tyr Tyr Leu Ser Arg Thr Asn Thr Ser Ser Gly Thr Ile Thr Ile Ser
1               5                   10                  15

His Leu Ile Phe Ser Gln Ala Gly Ala
            20                  25

<210> SEQ ID NO 23
<211> LENGTH: 25
<212> TYPE: PRT
<213> ORGANISM: adeno-associated virus 2

<400> SEQUENCE: 23

Tyr Tyr Leu Ser Arg Thr Asn Thr Arg Ser Gly Ile Met Thr Lys Ser
1               5                   10                  15

Ser Leu Met Phe Ser Gln Ala Gly Ala
            20                  25

<210> SEQ ID NO 24
<211> LENGTH: 25
<212> TYPE: PRT
<213> ORGANISM: adeno-associated virus 2

<400> SEQUENCE: 24

Tyr Tyr Leu Ser Arg Thr Asn Thr Lys Ser Gly Arg Lys Thr Leu Ser
1               5                   10                  15

Asn Leu Ser Phe Ser Gln Ala Gly Ala
            20                  25
```

<210> SEQ ID NO 25
<211> LENGTH: 25
<212> TYPE: PRT
<213> ORGANISM: adeno-associated virus 2

<400> SEQUENCE: 25

Tyr Tyr Leu Ser Arg Thr Asn Asp Gly Ser Gly Pro Val Thr Pro Ser
1               5                   10                  15

Lys Leu Arg Phe Ser Gln Arg Gly Ala
            20                  25

<210> SEQ ID NO 26
<211> LENGTH: 25
<212> TYPE: PRT
<213> ORGANISM: adeno-associated virus 2

<400> SEQUENCE: 26

Tyr Tyr Leu Ser Arg Thr Asn Ala Ala Ser Gly His Ala Thr His Ser
1               5                   10                  15

Asp Leu Lys Phe Ser Gln Pro Gly Ala
            20                  25

<210> SEQ ID NO 27
<211> LENGTH: 25
<212> TYPE: PRT
<213> ORGANISM: adeno-associated virus 2

<400> SEQUENCE: 27

Tyr Tyr Leu Ser Arg Thr Asn Gly Gln Ala Gly Ser Leu Thr Met Ser
1               5                   10                  15

Glu Leu Gly Phe Ser Gln Val Gly Ala
            20                  25

<210> SEQ ID NO 28
<211> LENGTH: 25
<212> TYPE: PRT
<213> ORGANISM: adeno-associated virus 2

<400> SEQUENCE: 28

Tyr Tyr Leu Ser Arg Thr Asn Ser Thr Gly Gly Asn Gln Thr Thr Ser
1               5                   10                  15

Gln Leu Leu Phe Ser Gln Leu Ser Ala
            20                  25

<210> SEQ ID NO 29
<211> LENGTH: 25
<212> TYPE: PRT
<213> ORGANISM: adeno-associated virus 2

<400> SEQUENCE: 29

Tyr Phe Leu Ser Arg Thr Asn Asn Asn Thr Gly Leu Asn Thr Asn Ser
1               5                   10                  15

Thr Leu Asn Phe Ser Gln Gly Arg Ala
            20                  25

<210> SEQ ID NO 30
<211> LENGTH: 16
<212> TYPE: PRT
<213> ORGANISM: adeno-associated virus 2

<400> SEQUENCE: 30

Ser Lys Thr Gly Ala Asp Asn Asn Asn Ser Glu Tyr Ser Trp Thr Gly
1               5                   10                  15

<210> SEQ ID NO 31
<211> LENGTH: 16
<212> TYPE: PRT
<213> ORGANISM: adeno-associated virus 2

<400> SEQUENCE: 31

Ser Lys Thr Asp Ala Asp Asn Asn Asn Ser Glu Tyr Ser Trp Thr Gly
1               5                   10                  15

<210> SEQ ID NO 32
<211> LENGTH: 16
<212> TYPE: PRT
<213> ORGANISM: adeno-associated virus 2

<400> SEQUENCE: 32

Ser Lys Thr Glu Ala Asp Asn Asn Asn Ser Glu Tyr Ser Trp Thr Gly
1               5                   10                  15

<210> SEQ ID NO 33
<211> LENGTH: 16
<212> TYPE: PRT
<213> ORGANISM: adeno-associated virus 2

<400> SEQUENCE: 33

Ser Lys Thr Pro Ala Asp Asn Asn Asn Ser Glu Tyr Ser Trp Thr Gly
1               5                   10                  15

<210> SEQ ID NO 34
<211> LENGTH: 16
<212> TYPE: PRT
<213> ORGANISM: adeno-associated virus 2

<400> SEQUENCE: 34

Ser Lys Thr His Ala Asp Asn Asn Asn Ser Glu Tyr Ser Trp Thr Gly
1               5                   10                  15

<210> SEQ ID NO 35
<211> LENGTH: 16
<212> TYPE: PRT
<213> ORGANISM: adeno-associated virus 2

<400> SEQUENCE: 35

Ser Lys Thr Gln Ala Asp Asn Asn Asn Ser Glu Tyr Ser Trp Thr Gly
1               5                   10                  15

<210> SEQ ID NO 36
<211> LENGTH: 16
<212> TYPE: PRT
<213> ORGANISM: adeno-associated virus 2

<400> SEQUENCE: 36

Ser Lys Thr Ile Ala Asp Asn Asn Asn Ser Glu Tyr Ser Trp Thr Gly
1               5                   10                  15

<210> SEQ ID NO 37
<211> LENGTH: 16
<212> TYPE: PRT
<213> ORGANISM: adeno-associated virus 2

<400> SEQUENCE: 37

Ser Lys Thr Met Ala Asp Asn Asn Asn Ser Glu Tyr Ser Trp Thr Gly
1               5                   10                  15

```
<210> SEQ ID NO 38
<211> LENGTH: 16
<212> TYPE: PRT
<213> ORGANISM: adeno-associated virus 2

<400> SEQUENCE: 38

Ser Lys Thr Arg Ala Asp Asn Asn Asn Ser Glu Tyr Ser Trp Thr Gly
1               5                   10                  15

<210> SEQ ID NO 39
<211> LENGTH: 16
<212> TYPE: PRT
<213> ORGANISM: adeno-associated virus 2

<400> SEQUENCE: 39

Ser Lys Thr Asn Ala Asp Asn Asn Asn Ser Glu Tyr Ser Trp Thr Gly
1               5                   10                  15

<210> SEQ ID NO 40
<211> LENGTH: 16
<212> TYPE: PRT
<213> ORGANISM: adeno-associated virus 2

<400> SEQUENCE: 40

Ser Lys Thr Val Gly Arg Asn Asn Asn Ser Glu Tyr Ser Trp Thr Gly
1               5                   10                  15

<210> SEQ ID NO 41
<211> LENGTH: 16
<212> TYPE: PRT
<213> ORGANISM: adeno-associated virus 2

<400> SEQUENCE: 41

Ser Lys Thr Ala Asp Arg Asn Asn Asn Ser Glu Tyr Ser Trp Thr Gly
1               5                   10                  15

<210> SEQ ID NO 42
<211> LENGTH: 16
<212> TYPE: PRT
<213> ORGANISM: adeno-associated virus 2

<400> SEQUENCE: 42

Ser Lys Lys Leu Ser Gln Asn Asn Asn Ser Lys Tyr Ser Trp Gln Gly
1               5                   10                  15

<210> SEQ ID NO 43
<211> LENGTH: 16
<212> TYPE: PRT
<213> ORGANISM: adeno-associated virus 2

<400> SEQUENCE: 43

Ser Lys Pro Thr Thr Gly Asn Asn Asn Ser Asp Tyr Ser Trp Pro Gly
1               5                   10                  15

<210> SEQ ID NO 44
<211> LENGTH: 16
<212> TYPE: PRT
<213> ORGANISM: adeno-associated virus 2

<400> SEQUENCE: 44

Ser Thr Gln Lys Asn Glu Asn Asn Ser Asn Tyr Ser Trp Pro Gly
1               5                   10                  15
```

```
<210> SEQ ID NO 45
<211> LENGTH: 8
<212> TYPE: PRT
<213> ORGANISM: adeno-associated virus 2

<400> SEQUENCE: 45

His Lys Asp Asp Glu Gly Lys Phe
1               5

<210> SEQ ID NO 46
<211> LENGTH: 8
<212> TYPE: PRT
<213> ORGANISM: adeno-associated virus 2

<400> SEQUENCE: 46

His Lys Asp Asp Asn Arg Lys Phe
1               5

<210> SEQ ID NO 47
<211> LENGTH: 8
<212> TYPE: PRT
<213> ORGANISM: adeno-associated virus 2

<400> SEQUENCE: 47

His Lys Asp Asp Thr Asn Lys Phe
1               5

<210> SEQ ID NO 48
<211> LENGTH: 8
<212> TYPE: PRT
<213> ORGANISM: adeno-associated virus 2

<400> SEQUENCE: 48

His Glu Asp Ser Asp Lys Asn Phe
1               5

<210> SEQ ID NO 49
<211> LENGTH: 8
<212> TYPE: PRT
<213> ORGANISM: adeno-associated virus 2

<400> SEQUENCE: 49

His Arg Asp Gly Ala Asp Ser Phe
1               5

<210> SEQ ID NO 50
<211> LENGTH: 8
<212> TYPE: PRT
<213> ORGANISM: adeno-associated virus 2

<400> SEQUENCE: 50

His Gly Asp Asn Lys Ser Arg Phe
1               5

<210> SEQ ID NO 51
<211> LENGTH: 14
<212> TYPE: PRT
<213> ORGANISM: adeno-associated virus 2

<400> SEQUENCE: 51

Lys Gln Gly Ser Glu Lys Thr Asn Val Asp Phe Glu Glu Val
1               5                   10

<210> SEQ ID NO 52
<211> LENGTH: 14
```

```
<212> TYPE: PRT
<213> ORGANISM: adeno-associated virus 2

<400> SEQUENCE: 52

Lys Gln Gly Ser Glu Lys Thr Asn Val Asp Ser Glu Glu Val
1               5                   10

<210> SEQ ID NO 53
<211> LENGTH: 14
<212> TYPE: PRT
<213> ORGANISM: adeno-associated virus 2

<400> SEQUENCE: 53

Lys Gln Gly Ser Glu Lys Thr Asn Val Asp Val Glu Glu Val
1               5                   10

<210> SEQ ID NO 54
<211> LENGTH: 14
<212> TYPE: PRT
<213> ORGANISM: adeno-associated virus 2

<400> SEQUENCE: 54

Lys Gln Gly Ser Asp Lys Thr Asn Val Asp Asp Ala Gly Val
1               5                   10

<210> SEQ ID NO 55
<211> LENGTH: 14
<212> TYPE: PRT
<213> ORGANISM: adeno-associated virus 2

<400> SEQUENCE: 55

Lys Gln Gly Ser Ser Lys Thr Asn Val Asp Pro Arg Glu Val
1               5                   10

<210> SEQ ID NO 56
<211> LENGTH: 14
<212> TYPE: PRT
<213> ORGANISM: adeno-associated virus 2

<400> SEQUENCE: 56

Lys Gln Gly Ser Arg Lys Thr Asn Val Asp His Lys Gln Val
1               5                   10

<210> SEQ ID NO 57
<211> LENGTH: 14
<212> TYPE: PRT
<213> ORGANISM: adeno-associated virus 2

<400> SEQUENCE: 57

Lys Gln Gly Ser Lys Gly Gly Asn Val Asp Thr Asn Arg Val
1               5                   10

<210> SEQ ID NO 58
<211> LENGTH: 14
<212> TYPE: PRT
<213> ORGANISM: adeno-associated virus 2

<400> SEQUENCE: 58

Lys Gln Gly Ser Gly Glu Ala Asn Val Asp Asn Gly Asp Val
1               5                   10

<210> SEQ ID NO 59
<211> LENGTH: 14
<212> TYPE: PRT
<213> ORGANISM: adeno-associated virus 2
```

<400> SEQUENCE: 59

Lys Gln Asp Ala Ala Asp Asn Ile Asp Tyr Asp His Val
1               5                   10

<210> SEQ ID NO 60
<211> LENGTH: 14
<212> TYPE: PRT
<213> ORGANISM: adeno-associated virus 2

<400> SEQUENCE: 60

Lys Gln Ser Gly Thr Arg Ser Asn Ala Ala Ser Ser Val
1               5                   10

<210> SEQ ID NO 61
<211> LENGTH: 14
<212> TYPE: PRT
<213> ORGANISM: adeno-associated virus 2

<400> SEQUENCE: 61

Lys Glu Asn Thr Asn Thr Asn Asp Thr Glu Leu Thr Asn Val
1               5                   10

<210> SEQ ID NO 62
<211> LENGTH: 14
<212> TYPE: PRT
<213> ORGANISM: adeno-associated virus 2

<400> SEQUENCE: 62

Gln Arg Gly Asn Asn Val Ala Ala Thr Ala Asp Val Asn Thr
1               5                   10

<210> SEQ ID NO 63
<211> LENGTH: 14
<212> TYPE: PRT
<213> ORGANISM: adeno-associated virus 2

<400> SEQUENCE: 63

Gln Arg Gly Asn Asn Glu Ala Ala Thr Ala Asp Val Asn Thr
1               5                   10

<210> SEQ ID NO 64
<211> LENGTH: 14
<212> TYPE: PRT
<213> ORGANISM: adeno-associated virus 2

<400> SEQUENCE: 64

Gln Arg Gly Asn Asn Pro Ala Ala Thr Ala Asp Val Asn Thr
1               5                   10

<210> SEQ ID NO 65
<211> LENGTH: 14
<212> TYPE: PRT
<213> ORGANISM: adeno-associated virus 2

<400> SEQUENCE: 65

Gln Arg Gly Asn Asn His Ala Ala Thr Ala Asp Val Asn Thr
1               5                   10

<210> SEQ ID NO 66
<211> LENGTH: 14
<212> TYPE: PRT
<213> ORGANISM: adeno-associated virus 2

<400> SEQUENCE: 66

Gln Glu Glu Asn Asn Ile Ala Ala Thr Pro Gly Val Asn Thr
1               5                   10

<210> SEQ ID NO 67
<211> LENGTH: 14
<212> TYPE: PRT
<213> ORGANISM: adeno-associated virus 2

<400> SEQUENCE: 67

Gln Pro Pro Asn Asn Met Ala Ala Thr His Glu Val Asn Thr
1               5                   10

<210> SEQ ID NO 68
<211> LENGTH: 14
<212> TYPE: PRT
<213> ORGANISM: adeno-associated virus 2

<400> SEQUENCE: 68

Gln His His Asn Asn Ser Ala Ala Thr Thr Ile Val Asn Thr
1               5                   10

<210> SEQ ID NO 69
<211> LENGTH: 14
<212> TYPE: PRT
<213> ORGANISM: adeno-associated virus 2

<400> SEQUENCE: 69

Gln Thr Thr Asn Asn Arg Ala Ala Phe Asn Met Val Glu Thr
1               5                   10

<210> SEQ ID NO 70
<211> LENGTH: 14
<212> TYPE: PRT
<213> ORGANISM: adeno-associated virus 2

<400> SEQUENCE: 70

Gln Lys Lys Asn Asn Ala Ala Ser Lys Lys Val Ala Thr
1               5                   10

<210> SEQ ID NO 71
<211> LENGTH: 14
<212> TYPE: PRT
<213> ORGANISM: adeno-associated virus 2

<400> SEQUENCE: 71

Gln Gly Gly Asn Asn Lys Ala Ala Asp Asp Ala Val Lys Thr
1               5                   10

<210> SEQ ID NO 72
<211> LENGTH: 14
<212> TYPE: PRT
<213> ORGANISM: adeno-associated virus 2

<400> SEQUENCE: 72

Gln Ala Ala Lys Gly Gly Ala Ala Asp Asp Ala Val Lys Thr
1               5                   10

<210> SEQ ID NO 73
<211> LENGTH: 14
<212> TYPE: PRT
<213> ORGANISM: adeno-associated virus 2

<400> SEQUENCE: 73

Gln Asp Asp Arg Ala Ala Ala Ala Asn Glu Ser Val Asp Thr

<210> SEQ ID NO 74
<211> LENGTH: 14
<212> TYPE: PRT
<213> ORGANISM: adeno-associated virus 2

<400> SEQUENCE: 74

Gln Gln Gln His Asp Asp Ala Ala Tyr Gln Arg Val His Thr
1               5                   10

<210> SEQ ID NO 75
<211> LENGTH: 14
<212> TYPE: PRT
<213> ORGANISM: adeno-associated virus 2

<400> SEQUENCE: 75

Gln Ser Ser Ser Ser Leu Ala Ala Val Ser Thr Val Gln Thr
1               5                   10

<210> SEQ ID NO 76
<211> LENGTH: 14
<212> TYPE: PRT
<213> ORGANISM: adeno-associated virus 2

<400> SEQUENCE: 76

Gln Asn Asn Gln Thr Thr Ala Ala Ile Arg Asn Val Thr Thr
1               5                   10

<210> SEQ ID NO 77
<211> LENGTH: 12
<212> TYPE: PRT
<213> ORGANISM: adeno-associated virus 2

<400> SEQUENCE: 77

Asn Tyr Asn Lys Lys Ser Asp Asn Val Asp Phe Thr
1               5                   10

<210> SEQ ID NO 78
<211> LENGTH: 12
<212> TYPE: PRT
<213> ORGANISM: adeno-associated virus 2

<400> SEQUENCE: 78

Asn Tyr Asn Lys Lys Ser Glu Asn Val Asp Phe Thr
1               5                   10

<210> SEQ ID NO 79
<211> LENGTH: 12
<212> TYPE: PRT
<213> ORGANISM: adeno-associated virus 2

<400> SEQUENCE: 79

Asn Tyr Asn Lys Lys Ser Leu Asn Val Asp Phe Thr
1               5                   10

<210> SEQ ID NO 80
<211> LENGTH: 12
<212> TYPE: PRT
<213> ORGANISM: adeno-associated virus 2

<400> SEQUENCE: 80

Asn Tyr Asn Lys Lys Ser Pro Asn Val Asp Phe Thr
1               5                   10

<210> SEQ ID NO 81
<211> LENGTH: 12
<212> TYPE: PRT
<213> ORGANISM: adeno-associated virus 2

<400> SEQUENCE: 81

Asn Tyr Ser Lys Lys Ser His Cys Val Asp Phe Thr
1               5                   10

<210> SEQ ID NO 82
<211> LENGTH: 11
<212> TYPE: PRT
<213> ORGANISM: adeno-associated virus 2

<400> SEQUENCE: 82

Asn Tyr Arg Lys Thr Ile Tyr Val Asp Phe Thr
1               5                   10

<210> SEQ ID NO 83
<211> LENGTH: 11
<212> TYPE: PRT
<213> ORGANISM: adeno-associated virus 2

<400> SEQUENCE: 83

Asn Tyr Lys Glu Lys Lys Asp Val His Phe Thr
1               5                   10

<210> SEQ ID NO 84
<211> LENGTH: 11
<212> TYPE: PRT
<213> ORGANISM: adeno-associated virus 2

<400> SEQUENCE: 84

Asn Tyr Gly His Arg Ala Ile Val Gln Phe Thr
1               5                   10

<210> SEQ ID NO 85
<211> LENGTH: 11
<212> TYPE: PRT
<213> ORGANISM: adeno-associated virus 2

<400> SEQUENCE: 85

Asn Tyr Ala Asn His Gln Phe Val Val Cys Thr
1               5                   10

<210> SEQ ID NO 86
<211> LENGTH: 12
<212> TYPE: PRT
<213> ORGANISM: adeno-associated virus 2

<400> SEQUENCE: 86

Asn Tyr Asp Asp Asp Pro Thr Gly Val Leu Leu Thr
1               5                   10

<210> SEQ ID NO 87
<211> LENGTH: 11
<212> TYPE: PRT
<213> ORGANISM: adeno-associated virus 2

<400> SEQUENCE: 87

Asn Tyr Asp Asp Pro Thr Gly Val Leu Leu Thr
1               5                   10

<210> SEQ ID NO 88

```
<211> LENGTH: 11
<212> TYPE: PRT
<213> ORGANISM: adeno-associated virus 2

<400> SEQUENCE: 88

Asn Phe Glu Gln Gln Asn Ser Val Glu Trp Thr
1               5                   10

<210> SEQ ID NO 89
<211> LENGTH: 7
<212> TYPE: PRT
<213> ORGANISM: adeno-associated virus 2

<400> SEQUENCE: 89

Ser Gln Ser Gly Ala Ser Asn
1               5

<210> SEQ ID NO 90
<211> LENGTH: 6
<212> TYPE: PRT
<213> ORGANISM: adeno-associated virus 2

<400> SEQUENCE: 90

Asn Asn Gly Ser Gln Ala
1               5

<210> SEQ ID NO 91
<211> LENGTH: 25
<212> TYPE: PRT
<213> ORGANISM: adeno-associated virus 2

<400> SEQUENCE: 91

Tyr Tyr Leu Ser Arg Thr Asn Thr Pro Ser Gly Thr Thr Thr Trp Ser
1               5                   10                  15

Arg Leu Gln Phe Ser Gln Ala Gly Ala
            20                  25

<210> SEQ ID NO 92
<211> LENGTH: 16
<212> TYPE: PRT
<213> ORGANISM: adeno-associated virus 2

<400> SEQUENCE: 92

Ser Lys Thr Ser Ala Asp Asn Asn Asn Ser Glu Tyr Ser Trp Thr Gly
1               5                   10                  15

<210> SEQ ID NO 93
<211> LENGTH: 8
<212> TYPE: PRT
<213> ORGANISM: adeno-associated virus 2

<400> SEQUENCE: 93

His Lys Asp Asp Glu Glu Lys Phe
1               5

<210> SEQ ID NO 94
<211> LENGTH: 14
<212> TYPE: PRT
<213> ORGANISM: adeno-associated virus 2

<400> SEQUENCE: 94

Lys Gln Gly Ser Glu Lys Thr Asn Val Asp Ile Glu Lys Val
1               5                   10
```

<210> SEQ ID NO 95
<211> LENGTH: 14
<212> TYPE: PRT
<213> ORGANISM: adeno-associated virus 2

<400> SEQUENCE: 95

Gln Arg Gly Asn Asn Gln Ala Ala Thr Ala Asp Val Asn Thr
1               5                   10

<210> SEQ ID NO 96
<211> LENGTH: 11
<212> TYPE: PRT
<213> ORGANISM: adeno-associated virus 2

<400> SEQUENCE: 96

Asn Tyr Asn Lys Ser Val Asn Val Asp Phe Thr
1               5                   10

<210> SEQ ID NO 97
<211> LENGTH: 21
<212> TYPE: DNA
<213> ORGANISM: adeno-associated virus 2

<400> SEQUENCE: 97
agcvvmdcag garscascaa c                                            21

<210> SEQ ID NO 98
<211> LENGTH: 18
<212> TYPE: DNA
<213> ORGANISM: adeno-associated virus 2

<400> SEQUENCE: 98
aacracrrsm rsmaggca                                                18

<210> SEQ ID NO 99
<211> LENGTH: 24
<212> TYPE: DNA
<213> ORGANISM: adeno-associated virus 2

<400> SEQUENCE: 99
cacrrggacr rcrmsrrsar sttt                                         24

<210> SEQ ID NO 100
<211> LENGTH: 75
<212> TYPE: DNA
<213> ORGANISM: adeno-associated virus 2
<220> FEATURE:
<221> NAME/KEY: misc_feature
<222> LOCATION: (35)..(35)
<223> OTHER INFORMATION: n is a, c, g, or t

<400> SEQUENCE: 100
tattacttga gcagaacaaa crvcvvsrsc ggamncvhsa cgmhstcavv scttvdsttt   60
tctcagsbcr gsgcg                                                   75

<210> SEQ ID NO 101
<211> LENGTH: 48
<212> TYPE: DNA
<213> ORGANISM: adeno-associated virus 2
<220> FEATURE:
<221> NAME/KEY: misc_feature
<222> LOCATION: (11)..(11)
<223> OTHER INFORMATION: n is a, c, g, or t

<400> SEQUENCE: 101
tcaamammav nsrvcsrsaa caacaacagt rasttctcgt ggmmagga                48

<210> SEQ ID NO 102
<211> LENGTH: 42
<212> TYPE: DNA
<213> ORGANISM: adeno-associated virus 2
<220> FEATURE:
<221> NAME/KEY: misc_feature
<222> LOCATION: (31)..(31)
<223> OTHER INFORMATION: n is a, c, g, or t

<400> SEQUENCE: 102
aagsaarrcr scrvsrvarv cratrycgms nhcrvmvrsg tc                      42

<210> SEQ ID NO 103
<211> LENGTH: 42
<212> TYPE: DNA
<213> ORGANISM: adeno-associated virus 2
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t

<400> SEQUENCE: 103
cagvvsvvsm rsrvcvnsgc agctdhcvvs rnsgtcvmsa ca                      42

<210> SEQ ID NO 104
<211> LENGTH: 33
<212> TYPE: DNA
<213> ORGANISM: adeno-associated virus 2

<400> SEQUENCE: 104
aactwcrvsv asmvsvhsdd tgtgswstks act                               33

<210> SEQ ID NO 105
<211> LENGTH: 735
<212> TYPE: PRT
<213> ORGANISM: adeno-associated virus 2
<220> FEATURE:
<221> NAME/KEY: misc_feature
<222> LOCATION: (1)..(735)
<223> OTHER INFORMATION: Xaa= any amino acid

<400> SEQUENCE: 105

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

```
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Xaa Xaa Gly Xaa Xaa Asn Asp Asn His Tyr
                260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
        290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Xaa Xaa Xaa
370                 375                 380
Xaa Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Phe Leu Ser Arg Thr
        435                 440                 445
Asn Xaa Xaa Xaa Gly Xaa Xaa Thr Xaa Ser Xaa Leu Xaa Phe Ser Gln
450                 455                 460
Xaa Xaa Ala Ser Asp Ile Arg Asp Gln Ser Arg Asn Trp Leu Pro Gly
465                 470                 475                 480
Pro Cys Tyr Arg Gln Gln Arg Val Ser Xaa Xaa Xaa Xaa Asn Asn
                485                 490                 495
Asn Ser Xaa Phe Ser Trp Xaa Gly Ala Thr Lys Tyr His Leu Asn Gly
            500                 505                 510
Arg Asp Ser Leu Val Asn Pro Gly Pro Ala Met Ala Ser His Xaa Asp
        515                 520                 525
Xaa Xaa Xaa Xaa Phe Phe Pro Gln Ser Gly Val Leu Ile Phe Gly Lys
530                 535                 540
```

```
Xaa Xaa Xaa Xaa Xaa Xaa Xaa Xaa Xaa Xaa Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Xaa Xaa Xaa Xaa Ala Ala Xaa
            580                 585                 590

Xaa Xaa Val Xaa Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
        610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Xaa
690                 695                 700

Xaa Xaa Xaa Xaa Val Xaa Xaa Thr Val Asp Thr Asn Gly Val Tyr
705                 710                 715                 720

Ser Glu Pro Arg Pro Ile Gly Thr Arg Phe Leu Thr Arg Asn Leu
                725                 730                 735

<210> SEQ ID NO 106
<211> LENGTH: 42
<212> TYPE: PRT
<213> ORGANISM: adeno-associated virus 2

<400> SEQUENCE: 106

Ser Gln Ser Gly Ala Ser Asn Tyr Asn Thr Pro Ser Gly Thr Thr Thr
1               5                   10                  15

Gln Ser Arg Leu Gln Phe Ser Thr Ser Ala Asp Asn Asn Ser Glu
            20                  25                  30

Tyr Ser Trp Thr Gly Ala Thr Lys Tyr His
        35                  40

<210> SEQ ID NO 107
<211> LENGTH: 42
<212> TYPE: PRT
<213> ORGANISM: adeno-associated virus 2

<400> SEQUENCE: 107

Ser Ala Ser Gly Ala Ser Asn Phe Asn Ser Glu Gly Gly Ser Leu Thr
1               5                   10                  15

Gln Ser Ser Leu Gly Phe Ser Thr Asp Gly Glu Asn Asn Ser Asp
            20                  25                  30

Phe Ser Trp Thr Gly Ala Thr Lys Tyr His
        35                  40

<210> SEQ ID NO 108
<211> LENGTH: 42
<212> TYPE: PRT
<213> ORGANISM: adeno-associated virus 2

<400> SEQUENCE: 108

Ser Gln Ser Gly Ala Ser Asn Tyr Asn Thr Pro Ser Gly Thr Thr Thr
```

```
1               5                   10                  15
Gln Ser Arg Leu Gln Phe Ser Thr Asp Gly Glu Asn Asn Ser Asp
            20                  25                  30

Phe Ser Trp Thr Gly Ala Thr Lys Tyr His
            35                  40

<210> SEQ ID NO 109
<211> LENGTH: 42
<212> TYPE: PRT
<213> ORGANISM: adeno-associated virus 2

<400> SEQUENCE: 109

Ser Ala Ser Gly Ala Ser Asn Tyr Asn Thr Pro Ser Gly Thr Thr Thr
1               5                   10                  15

Gln Ser Arg Leu Gln Phe Ser Thr Ser Ala Asp Asn Asn Asn Ser Glu
            20                  25                  30

Phe Ser Trp Pro Gly Ala Thr Thr Tyr His
            35                  40

<210> SEQ ID NO 110
<211> LENGTH: 42
<212> TYPE: PRT
<213> ORGANISM: adeno-associated virus 2

<400> SEQUENCE: 110

Ser Gln Ser Gly Ala Ser Asn Phe Asn Ser Glu Gly Gly Ser Leu Thr
1               5                   10                  15

Gln Ser Ser Leu Gly Phe Ser Thr Asp Gly Glu Asn Asn Asn Ser Asp
            20                  25                  30

Phe Ser Trp Thr Gly Ala Thr Lys Tyr His
            35                  40

<210> SEQ ID NO 111
<211> LENGTH: 42
<212> TYPE: PRT
<213> ORGANISM: adeno-associated virus 2

<400> SEQUENCE: 111

Ser Ala Ser Gly Ala Ser Asn Tyr Asn Thr Pro Ser Gly Ser Leu Thr
1               5                   10                  15

Gln Ser Ser Leu Gly Phe Ser Thr Asp Gly Glu Asn Asn Asn Ser Asp
            20                  25                  30

Phe Ser Trp Thr Gly Ala Thr Lys Tyr His
            35                  40

<210> SEQ ID NO 112
<211> LENGTH: 42
<212> TYPE: PRT
<213> ORGANISM: adeno-associated virus 2

<400> SEQUENCE: 112

Ser Gln Ser Gly Ala Ser Asn Tyr Asn Thr Pro Ser Gly Thr Thr Thr
1               5                   10                  15

Gln Ser Arg Leu Gln Phe Ser Thr Ser Ala Asp Asn Asn Asn Ser Asp
            20                  25                  30

Phe Ser Trp Thr Gly Ala Thr Lys Tyr His
            35                  40

<210> SEQ ID NO 113
<211> LENGTH: 42
```

```
<212> TYPE: PRT
<213> ORGANISM: adeno-associated virus 2

<400> SEQUENCE: 113

Ser Gly Ala Gly Ala Ser Asn Phe Asn Ser Glu Gly Gly Ser Leu Thr
1               5                   10                  15

Gln Ser Ser Leu Gly Phe Ser Thr Asp Gly Glu Asn Asn Asn Ser Asp
            20                  25                  30

Phe Ser Trp Thr Gly Ala Thr Lys Tyr His
            35                  40

<210> SEQ ID NO 114
<211> LENGTH: 31
<212> TYPE: DNA
<213> ORGANISM: Artificial Sequence
<220> FEATURE:
<223> OTHER INFORMATION: Synthetic Oligonucleotide Primer

<400> SEQUENCE: 114
cctgggccct gcccacctac aacaaccacc t                              31

<210> SEQ ID NO 115
<211> LENGTH: 60
<212> TYPE: DNA
<213> ORGANISM: Artificial Sequence
<220> FEATURE:
<223> OTHER INFORMATION: Synthetic Oligonucleotide Primer

<400> SEQUENCE: 115
ctacaaacaa atttccagcv vmdcaggars cascaacgac aatcactact ttggctacag    60

<210> SEQ ID NO 116
<211> LENGTH: 60
<212> TYPE: DNA
<213> ORGANISM: Artificial Sequence
<220> FEATURE:
<223> OTHER INFORMATION: Synthetic Oligonucleotide Primer

<400> SEQUENCE: 116 cacccttgg gggtattttg acttcaacag attccactgc cacttttcac cacgggactg     60

<210> SEQ ID NO 117
<211> LENGTH: 60
<212> TYPE: DNA
<213> ORGANISM: Artificial Sequence
<220> FEATURE:
<223> OTHER INFORMATION: Synthetic Oligonucleotide Primer

<400> SEQUENCE: 117
gcaaagactc atcaacaaca actggggatt ccgccccaag agactcaact tcaagctctt    60

<210> SEQ ID NO 118
<211> LENGTH: 60
<212> TYPE: DNA
<213> ORGANISM: Artificial Sequence
<220> FEATURE:
<223> OTHER INFORMATION: Synthetic Oligonucleotide Primer

<400> SEQUENCE: 118
taacattcaa gtcaaagagg tcacammgmr srrsrgcrhg amgacaattg ccaataacct    60

<210> SEQ ID NO 119
<211> LENGTH: 60
<212> TYPE: DNA
<213> ORGANISM: Artificial Sequence
```

<220> FEATURE:
<223> OTHER INFORMATION: Synthetic Oligonucleotide Primer

<400> SEQUENCE: 119
taccagcaca gttcaggtgt ttactgactc tgagtaccag ctcccatacg tcctcggcag    60

<210> SEQ ID NO 120
<211> LENGTH: 53
<212> TYPE: DNA
<213> ORGANISM: Artificial Sequence
<220> FEATURE:
<223> OTHER INFORMATION: Synthetic Oligonucleotide Primer

<400> SEQUENCE: 120
cgcgcatcaa ggatgcctcc caccttccc agcagacgtc ttcatgatgc cac            53

<210> SEQ ID NO 121
<211> LENGTH: 63
<212> TYPE: DNA
<213> ORGANISM: Artificial Sequence
<220> FEATURE:
<223> OTHER INFORMATION: Synthetic Oligonucleotide Primer

<400> SEQUENCE: 121
gtctccatgg tgccacagta tggatacctc accctgaacr acrrsmrsma ggcagtcgga    60
cgc                                                                  63

<210> SEQ ID NO 122
<211> LENGTH: 54
<212> TYPE: DNA
<213> ORGANISM: Artificial Sequence
<220> FEATURE:
<223> OTHER INFORMATION: Synthetic Oligonucleotide Primer

<400> SEQUENCE: 122
tcttcatttt actgcctgga gtactttcct tctcagatgc tgcgcaccgg aaac           54

<210> SEQ ID NO 123
<211> LENGTH: 52
<212> TYPE: DNA
<213> ORGANISM: Artificial Sequence
<220> FEATURE:
<223> OTHER INFORMATION: Synthetic Oligonucleotide Primer

<400> SEQUENCE: 123
aactttacct tcagctacac ttttgaggac gttcctttcc acagcagcta cg             52

<210> SEQ ID NO 124
<211> LENGTH: 55
<212> TYPE: DNA
<213> ORGANISM: Artificial Sequence
<220> FEATURE:
<223> OTHER INFORMATION: Synthetic Oligonucleotide Primer

<400> SEQUENCE: 124
ctcacagcca gagtctggac cgcctgatga atcctctcat cgaccagtac ctgta          55

<210> SEQ ID NO 125
<211> LENGTH: 80
<212> TYPE: DNA
<213> ORGANISM: Artificial Sequence
<220> FEATURE:
<223> OTHER INFORMATION: Synthetic Oligonucleotide Primer
<220> FEATURE:
<221> NAME/KEY: misc_feature
<222> LOCATION: (33)..(33)

<223> OTHER INFORMATION: N=any nucleic acid

<400> SEQUENCE: 125
tttcttgagc agaacaaacr vcvvsrscgg amncvhsacc mhstcavvsc ttvdsttttc     60
tcagsbcrgs gcgagtgaca     80

<210> SEQ ID NO 126
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 126
ttcgggacca gtctagaaac     20

<210> SEQ ID NO 127
<211> LENGTH: 38
<212> TYPE: DNA
<213> ORGANISM: Artificial Sequence
<220> FEATURE:
<223> OTHER INFORMATION: Synthetic Oligonucleotide Primer

<400> SEQUENCE: 127
cagcctagga actggcttcc tggaccctgt taccgcca     38

<210> SEQ ID NO 128
<211> LENGTH: 60
<212> TYPE: DNA
<213> ORGANISM: Artificial Sequence
<220> FEATURE:
<223> OTHER INFORMATION: Synthetic Oligonucleotide Primer
<220> FEATURE:
<221> NAME/KEY: misc_feature
<222> LOCATION: (21)..(21)
<223> OTHER INFORMATION: N=any nucleic acid

<400> SEQUENCE: 128
gcagagagtc tcaamammav nsrvcsrsaa caacaacagt rasttctcct ggmmaggagc     60

<210> SEQ ID NO 129
<211> LENGTH: 48
<212> TYPE: DNA
<213> ORGANISM: Artificial Sequence
<220> FEATURE:
<223> OTHER INFORMATION: Synthetic Oligonucleotide Primer

<400> SEQUENCE: 129
taccaagtac cacctcaatg gcagagactc tctggtgaat cccggacc     48

<210> SEQ ID NO 130
<211> LENGTH: 59
<212> TYPE: DNA
<213> ORGANISM: Artificial Sequence
<220> FEATURE:
<223> OTHER INFORMATION: Synthetic Oligonucleotide Primer

<400> SEQUENCE: 130
agctatggca agccacrrgg acrrcrmsrr sarstttttt cctcagagcg gggttctca     59

<210> SEQ ID NO 131
<211> LENGTH: 79
<212> TYPE: DNA
<213> ORGANISM: Artificial Sequence
<220> FEATURE:
<223> OTHER INFORMATION: Synthetic Oligonucleotide Primer

```
<220> FEATURE:
<221> NAME/KEY: misc_feature
<222> LOCATION: (39)..(39)
<223> OTHER INFORMATION: N=any nucleic acid

<400> SEQUENCE: 131
tctttgggaa gsaarrcrsc rvsrvarvcr atrycgmsnh crvmvrsgtg atgattacag    60
acgaagagga gatctggac                                                79

<210> SEQ ID NO 132
<211> LENGTH: 51
<212> TYPE: DNA
<213> ORGANISM: Artificial Sequence
<220> FEATURE:
<223> OTHER INFORMATION: Synthetic Oligonucleotide Primer

<400> SEQUENCE: 132
gaagaggtga tcaggacaac caatcccgtg gctacagagc agtatggttc t             51

<210> SEQ ID NO 133
<211> LENGTH: 70
<212> TYPE: DNA
<213> ORGANISM: Artificial Sequence
<220> FEATURE:
<223> OTHER INFORMATION: Synthetic Oligonucleotide Primer
<220> FEATURE:
<221> NAME/KEY: misc_feature
<222> LOCATION: (32)..(47)
<223> OTHER INFORMATION: N=any nucleic acid

<400> SEQUENCE: 133
gtctctacca acctccagvv svvsmrsrvc vnsgcagctd hcvvsrnsgt cvmsacacaa    60
ggcgttcttc                                                          70

<210> SEQ ID NO 134
<211> LENGTH: 53
<212> TYPE: DNA
<213> ORGANISM: Artificial Sequence
<220> FEATURE:
<223> OTHER INFORMATION: Synthetic Oligonucleotide Primer

<400> SEQUENCE: 134
caggcatggt ctggcaggac agagatgtgt accttcaggg acccatctgg gca           53

<210> SEQ ID NO 135
<211> LENGTH: 55
<212> TYPE: DNA
<213> ORGANISM: Artificial Sequence
<220> FEATURE:
<223> OTHER INFORMATION: Synthetic Oligonucleotide Primer

<400> SEQUENCE: 135
aagattccac acacagacgg acattttcac ccctctcccc tcatgggtgg attcg         55

<210> SEQ ID NO 136
<211> LENGTH: 52
<212> TYPE: DNA
<213> ORGANISM: Artificial Sequence
<220> FEATURE:
<223> OTHER INFORMATION: Synthetic Oligonucleotide Primer

<400> SEQUENCE: 136
gacttaaaca ccctcctcca cagattctca tcaagaacac ccccgtacgt gc            52

<210> SEQ ID NO 137
```

<211> LENGTH: 49
<212> TYPE: DNA
<213> ORGANISM: Artificial Sequence
<220> FEATURE:
<223> OTHER INFORMATION: Synthetic Oligonucleotide Primer

<400> SEQUENCE: 137
accccggtac ctgcgaatcc ttctaccacc ttcagtgcgg caaagtttg    49

<210> SEQ ID NO 138
<211> LENGTH: 45
<212> TYPE: DNA
<213> ORGANISM: Artificial Sequence
<220> FEATURE:
<223> OTHER INFORMATION: Synthetic Oligonucleotide Primer

<400> SEQUENCE: 138
cttccttcat cacacagtac tccacaggac aggtcagcgt ggaga    45

<210> SEQ ID NO 139
<211> LENGTH: 46
<212> TYPE: DNA
<213> ORGANISM: Artificial Sequence
<220> FEATURE:
<223> OTHER INFORMATION: Synthetic Oligonucleotide Primer

<400> SEQUENCE: 139
tcgagtggga gctgcagaag gaaaacagca acgctggaa tcccga    46

<210> SEQ ID NO 140
<211> LENGTH: 64
<212> TYPE: DNA
<213> ORGANISM: Artificial Sequence
<220> FEATURE:
<223> OTHER INFORMATION: Synthetic Oligonucleotide Primer

<400> SEQUENCE: 140
aattcagtac acttccaact wcrvsvasmv svhsddtgtg swstksactg tggacactaa    60
tggc    64

<210> SEQ ID NO 141
<211> LENGTH: 25
<212> TYPE: DNA
<213> ORGANISM: Artificial Sequence
<220> FEATURE:
<223> OTHER INFORMATION: Synthetic Oligonucleotide Primer

<400> SEQUENCE: 141
gtgtattcag agcctcggcc gattg    25

<210> SEQ ID NO 142
<211> LENGTH: 37
<212> TYPE: DNA
<213> ORGANISM: Artificial Sequence
<220> FEATURE:
<223> OTHER INFORMATION: Synthetic Oligonucleotide Primer

<400> SEQUENCE: 142
gctggaaatt tgtttgtaga ggtggttgtt gtaggtg    37

<210> SEQ ID NO 143
<211> LENGTH: 33
<212> TYPE: DNA
<213> ORGANISM: Artificial Sequence
<220> FEATURE:
<223> OTHER INFORMATION: Synthetic Oligonucleotide Primer

<400> SEQUENCE: 143
cccccaaggg gtgctgtagc caaagtagtg att                                    33

<210> SEQ ID NO 144
<211> LENGTH: 35
<212> TYPE: DNA
<213> ORGANISM: Artificial Sequence
<220> FEATURE:
<223> OTHER INFORMATION: Synthetic Oligonucleotide Primer

<400> SEQUENCE: 144
gttgttgatg agtctttgcc agtcccgtgg tgaaa                                  35

<210> SEQ ID NO 145
<211> LENGTH: 40
<212> TYPE: DNA
<213> ORGANISM: Artificial Sequence
<220> FEATURE:
<223> OTHER INFORMATION: Synthetic Oligonucleotide Primer

<400> SEQUENCE: 145
cctctttgac ttgaatgtta aagagcttga agttgagtct                             40

<210> SEQ ID NO 146
<211> LENGTH: 36
<212> TYPE: DNA
<213> ORGANISM: Artificial Sequence
<220> FEATURE:
<223> OTHER INFORMATION: Synthetic Oligonucleotide Primer

<400> SEQUENCE: 146
acctgaactg tgctggtaag gttattggca attgtc                                 36

<210> SEQ ID NO 147
<211> LENGTH: 30
<212> TYPE: DNA
<213> ORGANISM: Artificial Sequence
<220> FEATURE:
<223> OTHER INFORMATION: Synthetic Oligonucleotide Primer

<400> SEQUENCE: 147
atccttgatg cgcgctgccg aggacgtatg                                        30

<210> SEQ ID NO 148
<211> LENGTH: 32
<212> TYPE: DNA
<213> ORGANISM: Artificial Sequence
<220> FEATURE:
<223> OTHER INFORMATION: Synthetic Oligonucleotide Primer

<400> SEQUENCE: 148
caggcagtaa aatgaagagc gtccgactgc ct                                     32

<210> SEQ ID NO 149
<211> LENGTH: 34
<212> TYPE: DNA
<213> ORGANISM: Artificial Sequence
<220> FEATURE:
<223> OTHER INFORMATION: Synthetic Oligonucleotide Primer

<400> SEQUENCE: 149
agtgtagctg aaggtaaagt tgtttccggt gcgc                                   34

<210> SEQ ID NO 150

<211> LENGTH: 34
<212> TYPE: DNA
<213> ORGANISM: Artificial Sequence
<220> FEATURE:
<223> OTHER INFORMATION: Synthetic Oligonucleotide Primer

<400> SEQUENCE: 150
ccagactctg gctgtgagcg tagctgctgt ggaa        34

<210> SEQ ID NO 151
<211> LENGTH: 38
<212> TYPE: DNA
<213> ORGANISM: Artificial Sequence
<220> FEATURE:
<223> OTHER INFORMATION: Synthetic Oligonucleotide Primer

<400> SEQUENCE: 151
gtttgttctg ctcaagaaat acaggtactg gtcgatga        38

<210> SEQ ID NO 152
<211> LENGTH: 31
<212> TYPE: DNA
<213> ORGANISM: Artificial Sequence
<220> FEATURE:
<223> OTHER INFORMATION: Synthetic Oligonucleotide Primer

<400> SEQUENCE: 152
tctagactgg tcccgaatgt cactcgcscy g        31

<210> SEQ ID NO 153
<211> LENGTH: 34
<212> TYPE: DNA
<213> ORGANISM: Artificial Sequence
<220> FEATURE:
<223> OTHER INFORMATION: Synthetic Oligonucleotide Primer

<400> SEQUENCE: 153
tkktkttgag actctctgct ggcggtaaca gggt        34

<210> SEQ ID NO 154
<211> LENGTH: 35
<212> TYPE: DNA
<213> ORGANISM: Artificial Sequence
<220> FEATURE:
<223> OTHER INFORMATION: Synthetic Oligonucleotide Primer

<400> SEQUENCE: 154
attgaggtgg tacttggtag ctcctkkcca ggaga        35

<210> SEQ ID NO 155
<211> LENGTH: 31
<212> TYPE: DNA
<213> ORGANISM: Artificial Sequence
<220> FEATURE:
<223> OTHER INFORMATION: Synthetic Oligonucleotide Primer

<400> SEQUENCE: 155
gtggcttgcc atagctggtc cgggattcac c        31

<210> SEQ ID NO 156
<211> LENGTH: 32
<212> TYPE: DNA
<213> ORGANISM: Artificial Sequence
<220> FEATURE:
<223> OTHER INFORMATION: Synthetic Oligonucleotide Primer

<400> SEQUENCE: 156
gyyttscttc ccaaagatga gaaccccgct ct    32

<210> SEQ ID NO 157
<211> LENGTH: 38
<212> TYPE: DNA
<213> ORGANISM: Artificial Sequence
<220> FEATURE:
<223> OTHER INFORMATION: Synthetic Oligonucleotide Primer

<400> SEQUENCE: 157
ctggaggttg gtagagacag aaccatactg ctctgtag    38

<210> SEQ ID NO 158
<211> LENGTH: 31
<212> TYPE: DNA
<213> ORGANISM: Artificial Sequence
<220> FEATURE:
<223> OTHER INFORMATION: Synthetic Oligonucleotide Primer

<400> SEQUENCE: 158
gccagaccat gcctggaaga acgccttgtg t    31

<210> SEQ ID NO 159
<211> LENGTH: 33
<212> TYPE: DNA
<213> ORGANISM: Artificial Sequence
<220> FEATURE:
<223> OTHER INFORMATION: Synthetic Oligonucleotide Primer

<400> SEQUENCE: 159
cgtctgtgtg tggaatcttt gcccagatgg gtc    33

<210> SEQ ID NO 160
<211> LENGTH: 34
<212> TYPE: DNA
<213> ORGANISM: Artificial Sequence
<220> FEATURE:
<223> OTHER INFORMATION: Synthetic Oligonucleotide Primer

<400> SEQUENCE: 160
gaggagggtg tttaagtccg aatccaccca tgag    34

<210> SEQ ID NO 161
<211> LENGTH: 35
<212> TYPE: DNA
<213> ORGANISM: Artificial Sequence
<220> FEATURE:
<223> OTHER INFORMATION: Synthetic Oligonucleotide Primer

<400> SEQUENCE: 161
gtactgtgtg atgaaggaag caaactttgc cgcac    35

<210> SEQ ID NO 162
<211> LENGTH: 31
<212> TYPE: DNA
<213> ORGANISM: Artificial Sequence
<220> FEATURE:
<223> OTHER INFORMATION: Synthetic Oligonucleotide Primer

<400> SEQUENCE: 162
gcagctccca ctcgatctcc acgctgacct g    31

<210> SEQ ID NO 163
<211> LENGTH: 34
<212> TYPE: DNA

```
<213> ORGANISM: Artificial Sequence
<220> FEATURE:
<223> OTHER INFORMATION: Synthetic Oligonucleotide Primer

<400> SEQUENCE: 163
agttggaagt gtactgaatt tcgggattcc agcg                         34

<210> SEQ ID NO 164
<211> LENGTH: 36
<212> TYPE: DNA
<213> ORGANISM: Artificial Sequence
<220> FEATURE:
<223> OTHER INFORMATION: Synthetic Oligonucleotide Primer

<400> SEQUENCE: 164
ccgaggctct gaatacacgc cattagtgtc cacagt                       36

<210> SEQ ID NO 165
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 165
gcaagaccgg atgttcaaat                                         20

<210> SEQ ID NO 166
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 166
cctcaaccac gtgatccttt                                         20

<210> SEQ ID NO 167
<211> LENGTH: 27
<212> TYPE: DNA
<213> ORGANISM: Artificial Sequence
<220> FEATURE:
<223> OTHER INFORMATION: Synthetic Oligonucleotide Primer

<400> SEQUENCE: 167
caaccacctc tacaaacaaa tttccag                                 27

<210> SEQ ID NO 168
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 168
cacgccatta gtgtccacag                                         20

<210> SEQ ID NO 169
<211> LENGTH: 20
<212> TYPE: DNA
<213> ORGANISM: Artificial Sequence
<220> FEATURE:
<223> OTHER INFORMATION: Synthetic Oligonucleotide Primer

<400> SEQUENCE: 169
ggatgggcga cagagtcatc                                         20
```

<210> SEQ ID NO 170
<211> LENGTH: 26
<212> TYPE: DNA
<213> ORGANISM: Artificial Sequence
<220> FEATURE:
<223> OTHER INFORMATION: Synthetic Oligonucleotide Primer

<400> SEQUENCE: 170
caagcaatta cagattacga gtcagg                                          26

<210> SEQ ID NO 171
<211> LENGTH: 21
<212> TYPE: DNA
<213> ORGANISM: Artificial Sequence
<220> FEATURE:
<223> OTHER INFORMATION: Synthetic Oligonucleotide Primer

<400> SEQUENCE: 171
tcccatagta acgccaatag g                                               21

<210> SEQ ID NO 172
<211> LENGTH: 23
<212> TYPE: DNA
<213> ORGANISM: Artificial Sequence
<220> FEATURE:
<223> OTHER INFORMATION: Synthetic Oligonucleotide Primer

<400> SEQUENCE: 172
cttggcatat gatacacttg atg                                             23

<210> SEQ ID NO 173
<211> LENGTH: 55
<212> TYPE: DNA
<213> ORGANISM: Artificial Sequence
<220> FEATURE:
<223> OTHER INFORMATION: Synthetic Oligonucleotide Primer
<220> FEATURE:
<221> NAME/KEY: misc_feature
<222> LOCATION: (31)..(32)
<223> OTHER INFORMATION: N=any nucleic acid

<400> SEQUENCE: 173
ccatctcatc cctgcgtgtc tccgactcag nnggacgagc tgtacaagta aatcg          55

<210> SEQ ID NO 174
<211> LENGTH: 49
<212> TYPE: DNA
<213> ORGANISM: Artificial Sequence
<220> FEATURE:
<223> OTHER INFORMATION: Synthetic Oligonucleotide Primer
<220> FEATURE:
<221> NAME/KEY: misc_feature
<222> LOCATION: (24)..(25)
<223> OTHER INFORMATION: N= Any nucleotide

<400> SEQUENCE: 174
cctctctatg ggcagtcggt gatnnccatt ataagctgca ataaacaag                 49

<210> SEQ ID NO 175
<211> LENGTH: 7
<212> TYPE: PRT
<213> ORGANISM: adeno-associated virus 2

<400> SEQUENCE: 175

Ser Ala Ser Gly Ala Ser Asn
1               5

<210> SEQ ID NO 176
<211> LENGTH: 7
<212> TYPE: PRT
<213> ORGANISM: adeno-associated virus 2

<400> SEQUENCE: 176

Ser Gly Ala Gly Ala Ser Asn
1               5

<210> SEQ ID NO 177
<211> LENGTH: 15
<212> TYPE: PRT
<213> ORGANISM: adeno-associated virus 2

<400> SEQUENCE: 177

Asn Ser Glu Gly Gly Ser Leu Thr Gln Ser Ser Leu Gly Phe Ser
1               5                   10                  15

<210> SEQ ID NO 178
<211> LENGTH: 11
<212> TYPE: PRT
<213> ORGANISM: adeno-associated virus 2

<400> SEQUENCE: 178

Thr Asp Gly Glu Asn Asn Asn Ser Asp Phe Ser
1               5                   10

<210> SEQ ID NO 179
<211> LENGTH: 10
<212> TYPE: PRT
<213> ORGANISM: adeno-associated virus 2

<400> SEQUENCE: 179

Ser Glu Phe Ser Trp Pro Gly Ala Thr Thr
1               5                   10

<210> SEQ ID NO 180
<211> LENGTH: 13
<212> TYPE: PRT
<213> ORGANISM: adeno-associated virus 2

<400> SEQUENCE: 180

Thr Ser Ala Asp Asn Asn Asn Ser Asp Phe Ser Trp Thr
1               5                   10

<210> SEQ ID NO 181
<211> LENGTH: 8
<212> TYPE: PRT
<213> ORGANISM: adeno-associated virus 2

<400> SEQUENCE: 181

Ser Gln Ser Gly Ala Ser Asn Tyr
1               5

<210> SEQ ID NO 182
<211> LENGTH: 15
<212> TYPE: PRT
<213> ORGANISM: adeno-associated virus 2

<400> SEQUENCE: 182

Asn Thr Pro Ser Gly Thr Thr Thr Gln Ser Arg Leu Gln Phe Ser
1               5                   10                  15

<210> SEQ ID NO 183
<211> LENGTH: 19
<212> TYPE: PRT
<213> ORGANISM: adeno-associated virus 2

<400> SEQUENCE: 183

Thr Ser Ala Asp Asn Asn Asn Ser Glu Tyr Ser Trp Thr Gly Ala Thr
1               5                   10                  15

Lys Tyr His

<210> SEQ ID NO 184
<211> LENGTH: 8
<212> TYPE: PRT
<213> ORGANISM: adeno-associated virus 2

<400> SEQUENCE: 184

Ser Ala Ser Gly Ala Ser Asn Phe
1               5

<210> SEQ ID NO 185
<211> LENGTH: 15
<212> TYPE: PRT
<213> ORGANISM: adeno-associated virus 2

<400> SEQUENCE: 185

Asn Ser Glu Gly Gly Ser Leu Thr Gln Ser Ser Leu Gly Phe Ser
1               5                   10                  15

<210> SEQ ID NO 186
<211> LENGTH: 19
<212> TYPE: PRT
<213> ORGANISM: adeno-associated virus 2

<400> SEQUENCE: 186

Thr Asp Gly Glu Asn Asn Asn Ser Asp Phe Ser Trp Thr Gly Ala Thr
1               5                   10                  15

Lys Tyr His

<210> SEQ ID NO 187
<211> LENGTH: 8
<212> TYPE: PRT
<213> ORGANISM: adeno-associated virus 2

<400> SEQUENCE: 187

Ser Gln Ser Gly Ala Ser Asn Tyr
1               5

<210> SEQ ID NO 188
<211> LENGTH: 15
<212> TYPE: PRT
<213> ORGANISM: adeno-associated virus 2

<400> SEQUENCE: 188

Asn Thr Pro Ser Gly Thr Thr Thr Gln Ser Arg Leu Gln Phe Ser
1               5                   10                  15

<210> SEQ ID NO 189
<211> LENGTH: 19
<212> TYPE: PRT
<213> ORGANISM: adeno-associated virus 2

<400> SEQUENCE: 189

Thr Asp Gly Glu Asn Asn Asn Ser Asp Phe Ser Trp Thr Gly Ala Thr
1               5                   10                  15

Lys Tyr His

<210> SEQ ID NO 190
<211> LENGTH: 8
<212> TYPE: PRT
<213> ORGANISM: adeno-associated virus 2

<400> SEQUENCE: 190

Ser Ala Ser Gly Ala Ser Asn Tyr
1               5

<210> SEQ ID NO 191
<211> LENGTH: 15
<212> TYPE: PRT
<213> ORGANISM: adeno-associated virus 2

<400> SEQUENCE: 191

Asn Thr Pro Ser Gly Thr Thr Thr Gln Ser Arg Leu Gln Phe Ser
1               5                   10                  15

<210> SEQ ID NO 192
<211> LENGTH: 19
<212> TYPE: PRT
<213> ORGANISM: adeno-associated virus 2

<400> SEQUENCE: 192

Thr Ser Ala Asp Asn Asn Asn Ser Glu Phe Ser Trp Pro Gly Ala Thr
1               5                   10                  15

Thr Tyr His

<210> SEQ ID NO 193
<211> LENGTH: 15
<212> TYPE: PRT
<213> ORGANISM: adeno-associated virus 2

<400> SEQUENCE: 193

Asn Ser Glu Gly Gly Ser Leu Thr Gln Ser Ser Leu Gly Phe Ser
1               5                   10                  15

<210> SEQ ID NO 194
<211> LENGTH: 19
<212> TYPE: PRT
<213> ORGANISM: adeno-associated virus 2

<400> SEQUENCE: 194

Thr Asp Gly Glu Asn Asn Asn Ser Asp Phe Ser Trp Thr Gly Ala Thr
1               5                   10                  15

Lys Tyr His

<210> SEQ ID NO 195
<211> LENGTH: 8
<212> TYPE: PRT
<213> ORGANISM: adeno-associated virus 2

<400> SEQUENCE: 195

Ser Ala Ser Gly Ala Ser Asn Tyr
1               5

<210> SEQ ID NO 196
<211> LENGTH: 15
<212> TYPE: PRT
<213> ORGANISM: adeno-associated virus 2

<400> SEQUENCE: 196

Asn Thr Pro Ser Gly Ser Leu Thr Gln Ser Ser Leu Gly Phe Ser
1               5                   10                  15

<210> SEQ ID NO 197
<211> LENGTH: 19
<212> TYPE: PRT
<213> ORGANISM: adeno-associated virus 2

<400> SEQUENCE: 197

Thr Asp Gly Glu Asn Asn Ser Asp Phe Ser Trp Thr Gly Ala Thr
1               5                   10                  15

Lys Tyr His

<210> SEQ ID NO 198
<211> LENGTH: 8
<212> TYPE: PRT
<213> ORGANISM: adeno-associated virus 2

<400> SEQUENCE: 198

Ser Gln Ser Gly Ala Ser Asn Tyr
1               5

<210> SEQ ID NO 199
<211> LENGTH: 15
<212> TYPE: PRT
<213> ORGANISM: adeno-associated virus 2

<400> SEQUENCE: 199

Asn Thr Pro Ser Gly Thr Thr Thr Gln Ser Arg Leu Gln Phe Ser
1               5                   10                  15

<210> SEQ ID NO 200
<211> LENGTH: 19
<212> TYPE: PRT
<213> ORGANISM: adeno-associated virus 2

<400> SEQUENCE: 200

Thr Ser Ala Asp Asn Asn Asn Ser Asp Phe Ser Trp Thr Gly Ala Thr
1               5                   10                  15

Lys Tyr His

<210> SEQ ID NO 201
<211> LENGTH: 8
<212> TYPE: PRT
<213> ORGANISM: adeno-associated virus 2

<400> SEQUENCE: 201

Ser Gly Ala Gly Ala Ser Asn Phe
1               5

<210> SEQ ID NO 202
<211> LENGTH: 15
<212> TYPE: PRT
<213> ORGANISM: adeno-associated virus 2

<400> SEQUENCE: 202

Asn Ser Glu Gly Gly Ser Leu Thr Gln Ser Ser Leu Gly Phe Ser
1               5                   10                  15

<210> SEQ ID NO 203
<211> LENGTH: 19
<212> TYPE: PRT

<213> ORGANISM: adeno-associated virus 2

<400> SEQUENCE: 203

Thr Asp Gly Glu Asn Asn Asn Ser Asp Phe Ser Trp Thr Gly Ala Thr
1               5                   10                  15

Lys Tyr His

<210> SEQ ID NO 204
<211> LENGTH: 48
<212> TYPE: DNA
<213> ORGANISM: adeno-associated virus 2
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t

<400> SEQUENCE: 204
ctccagvvsv vsmrsrvcvn sgcagctdhc vvsrnsgtcv msacacaa          48

<210> SEQ ID NO 205
<211> LENGTH: 48
<212> TYPE: DNA
<213> ORGANISM: adeno-associated virus 2

<400> SEQUENCE: 205
ctccagagag gcaacagaca agcagctacc gcagatgtca acacacaa          48

<210> SEQ ID NO 206
<211> LENGTH: 7
<212> TYPE: PRT
<213> ORGANISM: adeno-associated virus 2

<400> SEQUENCE: 206

Ser Ala Ala Gly Ala Ser Asn
1               5

<210> SEQ ID NO 207
<211> LENGTH: 24
<212> TYPE: PRT
<213> ORGANISM: adeno-associated virus 2

<400> SEQUENCE: 207

Tyr Phe Leu Ser Arg Thr Asn Thr Glu Ser Gly Ser Thr Thr Gln Ser
1               5                   10                  15

Thr Leu Arg Phe Ser Gln Ala Gly
            20

<210> SEQ ID NO 208
<211> LENGTH: 13
<212> TYPE: PRT
<213> ORGANISM: adeno-associated virus 2

<400> SEQUENCE: 208

Ser Lys Thr Ser Ala Asp Asn Asn Asn Ser Asp Phe Ser
1               5                   10

<210> SEQ ID NO 209
<211> LENGTH: 8
<212> TYPE: PRT
<213> ORGANISM: adeno-associated virus 2

```
<400> SEQUENCE: 209

His Lys Asp Asp Glu Glu Lys Phe
1               5

<210> SEQ ID NO 210
<211> LENGTH: 14
<212> TYPE: PRT
<213> ORGANISM: adeno-associated virus 2

<400> SEQUENCE: 210

Lys Gln Gly Ser Glu Lys Thr Asp Val Asp Ile Asp Lys Val
1               5                   10

<210> SEQ ID NO 211
<211> LENGTH: 7
<212> TYPE: PRT
<213> ORGANISM: adeno-associated virus 2

<400> SEQUENCE: 211

Ser Thr Ala Gly Ala Ser Asn
1               5

<210> SEQ ID NO 212
<211> LENGTH: 24
<212> TYPE: PRT
<213> ORGANISM: adeno-associated virus 2

<400> SEQUENCE: 212

Tyr Phe Leu Ser Arg Thr Asn Thr Thr Ser Gly Ile Glu Thr Gln Ser
1               5                   10                  15

Thr Leu Arg Phe Ser Gln Ala Gly
            20

<210> SEQ ID NO 213
<211> LENGTH: 13
<212> TYPE: PRT
<213> ORGANISM: adeno-associated virus 2

<400> SEQUENCE: 213

Ser Lys Thr Asp Gly Glu Asn Asn Asn Ser Asp Phe Ser
1               5                   10

<210> SEQ ID NO 214
<211> LENGTH: 8
<212> TYPE: PRT
<213> ORGANISM: adeno-associated virus 2

<400> SEQUENCE: 214

His Lys Asp Asp Glu Glu Lys Phe
1               5

<210> SEQ ID NO 215
<211> LENGTH: 14
<212> TYPE: PRT
<213> ORGANISM: adeno-associated virus 2

<400> SEQUENCE: 215

Lys Gln Gly Ala Ala Ala Asp Asp Val Glu Ile Asp Gly Val
1               5                   10

<210> SEQ ID NO 216
<211> LENGTH: 7
<212> TYPE: PRT
<213> ORGANISM: adeno-associated virus 2
```

<400> SEQUENCE: 216

Ser Glu Ala Gly Ala Ser Asn
1               5

<210> SEQ ID NO 217
<211> LENGTH: 24
<212> TYPE: PRT
<213> ORGANISM: adeno-associated virus 2

<400> SEQUENCE: 217

Tyr Tyr Leu Ser Arg Thr Asn Thr Pro Ser Gly Thr Thr Thr Gln Ser
1               5                   10                  15

Arg Leu Gln Phe Ser Gln Ala Gly
            20

<210> SEQ ID NO 218
<211> LENGTH: 13
<212> TYPE: PRT
<213> ORGANISM: adeno-associated virus 2

<400> SEQUENCE: 218

Ser Lys Thr Ser Ala Asp Asn Asn Asn Ser Glu Tyr Ser
1               5                   10

<210> SEQ ID NO 219
<211> LENGTH: 8
<212> TYPE: PRT
<213> ORGANISM: adeno-associated virus 2

<400> SEQUENCE: 219

His Lys Asp Asp Glu Glu Lys Phe
1               5

<210> SEQ ID NO 220
<211> LENGTH: 14
<212> TYPE: PRT
<213> ORGANISM: adeno-associated virus 2

<400> SEQUENCE: 220

Lys Gln Gly Ser Glu Lys Thr Asn Val Asp Ile Glu Lys Val
1               5                   10

<210> SEQ ID NO 221
<211> LENGTH: 7
<212> TYPE: PRT
<213> ORGANISM: adeno-associated virus 2

<400> SEQUENCE: 221

Ser Ala Ser Gly Ala Ser Asn
1               5

<210> SEQ ID NO 222
<211> LENGTH: 24
<212> TYPE: PRT
<213> ORGANISM: adeno-associated virus 2

<400> SEQUENCE: 222

Tyr Phe Leu Ser Arg Thr Asn Asp Ala Ser Gly Ser Asp Thr Lys Ser
1               5                   10                  15

Thr Leu Leu Phe Ser Gln Ala Gly
            20

```
<210> SEQ ID NO 223
<211> LENGTH: 13
<212> TYPE: PRT
<213> ORGANISM: adeno-associated virus 2

<400> SEQUENCE: 223

Ser Thr Thr Pro Ser Glu Asn Asn Asn Ser Glu Tyr Ser
1               5                   10

<210> SEQ ID NO 224
<211> LENGTH: 8
<212> TYPE: PRT
<213> ORGANISM: adeno-associated virus 2

<400> SEQUENCE: 224

His Lys Asp Asp Glu Glu Lys Phe
1               5

<210> SEQ ID NO 225
<211> LENGTH: 14
<212> TYPE: PRT
<213> ORGANISM: adeno-associated virus 2

<400> SEQUENCE: 225

Lys Gln Gly Ser Glu Lys Thr Asn Val Asp Ile Glu Lys Val
1               5                   10

<210> SEQ ID NO 226
<211> LENGTH: 7
<212> TYPE: PRT
<213> ORGANISM: adeno-associated virus 2

<400> SEQUENCE: 226

Ser Ala Ala Gly Ala Thr Asn
1               5

<210> SEQ ID NO 227
<211> LENGTH: 24
<212> TYPE: PRT
<213> ORGANISM: adeno-associated virus 2

<400> SEQUENCE: 227

Tyr Phe Leu Ser Arg Thr Asn Gly Glu Ala Gly Ser Ala Thr Leu Ser
1               5                   10                  15

Glu Leu Arg Phe Ser Gln Ala Gly
            20

<210> SEQ ID NO 228
<211> LENGTH: 13
<212> TYPE: PRT
<213> ORGANISM: adeno-associated virus 2

<400> SEQUENCE: 228

Ser Lys Thr Ser Ala Asp Asn Asn Asn Ser Asp Phe Ser
1               5                   10

<210> SEQ ID NO 229
<211> LENGTH: 8
<212> TYPE: PRT
<213> ORGANISM: adeno-associated virus 2

<400> SEQUENCE: 229

His Gly Asp Asp Ala Asp Arg Phe
1               5
```

<210> SEQ ID NO 230
<211> LENGTH: 14
<212> TYPE: PRT
<213> ORGANISM: adeno-associated virus 2

<400> SEQUENCE: 230

Lys Gln Gly Ala Glu Lys Ser Asp Val Glu Val Asp Arg Val
1               5                   10

<210> SEQ ID NO 231
<211> LENGTH: 7
<212> TYPE: PRT
<213> ORGANISM: adeno-associated virus 2

<400> SEQUENCE: 231

Ser Asp Ser Gly Ala Ser Asn
1               5

<210> SEQ ID NO 232
<211> LENGTH: 24
<212> TYPE: PRT
<213> ORGANISM: adeno-associated virus 2

<400> SEQUENCE: 232

Tyr Tyr Leu Ser Arg Thr Asn Thr Pro Ser Gly Thr Thr Thr Gln Ser
1               5                   10                  15

Arg Leu Gln Phe Ser Gln Ala Gly
            20

<210> SEQ ID NO 233
<211> LENGTH: 13
<212> TYPE: PRT
<213> ORGANISM: adeno-associated virus 2

<400> SEQUENCE: 233

Ser Lys Thr Ser Ala Asp Asn Asn Asn Ser Glu Tyr Ser
1               5                   10

<210> SEQ ID NO 234
<211> LENGTH: 8
<212> TYPE: PRT
<213> ORGANISM: adeno-associated virus 2

<400> SEQUENCE: 234

His Lys Asp Asp Glu Glu Lys Phe
1               5

<210> SEQ ID NO 235
<211> LENGTH: 14
<212> TYPE: PRT
<213> ORGANISM: adeno-associated virus 2

<400> SEQUENCE: 235

Lys Gln Asp Ser Gly Gly Asp Asn Ile Asp Ile Asp Gln Val
1               5                   10

<210> SEQ ID NO 236
<211> LENGTH: 7
<212> TYPE: PRT
<213> ORGANISM: adeno-associated virus 2

<400> SEQUENCE: 236

Ser Asp Ala Gly Ala Ser Asn
1               5

<210> SEQ ID NO 237
<211> LENGTH: 24
<212> TYPE: PRT
<213> ORGANISM: adeno-associated virus 2

<400> SEQUENCE: 237

Tyr Phe Leu Ser Arg Thr Asn Thr Glu Gly Gly His Asp Thr Gln Ser
1               5                   10                  15

Thr Leu Arg Phe Ser Gln Ala Gly
            20

<210> SEQ ID NO 238
<211> LENGTH: 13
<212> TYPE: PRT
<213> ORGANISM: adeno-associated virus 2

<400> SEQUENCE: 238

Ser Lys Thr Ser Ala Asp Asn Asn Asn Ser Glu Tyr Ser
1               5                   10

<210> SEQ ID NO 239
<211> LENGTH: 8
<212> TYPE: PRT
<213> ORGANISM: adeno-associated virus 2

<400> SEQUENCE: 239

His Lys Asp Asp Glu Glu Lys Phe
1               5

<210> SEQ ID NO 240
<211> LENGTH: 14
<212> TYPE: PRT
<213> ORGANISM: adeno-associated virus 2

<400> SEQUENCE: 240

Lys Glu Asp Gly Gly Gly Ser Asp Val Ala Ile Asp Glu Val
1               5                   10

<210> SEQ ID NO 241
<211> LENGTH: 7
<212> TYPE: PRT
<213> ORGANISM: adeno-associated virus 2

<400> SEQUENCE: 241

Ser Gln Ser Gly Ala Ser Asn
1               5

<210> SEQ ID NO 242
<211> LENGTH: 24
<212> TYPE: PRT
<213> ORGANISM: adeno-associated virus 2

<400> SEQUENCE: 242

Tyr Tyr Leu Ser Arg Thr Asn Thr Pro Ser Gly Thr Thr Thr Gln Ser
1               5                   10                  15

Arg Leu Gln Phe Ser Gln Ala Gly
            20

<210> SEQ ID NO 243
<211> LENGTH: 13
<212> TYPE: PRT
<213> ORGANISM: adeno-associated virus 2

<400> SEQUENCE: 243

Ser Lys Thr Ser Ala Asp Asn Asn Ser Glu Tyr Ser
1               5                   10

<210> SEQ ID NO 244
<211> LENGTH: 8
<212> TYPE: PRT
<213> ORGANISM: adeno-associated virus 2

<400> SEQUENCE: 244

His Lys Asp Asp Glu Glu Lys Phe
1               5

<210> SEQ ID NO 245
<211> LENGTH: 14
<212> TYPE: PRT
<213> ORGANISM: adeno-associated virus 2

<400> SEQUENCE: 245

Lys Gln Gly Ser Glu Lys Thr Asn Val Asp Ile Glu Lys Val
1               5                   10

<210> SEQ ID NO 246
<211> LENGTH: 7
<212> TYPE: PRT
<213> ORGANISM: adeno-associated virus 2

<400> SEQUENCE: 246

Ser Asn Ala Gly Ala Ser Asn
1               5

<210> SEQ ID NO 247
<211> LENGTH: 24
<212> TYPE: PRT
<213> ORGANISM: adeno-associated virus 2

<400> SEQUENCE: 247

Tyr Phe Leu Ser Arg Thr Asn Thr Thr Ser Gly Ile Glu Thr Gln Ser
1               5                   10                  15

Thr Leu Arg Phe Ser Gln Ala Gly
            20

<210> SEQ ID NO 248
<211> LENGTH: 13
<212> TYPE: PRT
<213> ORGANISM: adeno-associated virus 2

<400> SEQUENCE: 248

Ser Lys Thr Asp Gly Glu Asn Asn Asn Ser Asp Phe Ser
1               5                   10

<210> SEQ ID NO 249
<211> LENGTH: 8
<212> TYPE: PRT
<213> ORGANISM: adeno-associated virus 2

<400> SEQUENCE: 249

His Lys Asp Asp Glu Glu Lys Phe
1               5

<210> SEQ ID NO 250
<211> LENGTH: 14
<212> TYPE: PRT
<213> ORGANISM: adeno-associated virus 2

<400> SEQUENCE: 250

Lys Gln Gly Ala Ala Ala Asp Asp Val Glu Ile Asp Gly Val
1               5                   10

<210> SEQ ID NO 251
<211> LENGTH: 7
<212> TYPE: PRT
<213> ORGANISM: adeno-associated virus 2

<400> SEQUENCE: 251

Ser Ala Ala Gly Ala Thr Asn
1               5

<210> SEQ ID NO 252
<211> LENGTH: 24
<212> TYPE: PRT
<213> ORGANISM: adeno-associated virus 2

<400> SEQUENCE: 252

Tyr Phe Leu Ser Arg Thr Asn Gly Glu Ala Gly Ser Ala Thr Leu Ser
1               5                   10                  15

Glu Leu Arg Phe Ser Gln Pro Gly
            20

<210> SEQ ID NO 253
<211> LENGTH: 13
<212> TYPE: PRT
<213> ORGANISM: adeno-associated virus 2

<400> SEQUENCE: 253

Ser Lys Thr Ser Ala Asp Asn Asn Asn Ser Asp Phe Ser
1               5                   10

<210> SEQ ID NO 254
<211> LENGTH: 8
<212> TYPE: PRT
<213> ORGANISM: adeno-associated virus 2

<400> SEQUENCE: 254

His Gly Asp Asp Ala Asp Arg Phe
1               5

<210> SEQ ID NO 255
<211> LENGTH: 14
<212> TYPE: PRT
<213> ORGANISM: adeno-associated virus 2

<400> SEQUENCE: 255

Lys Gln Gly Ala Glu Lys Ser Asp Val Glu Val Asp Arg Val
1               5                   10

<210> SEQ ID NO 256
<211> LENGTH: 30
<212> TYPE: DNA
<213> ORGANISM: adeno-associated virus 2

<400> SEQUENCE: 256
ttgttgaaca tcaccacgtg acgcacgttc                                    30

<210> SEQ ID NO 257
<211> LENGTH: 30
<212> TYPE: DNA
<213> ORGANISM: adeno-associated virus 2

```
<400> SEQUENCE: 257
tccccgtggt tctactacat aatgtggccg                                       30

<210> SEQ ID NO 258
<211> LENGTH: 30
<212> TYPE: DNA
<213> ORGANISM: adeno-associated virus 2

<400> SEQUENCE: 258
ttccacactc cgttttggat aatgttgaac                                       30

<210> SEQ ID NO 259
<211> LENGTH: 30
<212> TYPE: DNA
<213> ORGANISM: adeno-associated virus 2

<400> SEQUENCE: 259
agggacatcc ccagctccat gctgtggtcg                                       30

<210> SEQ ID NO 260
<211> LENGTH: 30
<212> TYPE: DNA
<213> ORGANISM: adeno-associated virus 2

<400> SEQUENCE: 260
agggacaacc cctccgactc gccctaatcc                                       30

<210> SEQ ID NO 261
<211> LENGTH: 30
<212> TYPE: DNA
<213> ORGANISM: adeno-associated virus 2

<400> SEQUENCE: 261
tcctagtaga agacaccctc tcactgcccg                                       30

<210> SEQ ID NO 262
<211> LENGTH: 30
<212> TYPE: DNA
<213> ORGANISM: adeno-associated virus 2

<400> SEQUENCE: 262
agtaccatgt acacccactc tcccagtgcc                                       30

<210> SEQ ID NO 263
<211> LENGTH: 30
<212> TYPE: DNA
<213> ORGANISM: adeno-associated virus 2

<400> SEQUENCE: 263
atatggacgt tcatgctgat caccataccg                                       30

<210> SEQ ID NO 264
<211> LENGTH: 30
<212> TYPE: DNA
<213> ORGANISM: adeno-associated virus 2

<400> SEQUENCE: 264
agcaggagct ccttggcctc agcgtgcgag                                       30

<210> SEQ ID NO 265
<211> LENGTH: 30
<212> TYPE: DNA
```

<213> ORGANISM: adeno-associated virus 2

<400> SEQUENCE: 265
acaagcagct tcactatgac aaccactgac                               30

<210> SEQ ID NO 266
<211> LENGTH: 284
<212> TYPE: DNA
<213> ORGANISM: adeno-associated virus 2
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t

<400> SEQUENCE: 266
cagcctagga actggcttcc tggaccctgt taccgccagc agagagtctc aamammavns    60
rvcsrsaaca acaacagtra sttctcctgg mmaggagcta ccaagtacca cctcaatggc   120
agagactctc tggtgaatcc cggaccagct atggcaagcc acrrggacrr crmsrrsars   180
ttttttcctc agagcggggt tctcatcttt gggaagsaar rcrscrvsrv arvcratryc   240
gmsnhcrvmv rsgtcatgat tacagacgaa gaggagatct ggac                   284

<210> SEQ ID NO 267
<211> LENGTH: 34
<212> TYPE: DNA
<213> ORGANISM: adeno-associated virus 2

<400> SEQUENCE: 267
tgggacaatg gcggtcgtct ctcagagttk tkkt                              34

<210> SEQ ID NO 268
<211> LENGTH: 35
<212> TYPE: DNA
<213> ORGANISM: adeno-associated virus 2

<400> SEQUENCE: 268
agaggacckk tcctcgatgg ttcatggtgg agtta                             35

<210> SEQ ID NO 269
<211> LENGTH: 31
<212> TYPE: DNA
<213> ORGANISM: adeno-associated virus 2

<400> SEQUENCE: 269
ccacttaggg cctggtcgat accgttcggt g                                 31

<210> SEQ ID NO 270
<211> LENGTH: 32
<212> TYPE: DNA
<213> ORGANISM: adeno-associated virus 2

<400> SEQUENCE: 270
tctcgcccca agagtagaaa cccttcstty yg                                32

<210> SEQ ID NO 271
<211> LENGTH: 48
<212> TYPE: DNA
<213> ORGANISM: adeno-associated virus 2

<400> SEQUENCE: 271

```
ctccaggcgg ggaggggcgg ggcagctgac ggggggtcg agacacaa                    48

<210> SEQ ID NO 272
<211> LENGTH: 49
<212> TYPE: DNA
<213> ORGANISM: adeno-associated virus 2

<400> SEQUENCE: 272
ctccaggggg ggaggggcgg ggcagctgcc ggggaggtcg acacacaag                  49

<210> SEQ ID NO 273
<211> LENGTH: 48
<212> TYPE: DNA
<213> ORGANISM: adeno-associated virus 2

<400> SEQUENCE: 273
ctccaggggg ggaggggcgg ggcagctgcc ggggaggtcg acacacaa                   48

<210> SEQ ID NO 274
<211> LENGTH: 49
<212> TYPE: DNA
<213> ORGANISM: adeno-associated virus 2

<400> SEQUENCE: 274
ctccagagag gcaacagaca agcagctacc gcagatgtca acacacaag                  49
```

SYNTHETIC COMBINATORIAL AAV CAPSID LIBRARY FOR TARGETED GENE THERAPY

CROSS-REFERENCE TO RELATED APPLICATIONS

The present application is a Continuation of U.S. application Ser. No. 15/024,431, filed Mar. 24, 2016, which is a national stage filing under 35 U.S.C. 371 of International Patent Application Serial No. PCT/US2014/057842, filed Sep. 26, 2014, which claims priority to U.S. Provisional Patent Appl. No. 61/883,063, filed Sep. 26, 2013, the contents of each of which is incorporated herein by reference in its entirety.

STATEMENT REGARDING FEDERALLY SPONSORED RESEARCH OR DEVELOPMENT

This invention was made with government support under Grant Nos. HL-097088 and GM-082946 awarded by the National Institutes of Health. The government has certain rights in the invention.

NAMES OF THE PARTIES TO A JOINT RESEARCH AGREEMENT

Not Applicable.

BACKGROUND OF THE INVENTION

Field of the Invention

The present invention relates to the fields of molecular biology, medicine, and virology. More particularly, the invention relates to compositions and methods for producing modified adeno-associated virus (AAV) cap genes and combinatorial libraries of chimeric AAV vectors and virions; and in particular embodiments, for selecting for virions displaying cell-specific tropisms, and also for producing helper vectors that contain one or more modified, AAV cap genes. The synthetic combinatorial AAV capsid libraries of the invention are useful in introducing into selected target host cells one or more nucleic acid molecules. The viral vectors and genetic constructs disclosed herein are also useful in a variety of diagnostic and/or therapeutic gene-therapy regimens. In an exemplary embodiment, the invention provides novel AAV variants that transduce mouse liver nearly 200 times more efficiently than the corresponding, wild-type, unmodified AAV.

Description of Related Art

Adeno-associated virus (AAV) is a single-stranded DNA virus belonging to the Parvoviridae family (Muzyezka and Berns, 2001). AAV-derived vectors are promising tools for human gene therapy applications because of their absence of pathogenicity, low immunogenicity, episomal localization and stable transgene expression. However, significant limitations to the clinical use of AAV are its promiscuity and its susceptibility to neutralization by human antibodies (Jeune et al., 2013). Both of these limitations are determined by nature of the amino acid residues exposed at the surface of the capsid. Therefore, major efforts aiming at developing useful and effective gene therapy vectors have been devoted to obtaining and studying capsid variants (Wu et al., 2006). The first approach was to study naturally occurring AAV isolates. So far, 13 serotypes have been formally characterized and hundreds of variant isolates have been sequenced. Additional capsid variation has been investigated through the generation of mosaics (viral particles made of capsid proteins from more than one serotype) (Hauck et al., 2003; Stachler and Bartlett, 2006; Gigout et al., 2005), chimeras (capsid proteins with domains from various origins) (Shen et al., 2007), and various substitutional or insertional mutants (Wu et al., 2000). However, the most significant advances are expected to result from directed evolution approaches through the development of capsid libraries.

The various strategies to generate capsid libraries that have been developed so far all suffer from sequence bias or limited diversity. Random display peptide libraries (Govindasamy et al., 2006) are limited to an insertion at one particular capsid location. Libraries generated using error-prone PCR contain a very small fraction of gene variants encoding proteins that can fold properly and assemble into a functional capsid, due to the randomness of the mutations. DNA shuffling and staggered extension processes are more efficient because they recombine naturally-occurring parental sequences and therefore are more likely to generate actual capsid variants. However, they can only recombine blocks of DNA as opposed to single nucleotide positions, which results in sequence bias (parental polymorphisms will tend to cluster together instead of being randomly distributed).

BRIEF SUMMARY OF THE INVENTION

The present invention overcomes these and other limitations inherent in the art by providing novel capsid libraries, and methods for developing AAV variants that are capable of effectively targeting specific tissues and/or organs. Various strategies have been described to generate AAV capsid libraries, including random peptide display, error-prone PCR or DNA shuffling. The novel, gene synthesis-based approach described in the present application permits the alteration of only the amino acid residues that have side chains exposed to the capsid surface, as well as restricting diversity to naturally-occurring variants, thus improving compatibility with capsid structure and function and increasing the probability of generating useful variants.

In addition, gene synthesis allows virtual recombination between naturally-occurring sequences at the nucleotide level, producing unique combinations that cannot be obtained through other methods. A comparison of naturally-occurring AAV capsid protein sequences shows nine variable regions (commonly designated loops 1 to 9), while the rest of the capsid is highly conserved. The DNA sequence encoding one of these regions (loop 2) also encodes another protein (Assembly-Activating Protein or AAP) in a different frame, which makes it unpractical to modify, AAP being required for proper assembly of functional viral particles. Therefore, the present capsid library construction involved the introduction of variations in the other eight loops only.

The invention provides a non-naturally occurring nucleic acid comprising: (a) a first nucleotide sequence encoding at least one AAV Rep protein; and (b) a second nucleotide sequence encoding at least one AAV Cap protein, wherein the second nucleotide sequence comprises: (i) a polynucleotide encoding a portion of a Cap protein found in an AAV of a first serotype but not in an AAV of a second serotype differing from the first serotype; and (ii) a polynucleotide encoding a portion of a Cap protein found in the AAV of the second serotype, but not in the AAV of the first serotype, wherein the non-naturally occurring nucleic acid further comprises a first AAV terminal repeat and a second AAV terminal repeat, and the first and second nucleotide sequences are interposed between the first and the second AAV terminal repeats. The first and the second AAV terminal repeats are preferably from serotype 2, and the first serotype is preferably serotype 1, serotype 2, serotype 3, serotype 4, scrotype 5, serotype 6, serotype 7, serotype 8, serotype 9, serotype 10, or serotype 11.

In certain embodiments, the nucleic acid is comprised within a vector, and the AAV Rep protein is preferably from serotype 2.

In related embodiments, the nucleic acid further may further include a third nucleotide sequence that encodes at least one molecule providing one or more helper function(s) preferably from an adenovirus, a herpesvirus, or a combination thereof.

The invention also provides a vector library that includes at least a first vector and a second vector, the first vector comprising a nucleic acid comprising: (a) a first nucleotide sequence encoding at least one AAV Rep protein; and (b) a second nucleotide sequence encoding at least one AAV Cap protein, wherein the second nucleotide sequence comprises: (i) a polynucleotide encoding a portion of a Cap protein found in an AAV of a first serotype but not in an AAV of a second serotype differing from the first serotype, and ((ii) a polynucleotide encoding a portion of a Cap protein found in the AAV of the second serotype, but not in the AAV of the first serotype, wherein the nucleic acid further comprises a first AAV TR and a second AAV TR, and the first and second nucleotide sequences are interposed between the first and the second AAV TRs, and the second vector differing from the first vector by at least one nucleotide.

In exemplary embodiments, the vector libraries of the present invention may be incorporated into at least one host cell, such as a mammalian or insect host cell.

The invention further provides an AAV virion that includes a nucleic acid comprising: (a) a first nucleotide sequence encoding at least one AAV Rep protein; (b) a second nucleotide sequence encoding at least one AAV Cap protein, wherein the second nucleotide sequence comprises (i) a polynucleotide encoding a portion of a Cap protein found in an AAV of a first serotype but not in an AAV of a second serotype differing from the first serotype, and (ii) a polynucleotide encoding a portion of a Cap protein found in the AAV of the second serotype, but not in the AAV of the first serotype; and (c) a first and a second AAV TR, wherein the first and the second nucleotide sequences are interposed between the first and the second AAV TRs.

In particular embodiments, the AAV virion will further preferably include at least one AAV Cap protein encoded by the second nucleotide sequence, and in certain applications, the Cap protein is preferably a wild-type AAV Cap protein.

The second nucleotide sequence may further optionally include a polynucleotide that encodes a portion of a Cap protein found in an AAV of a fourth serotype but not found in a Cap protein of an AAV of the first, second or third serotypes, and may further still include a polynucleotide that encodes a portion of a Cap protein found in an AAV of a fifth serotype but not found in a Cap protein of an AAV of the first, second, third or fourth serotypes.

In further embodiments, the AAV virions of the invention will include a second nucleotide sequence that further includes a polynucleotide that encodes a portion of a Cap protein found in an AAV of a sixth serotype but not found in a Cap protein of an AAV of the first, second, third, fourth or fifth serotypes.

Likewise, the AAV virions of the invention may include a second nucleotide sequence that further includes a polynucleotide that encodes a portion of a Cap protein found in an AAV of a seventh serotype but not found in a Cap protein of an AAV of the first, second, third, fourth, fifth or sixth serotypes, or similarly, include a polynucleotide that encodes a portion of a Cap protein found in an AAV of an eight serotype but not found in a Cap protein of an AAV of the first, second, third, fourth, fifth, sixth or seventh serotypes.

In various gene therapy applications of the disclosed invention, the nucleic acid contained within the AAV vector will preferably further include a DNA sequence that encodes one or more diagnostic, therapeutic, and/or prophylactic molecules. In such embodiments, the nucleic acid preferably further includes one or more expression control sequence(s) that effect cell- or tissue-specific expression of the therapeutic molecule. In certain embodiments, the expression control sequence includes one or more promoters operably linked to the sequence encoding the therapeutic molecule, which is preferably a polypeptide, a peptide, or an RNA.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The application contains at least one drawing that is executed in color. Copies of this patent or patent application publication with color drawing(s) will be provided by the Patent and Trademark Office upon request and payment of the necessary fee. The invention may be better understood by reference to the following description taken in conjunction with the accompanying drawings, in which like reference numerals identify like elements, and in which:

FIG. 1A and FIG. 1B show the nucleotide sequence of CapLib variable regions (VRs) and corresponding amino acid diversity. Each VR region shows a nucleotide sequence (lowercase letters) as designed and encoded by synthetic oligonucleotides, including degenerate positions (IUPAC nucleotide code) highlighted in yellow. The corresponding amino acid sequence (UPPERCASE letters above nucleotide sequence) encoded by all possible codon combinations is shown in the line/s above. Amino acids highlighted in blue were selected for the inclusion into the library sequence because they were found in one or more naturally-occurring 150 variants used for the library design, while those that are not highlighted represent an additional amino acid diversity encoded by the degenerate nucleotides. Highlighted in orange are amino acid residues not encoded by the WT AAV2 sequence that were introduced during design to increase transduction efficiency (Y/F) or eliminate heparin binding (R/A). The amino acid residues in logo style shows the alignment of the sequences deduced from the NextGen sequencing of the library viral DNA. The X-axis designates residue position (VP1 numbering), and the Y-axis—the relative frequency of each amino acid at that position. Amino acids are colored according to their chemical properties: polar amino acids are green; basic, blue; acidic, red; and hydrophobic amino acids are black;

FIG. 3A: AAV2 capsid full capsid (assembled from 60 VP3 monomers shown to the right), displaying the location of the eight VRs, colored as described below the image of the monomer. FIG. 3B and FIG. 3C, respectively: LiA and LiC full capsids variants and their respective monomers. The mutated residues and their positions are shown by color and by number, respectively;

FIG. 4A, FIG. 4B, FIG. 4C, FIG. 4D, and FIG. 4E show the analysis of packaged viral library complexity. FIG. 4A: Shannon entropy of the viral library computed from 840 individual protein sequences. The X-axis designates residue position (VP1 numbering) and the Y-axis—computed value of the entropy; FIG. 4B: Distribution of the distinct capsid sequences and their copy numbers; FIG. 4C: Distribution of the number of mutations in the sample of analyzed protein sequences, FIG. 4D: Distribution of the number of mutant VRs. The different combinations of mutated VRs are designated by the respective colors shown to the right of the graph. The most frequently encountered mutant VRs combinations are also marked by the Roman numerals over the respective graph areas; FIG. 4E: Comparison of expected and observed percentages of mutant residues. The X-axis designates residue position (VP1 numbering); the respective VR boundaries are shown below amino acid numbers for better orientation. The Y-axis designates the percentage of the expected (introduced by design) mutation (blue) vs experimentally deduced from the sequencing of the plasmid library (red) vs viral library (green). The similitude of the graphs height at each position indicates a relative neutrality of this position for the capsid assembly/structure, whereas the difference between a theoretical (blue) and plasmid-derived sequences (red) indicates a selective pressure against this particular mutated residue within one single VR library, or within a context of all mutated VRs in the combined viral library (green). Because the sample of the sequenced plasmid library included only 21 individually sequenced random clones, due to the low sampling representation, the number of observed mutants (red) sometimes exceeds the expected frequency (blue) which always (with the exception of residues 444, 500, and 588) includes wt AAV2 residue.

FIG. 5A, FIG. 5B, FIG. 5C, FIG. 5D, FIG. 5E, and FIG. 5F show the selection of new variants from murine liver. FIG. 5A: Amino acid sequences of the variable regions (VRs) of the variants selected from the library after three rounds of directed evolution in the mouse liver. wt AAV2 sequences are shown in bold for comparison; FIG. 5B: Expression of luciferase transgene in the liver of mice at day 40 after tail-vein administration of rAAV vectors packaged into capsids as indicated; FIG. 5C: Time course of rAAV-Luc expression in the liver as assessed by Luciferase imaging in vivo. The Y-axis designates the level of bioluminescence (n=3 mice per group); FIG. 5D: Systemic expression of human F.IX in hemophilia B (C3H/HcJ/F9−/−) mice over 3 months following peripheral vein delivery of ApoE/hAAT-hF.IX transgene cassette packaged either in AAV8 (red), LiC (green) or AAV2-M3 (triple AAV2 mutant Y444F, Y500F and Y730F, blue) capsid (1010 vg/mouse, n=4/group); FIG. 5E: Systemic expression of human FIX in hemophilia B (C3H/HeJ/F9−/−) mice at 4 weeks following peripheral vein delivery of ApoE/hAAT-hF.IX transgene cassette packaged either in AAV8 (red) or LiA (yellow) capsid ($10^{10}$ vg/mouse, n=4/group); FIG. 5F: biodistribution study of LiA and LiC variants (tabulated as a number of viral genomes per ng of genomic DNA, Y-axis) conducted 23 days after peripheral vein delivery in BALB/c male mice (n=3), as compared to AAV2 and AAV8 (X-axis). Note predominantly liver-specific targeting of the selected variants LiA and LiC;

FIG. 7 shows the alignment of mutated regions in consensus and sequences found in more than 4 copies. Amino acid substitutions are highlighted, those occurring in the consensus (top sequence) are in yellow. The 9 sequences under the consensus were those found in more than 4 copies; copy number is indicated on the left. The total number of mutations is shown to the right of each sequence;

FIG. 11 shows barcoded AAV cassette. Top—diagram of barcoded AAV transgene cassette: TR—AAV2 terminal repeat; CBA—CMV-β-actin promoter; luc—firefly luciferase cDNA; furin-2A—furin cleavage site[41] followed by a foot-and-mouth disease virus 2A ribosomal skip peptide[42]; pA—bovine growth hormone gene polyadenylation site. Bottom—list of available 6 nt identifiers (barcodes)

DESCRIPTION OF ILLUSTRATIVE EMBODIMENTS

Figure 2:
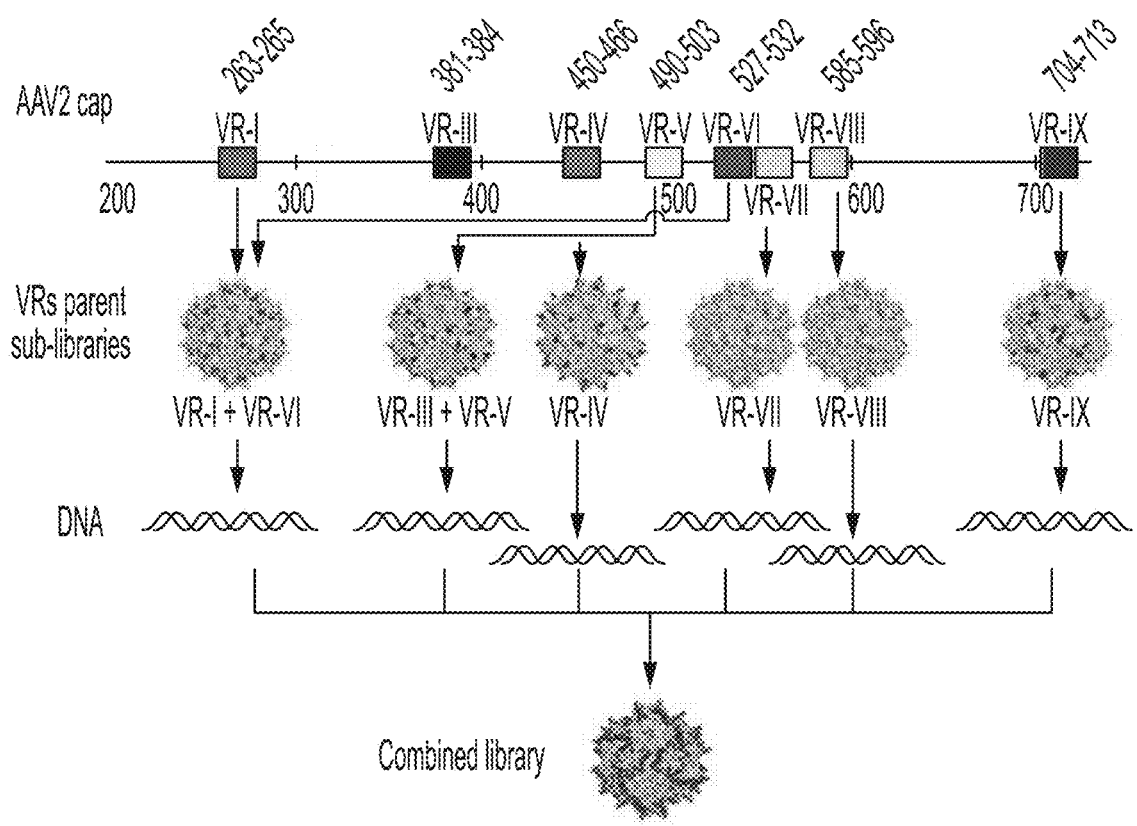
FIG. 2 shows a schematic representation of the CapLib design and construction steps. AAV2 capsid is shown at the top of the chart whereby numbers represent the respective amino acid residues. Variable region (VR) sub-libraries were packaged and purified (indicated by differentially colored VRs). DNAs from these individual sub-libraries were purified and used construct a final combined library.
Figures 3A, 3B, 3C:
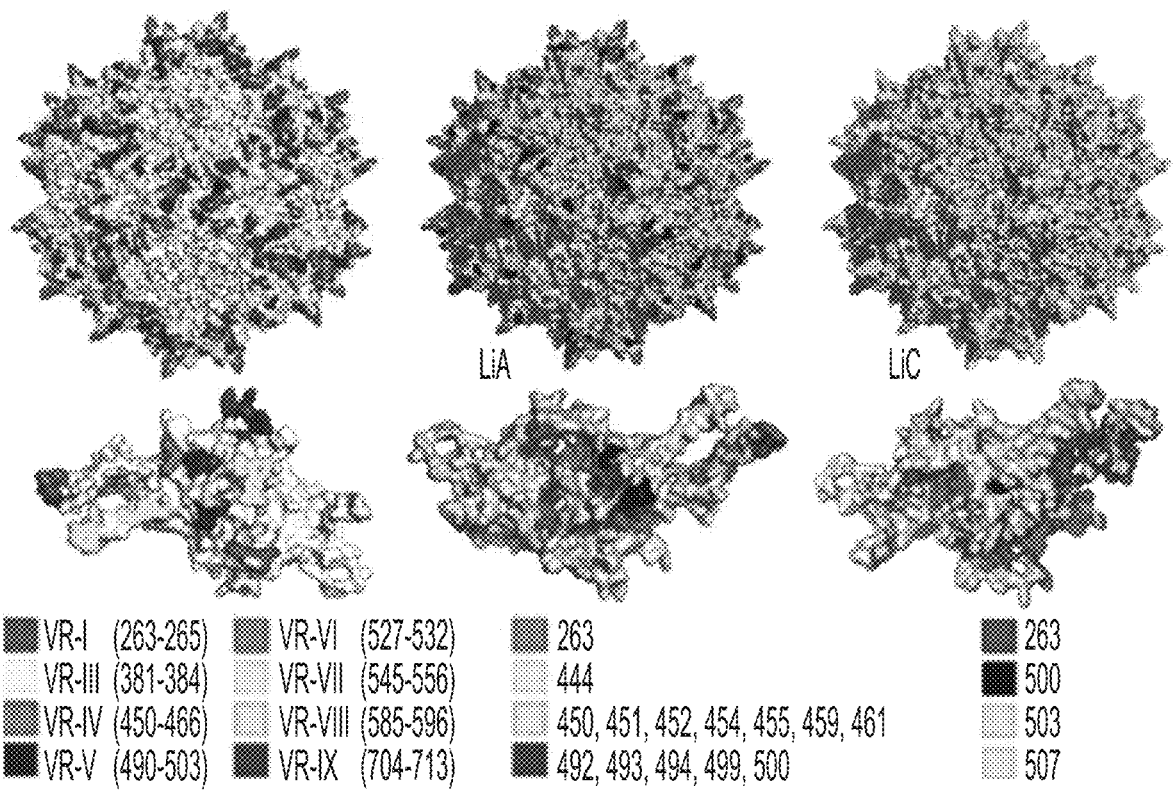
FIG. 3A, FIG. 3B, and FIG. 3C show variable regions (VRs) on the AAV2 capsid surface.
Figure 4E:
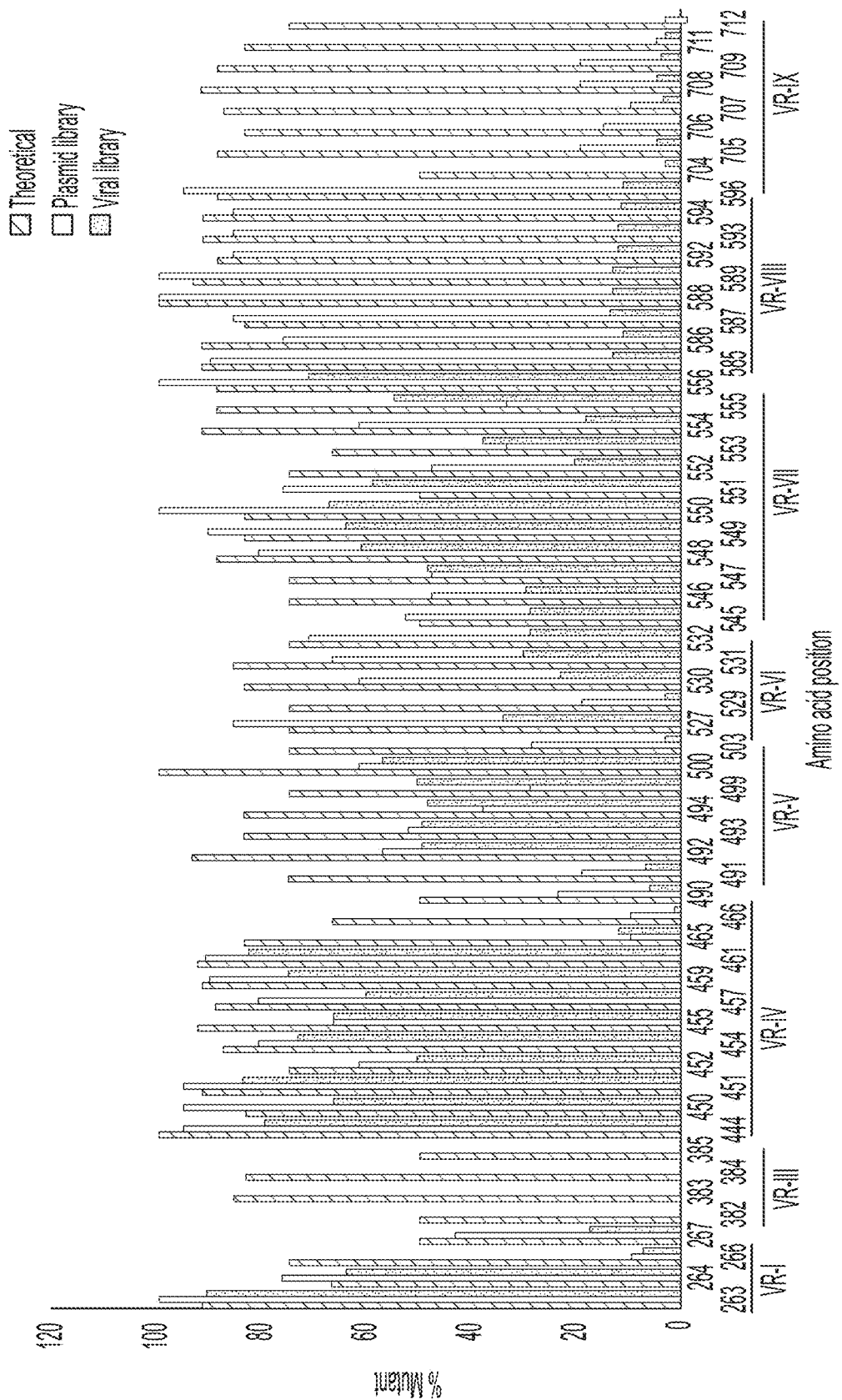
Figure 5D:
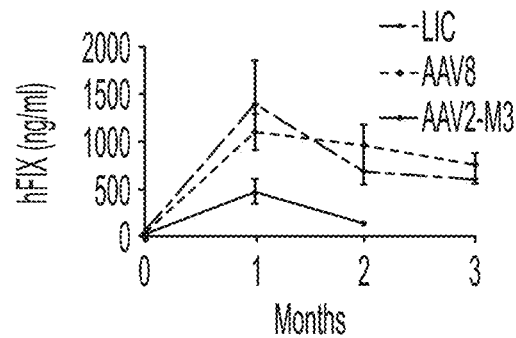
Figure 5E:
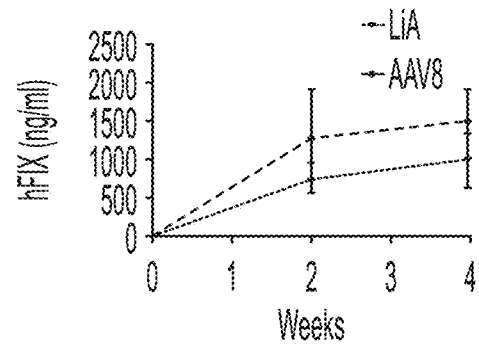
Figure 5F:
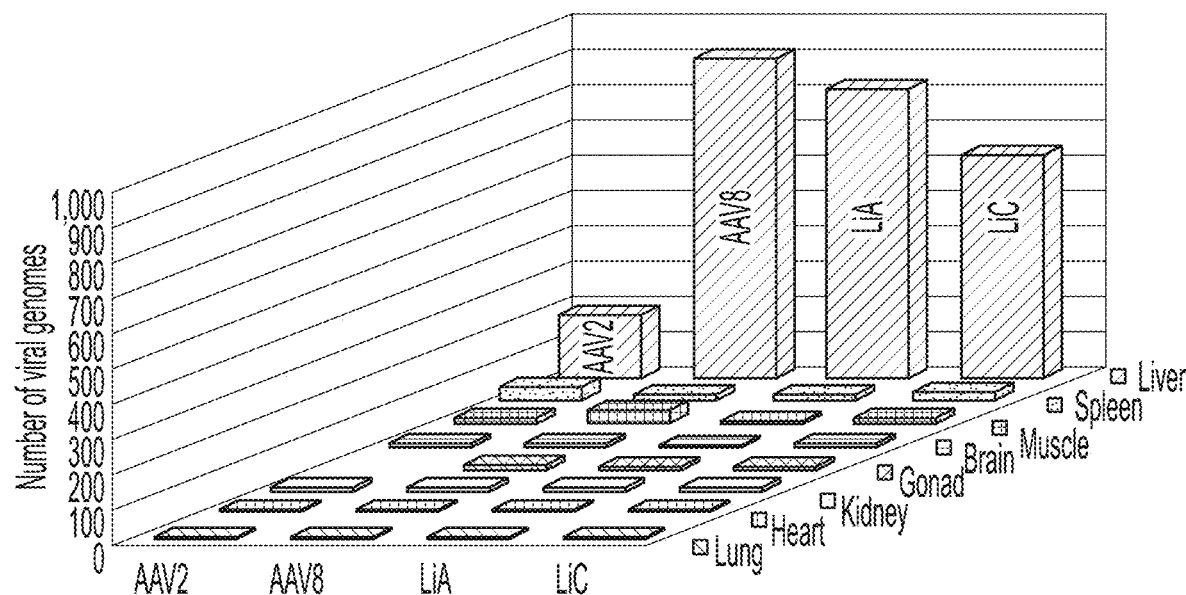
Figure 6A:
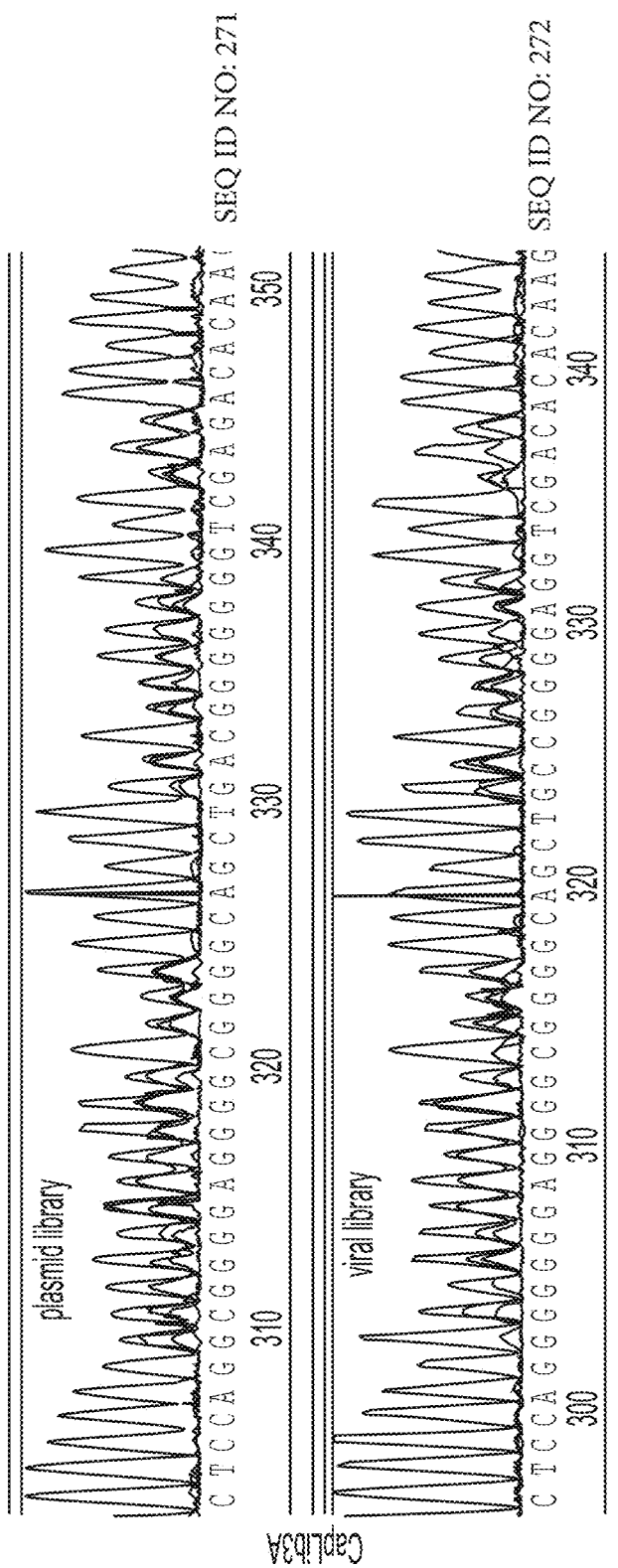
FIG. 6A and FIG. 6B show the nucleotide sequences of the Variable Region VIII (VR-VIII) in CapLib-3A (FIG. 6A) and CapLib-3B (FIG. 6B) plasmid and viral libraries. Shown are raw sequencing data to illustrate the selection pressure upon individual amino acid residues within one VR (VR-VIII) when all mutated VRs are combined in one library. The mutagenized and wt AA V2 reference sequences are shown below FIG. 6B.
Figure 6B:
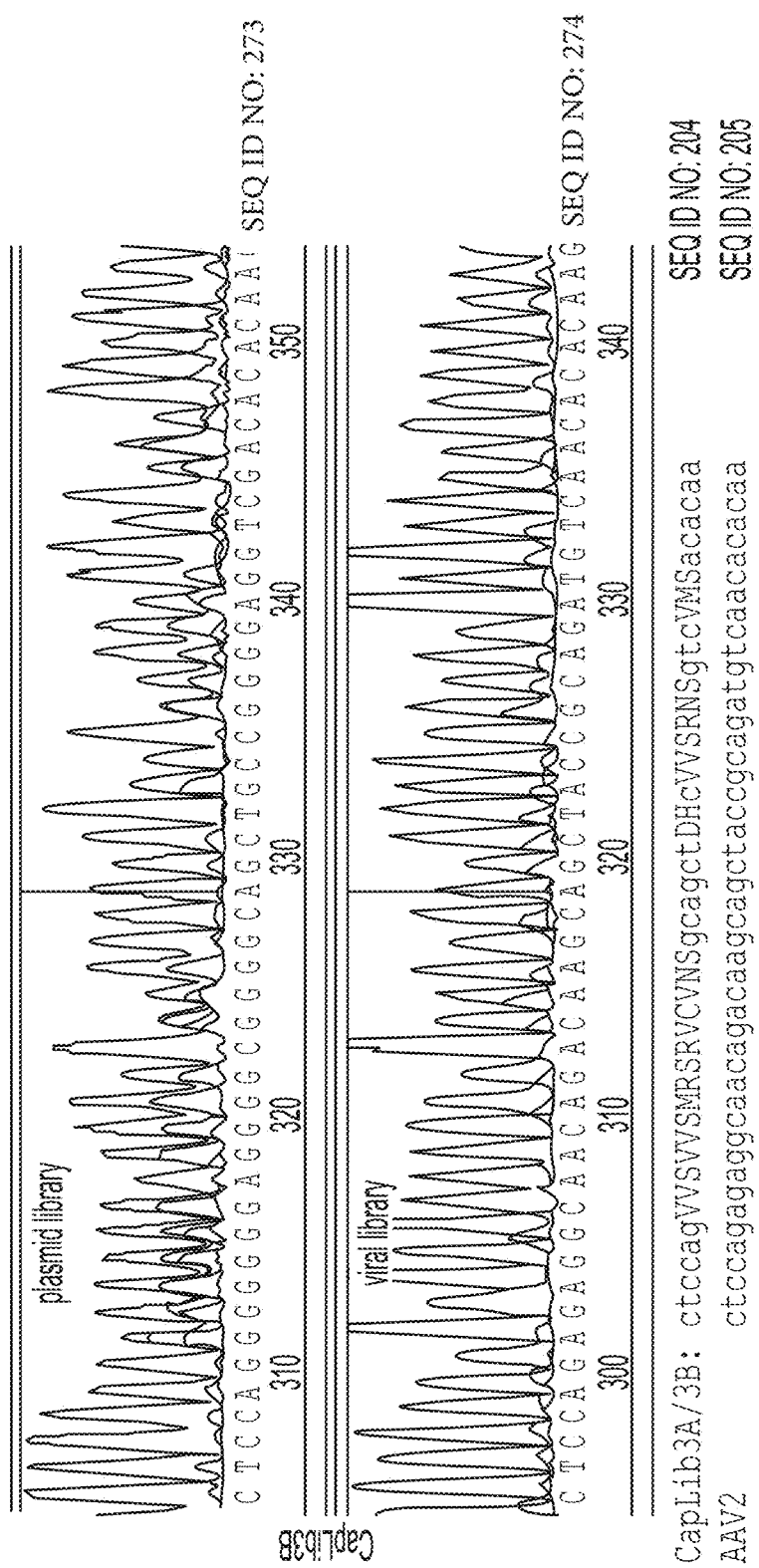
Figure 8:
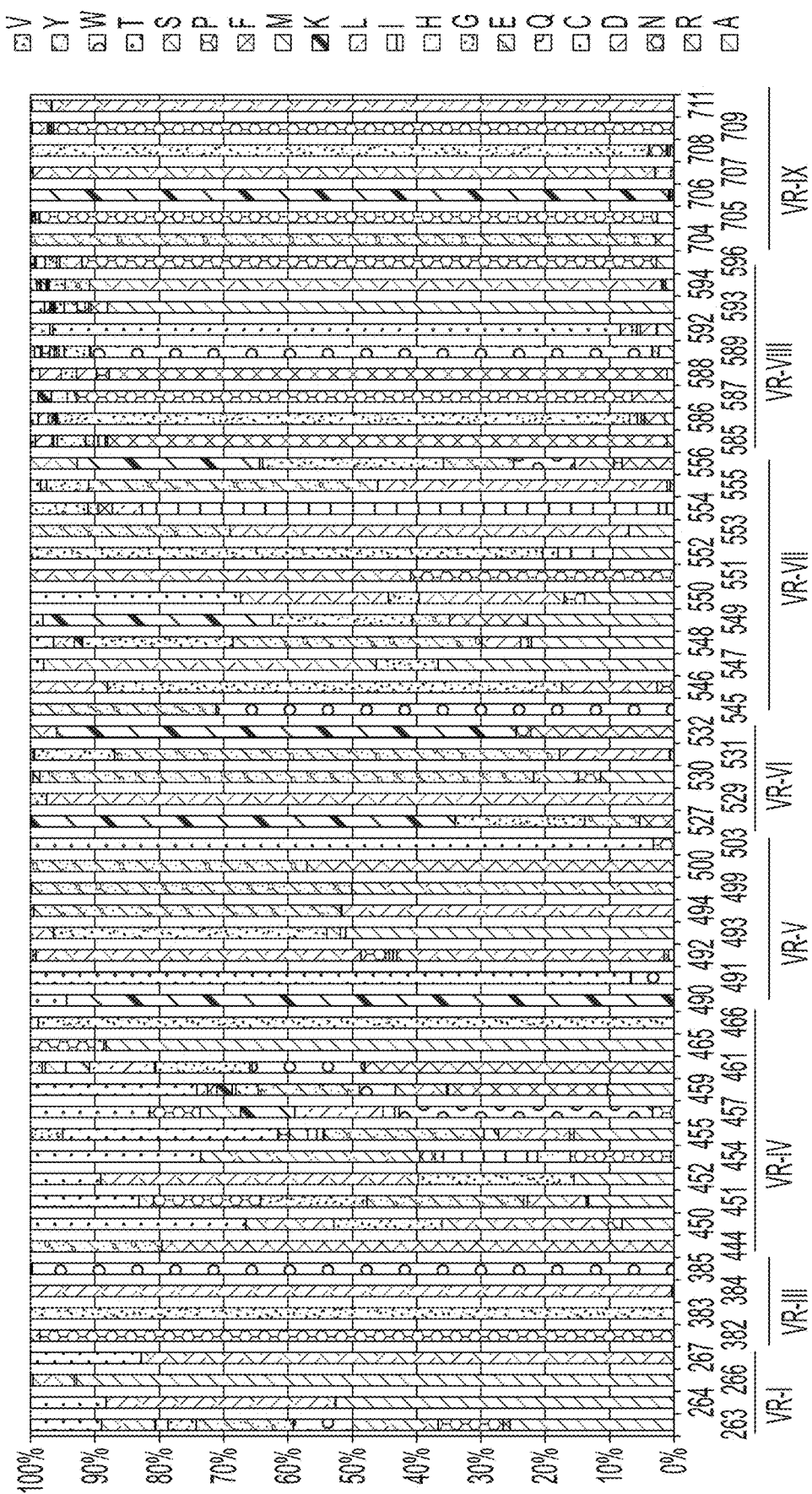
FIG. 8 shows the amino acid composition in variable positions. The X-axis designates residue position (VP1 numbering), and the Y-axis—the relative frequency of each amino acid at that position. Amino acid color-coding is shown to the right of the graph. The respective VR boundaries are shown below amino acid numbers for better orientation.
Figure 9:
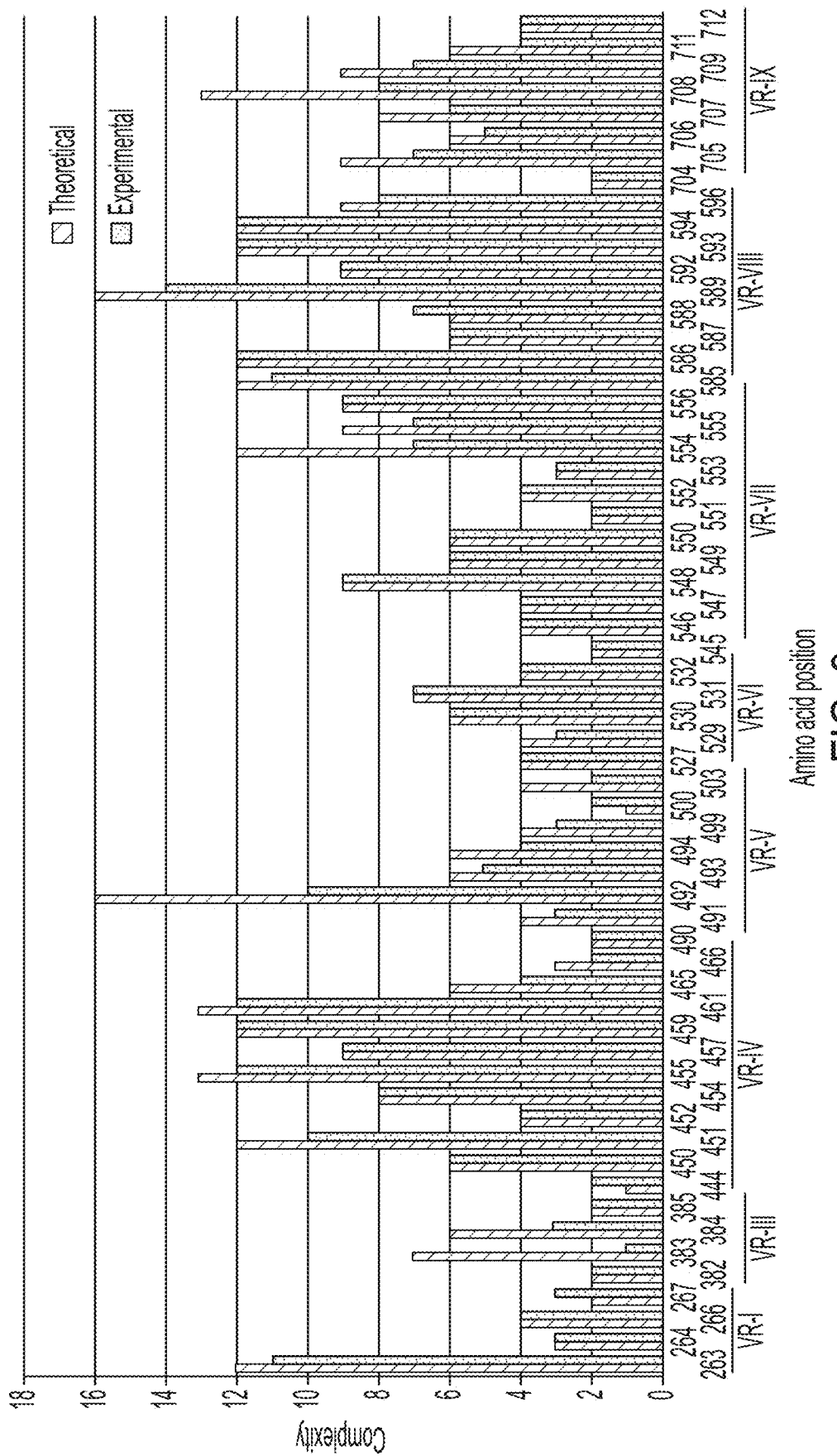
FIG. 9 shows the comparison of theoretical and experimental complexity at each variable amino acid position. The X-axis designates residue position (VP1 numbering), and the Y-axis—the theoretical (blue) and experimental (red) complexities at that position as reflected by total number of mutations. The respective VR boundaries are shown below amino acid numbers for better orientation.
Figure 10:
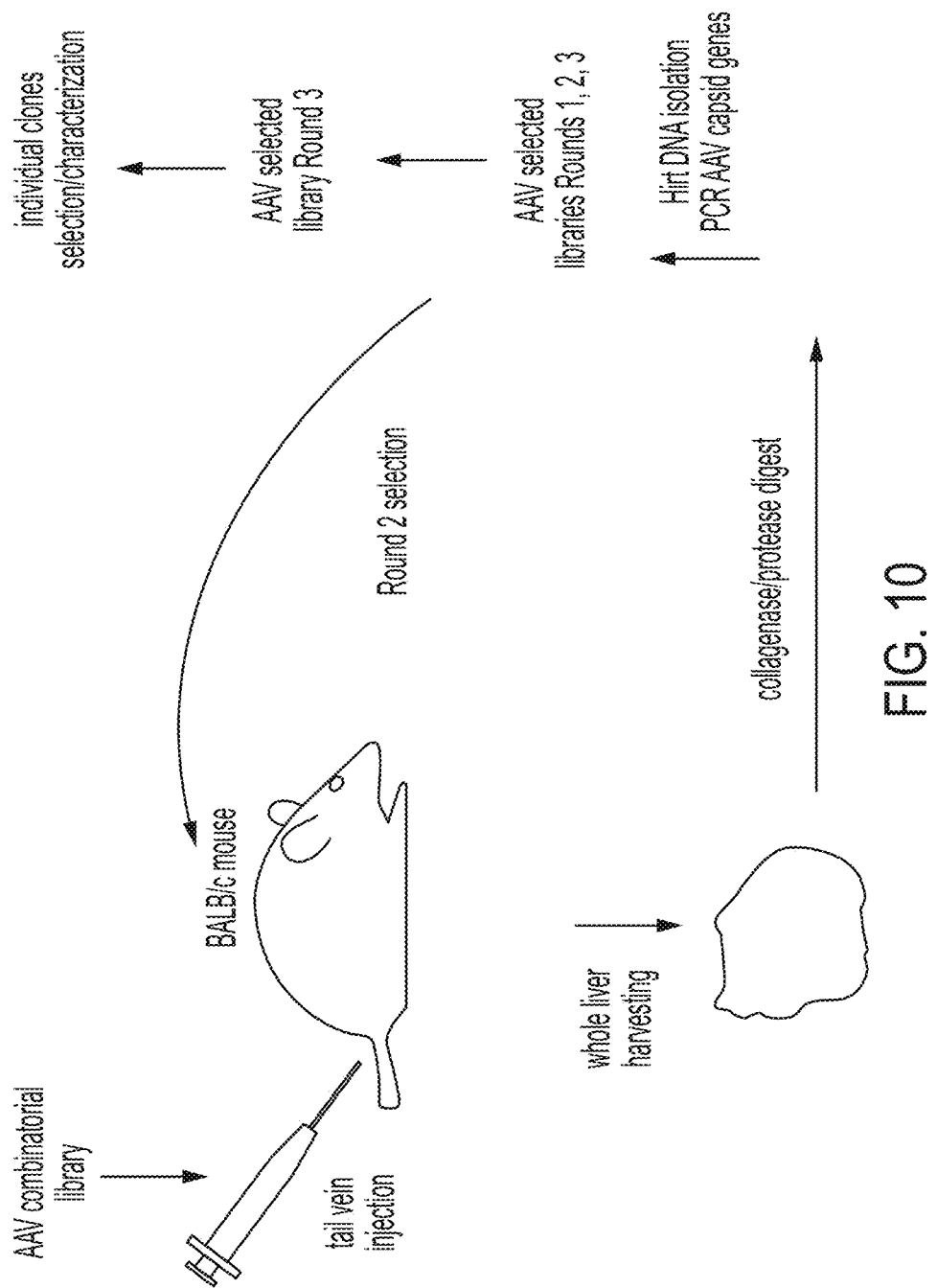
FIG. 10 shows a diagram of in vivo directed evolution. Viral library is injected intravenously (via tail vein). Three days post-injection, the liver is harvested and subjected to collagenase/protease treatment. Episomal flirt DNA was isolated from the whole organ and utilized to amplify AAV capsid gene sequences. A new, Round one-enriched library was prepared and the cycle was repeated. After 3 cycles, individual clones were sequenced and analyzed. The recurrent variants were selected and cap gene sequence was subcloned to derive a helper plasmid. rAAV vectors incorporating reporter genes were then packaged and their biodistribution was analyzed after intravenous administration.
Figure 12:
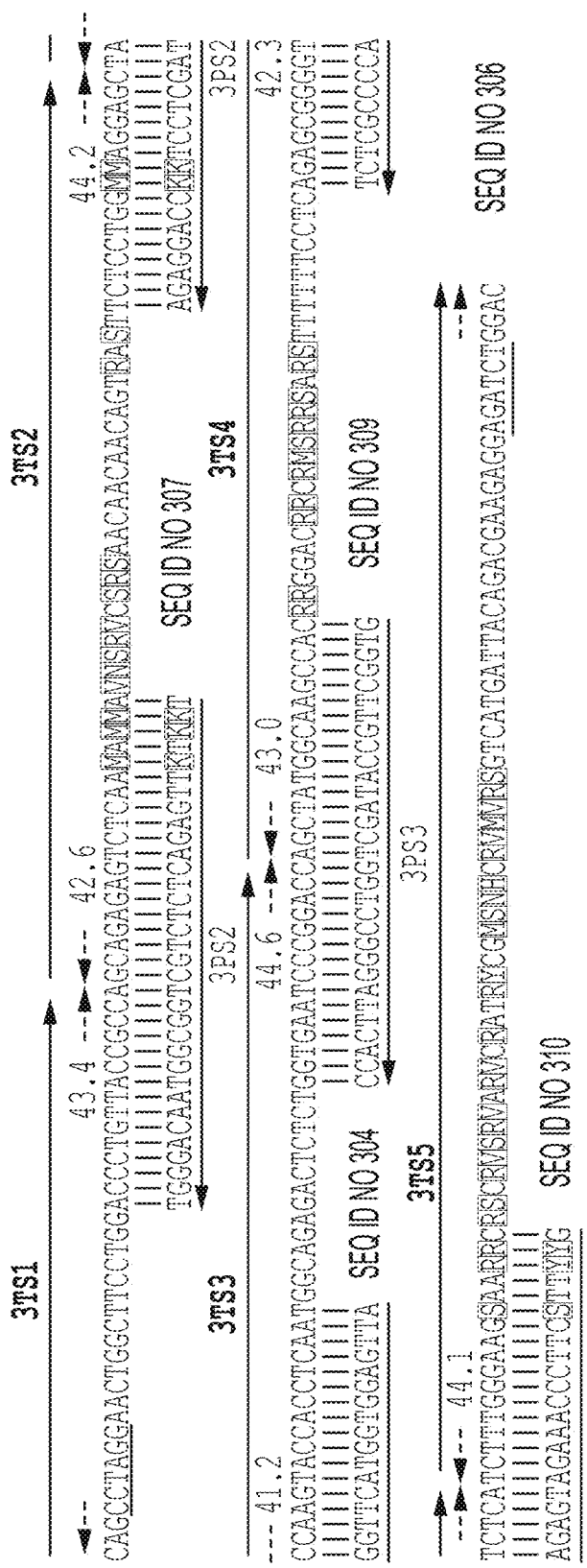
FIG. 12 shows a diagram of Fragment 3 assembly. Top strand scaffold oligonucleotides (shown in black color) were annealed to bottom strand anchor (shown in red) oligonucleotides. Degenerate positions (IUPAC nucleotide code) are highlighted by yellow background.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

The present invention also provides improved rAAV-based genetic constructs that encode one or more therapeutic agents useful in the preparation of medicaments for the prevention, treatment, and/or amelioration of one or more diseases, disorders or dysfunctions resulting from a deficiency in one or more cellular components. In particular, the invention provides libraries of rAAV-based genetic constructs encoding one or more selected molecules of interest, such as, for example, one or more diagnostic or therapeutic agents (including, e.g., proteins, polypeptides, peptides, antibodies, antigen binding fragments, siRNAs, RNAis, antisense oligo- and poly-nucleotides, ribozymes, and variants and/or active fragments thereof), for use in the diagnosis, prevention, treatment, and/or amelioration of symptoms of mammalian diseases, disorders, dysfunctions, deficiencies, defects, trauma, injury, and such like.

The present invention also provides infectious rAAV virions, as well as nucleic acid molecules and rAAV vectors that encode the novel AAV vectors described herein, as well as nucleic acids encoding one or more selected diagnostic and/or therapeutic agents for delivery to a selected population of mammalian cells.

Preferably, the novel rAAV vectors, express constructs, and infectious virions and viral particles comprising them as disclosed herein preferably have an improved efficiency in transducing one or more of a variety of cells, tissues and organs of interest, when compared to wild-type, unmodified, expression constructs, and to the corresponding rAAV vectors and virions comprising them.

The improved rAAV vectors provided herein may transduce one or more selected host cells at higher-efficiencies (and often much higher efficiencies) than conventional, wild type (i.e., "unmodified") rAAV vectors. Likewise, vectors prepared as described herein may be of different AAV serotypes, and the mutation of one or more of the sequences described herein may result in improved viral vectors, which are capable of higher-efficiency transduction than that of the corresponding, non-substituted vectors from which the mutants were prepared.

The development of next-generation rAAV viral vectors may dramatically reduce the number of viral particles needed for a conventional gene therapy regimen. In addition to having improved transduction efficiencies for various mammalian cells, the rAAV vectors prepared as described herein may be more stable, less immunogenic, and/or can be produced at much lower cost, or in a higher titer, than an equivalent wild type viral vector prepared in conventional fashion.

In the practice of the invention, native amino acids normally present in the sequence of a viral capsid protein, may be substituted by one or more non-native amino acids, including, a substitution of one or more amino acids not normally present at a particular residue in the corresponding wild-type protein.

The invention also provides isolated and purified polynucleotides that encode one or more of the disclosed viral vectors as described herein, as well as polynucleotides that encode such vectors. Preferably, the vector constructs of the present invention further include at least one nucleic acid segment that encodes a diagnostic or therapeutic molecule operably linked to a promoter capable of expressing the nucleic acid segment in a suitable host cell comprising the vector.

In the practice of the invention, the transduction efficiency of a mutated rAAV vector will be higher than that of the corresponding, unmodified, wild-type vector, and as such, will preferably possess a transduction efficiency in a mammalian cell that is at least 2-fold, at least about 4-fold, at least about 6-fold, at least about 8-fold, at least about 10-fold, or at least about 12-fold or higher in a selected mammalian host cell than that of a virion that comprises a corresponding, unmodified, rAAV vector. In certain embodiments, the transduction efficiency of the rAAV vectors provided herein will be at least about 15-fold higher, at least about 20-fold higher, at least about 25-fold higher, at least about 30-fold higher, or at least about 40, 45, or 50-fold or more greater than that of a virion that comprises a corresponding, wild-type vectors.

The present invention also concerns rAAV vectors, wherein the nucleic acid segment further comprises a promoter, an enhancer, a post-transcriptional regulatory sequence, a polyadenylation signal, or any combination thereof, operably linked to the nucleic acid segment that encodes the selected polynucleotide of interest. Preferably, the promoter is a heterologous promoter, a tissue-specific promoter, a cell-specific promoter, a constitutive promoter, an inducible promoter, or any combination thereof. In certain embodiments, nucleic acid segments cloned into one or more of the novel rAAV expression vectors described herein will preferably express or encode one or more polypeptides, peptides, ribozymes, peptide nucleic acids, siRNAs, RNAis, antisense oligonucleotides, antisense polynucleotides, antibodies, antigen binding fragments, or any combination thereof.

As noted herein, the therapeutic agents useful in the invention may include one or more agonists, antagonists, anti-apoptosis factors, inhibitors, receptors, cytokines, cytotoxins, erythropoietic agents, glycoproteins, growth factors, growth factor receptors, hormones, hormone receptors, interferons, interleukins, interleukin receptors, nerve growth factors, neuroactive peptides, neuroactive peptide receptors, proteases, protease inhibitors, protein decarboxylases, protein kinases, protein kinase inhibitors, enzymes, receptor binding proteins, transport proteins or one or more inhibitors thereof, serotonin receptors, or one or more uptake inhibitors thereof, serpins, serpin receptors, tumor suppressors, diagnostic molecules, chemotherapeutic agents, cytotoxins, or any combination thereof.

While the inventors particularly contemplate the use of rAAV2-based vectors in certain methods for gene therapy, vectors may also be prepared and packaged within virions of any known AAV serotype, including, for examples, AAV serotype 1 (AAV1), AAV serotype 3 (AAV3), AAV serotype 4 (AAV4), AAV serotype 5 (AAV5), AAV serotype 6 (AAV6), AAV serotype 7 (AAV7), AAV serotype 8 (AAV8), AAV serotype 9 (AAV9), AAV serotype 10 (AAV10), AAV serotype 11 (AAV11), or AAV serotype 12 (AAV12).

The invention further provides populations and pluralities of such rAAV vectors as prepared herein, as well as virions, infectious viral particles, and mammalian host cells that include one or more nucleic acid segments encoding them. Preferably, the mammalian host cells will be human host cells, including, for example blood cells, stem cells, hematopoietic cells, CD34$^+$ cells, liver cells, cancer cells, vascular cells, pancreatic cells, neural cells, ocular or retinal cells, epithelial or endothelial cells, dendritic cells, fibroblasts, or any other cell of mammalian origin, including, without limitation, hepatic (i.e., liver) cells, lung cells, cardiac cells, pancreatic cells, intestinal cells, diaphragmatic cells, renal (i.e., kidney) cells, neural cells, blood cells, bone marrow cells, or any one or more selected tissues of a mammal for which viral-based gene therapy is contemplated.

The invention further provides composition and formulations that include one or more of the proteins nucleic acid segments viral vectors, host cells, or viral particles of the present invention together with one or more pharmaceutically-acceptable buffers, diluents, or excipients. Such compositions may be included in one or more diagnostic or therapeutic kits, for diagnosing, preventing, treating or ameliorating one or more symptoms of a mammalian disease, injury, disorder, trauma or dysfunction.

The invention further includes a method for providing a mammal in need thereof with a diagnostically- or therapeutically-effective amount of a selected biological molecule, the method comprising providing to a cell, tissue or organ of a mammal in need thereof, an amount of an rAAV vector; and for a time effective to provide the mammal with a diagnostically- or a therapeutically-effective amount of the selected biological molecule.

The invention further provides a method for diagnosing, preventing, treating, or ameliorating at least one or more symptoms of a disease, a disorder, a dysfunction, an injury, an abnormal condition, or trauma in a mammal. In an overall and general sense, the method includes at least the step of administering to a mammal in need thereof one or more of the disclosed rAAV vectors, in an amount and for a time sufficient to diagnose, prevent, treat or ameliorate the one or more symptoms of the disease, disorder, dysfunction, injury, abnormal condition, or trauma in the mammal.

The invention also provides a method of transducing a population of mammalian cells. In an overall and general sense, the method includes at least the step of introducing into one or more cells of the population, a composition that comprises an effective amount of one or more of the rAAV vectors disclosed herein.

In a further embodiment, the invention also provides isolated nucleic acid segments that encode one or more of the mutant viral capsid proteins as described herein, and provides recombinant vectors, virus particles, infectious virions, and isolated host cells that comprise one or more of the improved vector sequences described and tested herein.

Additionally, the present invention provides compositions, as well as therapeutic and/or diagnostic kits that include one or more of the disclosed AAV compositions, formulated with one or more additional ingredients, or prepared with one or more instructions for their use.

The invention also demonstrates methods for making, as well as methods of using the disclosed improved rAAV vectors in a variety of ways, including, for example, ex situ, in vitro and in vivo applications, methodologies, diagnostic procedures, and/or gene therapy regimens. Because many of the improved vectors described herein are also resistant to proteasomal degradation, they possess significantly increased transduction efficiencies in vivo making them particularly well suited for viral vector-based human gene therapy regimens, and in particular, for delivering one or more genetic constructs to selected mammalian cells in vivo and/or in vitro.

In one aspect, the invention provides compositions comprising AAV vectors, virions, viral particles, and pharmaceutical formulations thereof, useful in methods for delivering genetic material encoding one or more beneficial or therapeutic product(s) to mammalian cells and tissues. In particular, the compositions and methods of the invention provide a significant advancement in the art through their use in the treatment, prevention, and/or amelioration of symptoms of one or more mammalian diseases. It is contemplated that human gene therapy will particularly benefit from the present teachings by providing new and improved viral vector constructs for use in the treatment of a number of diverse diseases, disorders, and dysfunctions.

In another aspect, the invention concerns libraries of rAAV vector mutants that demonstrate improved properties useful in the delivery of one or more therapeutic agents to selected mammalian cells, and particularly for use in the prevention, treatment, and/or amelioration of one or more disorders in a mammal into which the vector construct may be introduced.

The rAAV vectors of the present invention may optionally further include one or more enhancer sequences that are each operably linked to the nucleic acid segment. Exemplary enhancer sequences include, but are not limited to, one or more selected from the group consisting of a CMV enhancer, a synthetic enhancer, a liver-specific enhancer, an vascular-specific enhancer, a brain-specific enhancer, a neural cell-specific enhancer, a lung-specific enhancer, a muscle-specific enhancer, a kidney-specific enhancer, a pancreas-specific enhancer, and an islet cell-specific enhancer.

Exemplary promoters useful in the practice of the invention include, without limitation, one or more heterologous, tissue-specific, constitutive or inducible promoters, including, for example, but not limited to, a promoter selected from the group consisting of a CMV promoter, a β-actin promoter, an insulin promoter, an enolase promoter, a BDNF promoter, an NGF promoter, an EGF promoter, a growth factor promoter, an axon-specific promoter, a dendrite-specific promoter, a brain-specific promoter, a hippocampal-specific promoter, a kidney-specific promoter, an elafin promoter, a cytokine promoter, an interferon promoter, a growth factor promoter, an a1-antitrypsin promoter, a brain cell-specific promoter, a neural cell-specific promoter, a central nervous system cell-specific promoter, a peripheral nervous system cell-specific promoter, an interleukin promoter, a serpin promoter, a hybrid CMV promoter, a hybrid β-actin promoter, an EF1 promoter, a U1a promoter, a U1b promoter, a Tet-inducible promoter, a VP16-LexA promoter, or any combination thereof. In exemplary embodiments, the promoter may include a mammalian or avian p-actin promoter.

The vector-encoding nucleic acid segments may also further include one or more post-transcriptional regulatory sequences or one or more polyadenylation signals, including, for example, but not limited to, a woodchuck hepatitis virus post-transcription regulatory element, a polyadenylation signal sequence, or any combination thereof.

Exemplary diagnostic or therapeutic agents deliverable to host cells by the present vector constructs include, but are not limited to, an agent selected from the group consisting of a polypeptide, a peptide, an antibody, an antigen binding fragment, a ribozyme, a peptide nucleic acid, a siRNA, an RNAi, an antisense oligonucleotide, an antisense polynucleotide, and any combination thereof.

In exemplary embodiments, the rAAV vectors obtained by the disclosed methods will preferably encode at least one diagnostic or therapeutic protein or polypeptide selected from the group consisting of a molecular marker, an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinsase inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, a tumor suppressor, and any combination thereof.

In certain applications, the rAAV vectors of the present invention may include one or more nucleic acid segments that encode a polypeptide selected from the group consisting of BDNF, CNTF, CSF, EGF, FGF, G-SCF, GM-CSF, gonadotropin, IFN, IFG-1, M-CSF, NGF, PDGF, PEDF, TGF, TGF-B2, TNF, VEGF, prolactin, somatotropin, XIAP1, IL-1, IL-2, IL-3, IL-4, IL-5, IL-6, IL-7, IL-8, IL-9, IL-10, IL-10(I87A), viral IL-10, IL-11, IL-12, IL-13, IL-14, IL-15, IL-16, IL-17, IL-18, and any combination thereof.

In another embodiment, the invention concerns genetically-modified, improved-transduction-efficiency rAAV vectors that include at least a first nucleic acid segment that encodes one or more therapeutic agents that alter, inhibit, reduce, prevent, eliminate, or impair the activity of one or more endogenous biological processes in the cell. In particular embodiments, such therapeutic agents may be those that selectively inhibit or reduce the effects of one or more metabolic processes, dysfunctions, disorders, or diseases. In certain embodiments, the defect may be caused by injury or trauma to the mammal for which treatment is desired. In other embodiments, the defect may be caused the overexpression of an endogenous biological compound, while in other embodiments still; the defect may be caused by the under-expression or even lack of one or more endogenous biological compounds.

The genetically-modified rAAV vectors and expression systems of the present invention may also further optionally include a second distinct nucleic acid segment that comprises, consists essentially of, or consists of, one or more enhancers, one or more regulatory elements, one or more transcriptional elements, or any combination thereof, that alter, improve, regulate, and/or affect the transcription of the nucleotide sequence of interest expressed by the modified rAAV vectors.

For example, the rAAV vectors of the present invention may further include a second nucleic acid segment that comprises, consists essentially of, or consists of, a CMV enhancer, a synthetic enhancer, a cell-specific enhancer, a tissue-specific enhancer, or any combination thereof. The second nucleic acid segment may also further comprise, consist essentially of, or consist of, one or more intron sequences, one or more post-transcriptional regulatory elements, or any combination thereof.

The improved vectors and expression systems of the present invention may also optionally further include a polynucleotide that comprises, consists essentially of, or consists of, one or more polylinkers, restriction sites, and/or multiple cloning region(s) to facilitate insertion (cloning) of one or more selected genetic elements, genes of interest, or therapeutic or diagnostic constructs into the rAAV vector at a selected site within the vector.

In further aspects of the present invention, the exogenous polynucleotide(s) that may be delivered into suitable host cells by the improved, capsid-modified, rAAV vectors disclosed herein are preferably of mammalian origin, with polynucleotides encoding one or more polypeptides or peptides of human, non-human primate, porcine, bovine, ovine, feline, canine, equine, epine, caprine, or lupine origin being particularly preferred.

The exogenous polynucleotide(s) that may be delivered into host cells by the disclosed capsid-modified viral vectors may, in certain embodiments, encode one or more proteins, one or more polypeptides, one or more peptides, one or more enzymes, or one or more antibodies (or antigen-binding fragments thereof), or alternatively, may express one or more siRNAs, ribozymes, antisense oligonucleotides, PNA molecules, or any combination thereof. When combinational gene therapies are desired, two or more different molecules may be produced from a single rAAV expression system, or alternatively, a selected host cell may be transfected with two or more unique rAAV expression systems, each of which may comprise one or more distinct polynucleotides that encode a therapeutic agent.

In other embodiments, the invention also provides rAAV vector mutants that are comprised within an infectious adeno-associated viral particle or a virion, as well as pluralities of such virions or infectious particles. Such vectors and virions may be comprised within one or more diluents, buffers, physiological solutions or pharmaceutical vehicles, or formulated for administration to a mammal in one or more diagnostic, therapeutic, and/or prophylactic regimens. The vectors, virus particles, virions, and pluralities thereof of the present invention may also be provided in excipient formulations that are acceptable for veterinary administration to selected livestock, exotics, domesticated animals, and companion animals (including pets and such like), as well as to non-human primates, zoological or otherwise captive specimens, and such like.

The invention also concerns host cells that comprise at least one of the disclosed rAAV expression vectors, or one or more virus particles or virions that comprise such an expression vector. Such host cells are particularly mammalian host cells, with human host cells being particularly highly preferred, and may be either isolated, in cell or tissue culture. In the case of genetically modified animal models, the transformed host cells may even be comprised within the body of a non-human animal itself.

In certain embodiments, the creation of recombinant non-human host cells, and/or isolated recombinant human host cells that comprise one or more of the disclosed rAAV vectors is also contemplated to be useful for a variety of diagnostic, and laboratory protocols, including, for example, means for the production of large-scale quantities of the rAAV vectors described herein. Such virus production methods are particularly contemplated to be an improvement over existing methodologies including in particular, those that require very high titers of the viral stocks in order to be useful as a gene therapy tool. The inventors contemplate that one very significant advantage of the present methods will be the ability to utilize lower titers of viral particles in mammalian transduction protocols, yet still retain transfection rates at a suitable level.

Compositions comprising one or more of the disclosed rAAV vectors, expression systems, infectious AAV particles, or host cells also form part of the present invention, and particularly those compositions that further comprise at least a first pharmaceutically-acceptable excipient for use in therapy, and for use in the manufacture of medicaments for the treatment of one or more mammalian diseases, disorders, dysfunctions, or trauma. Such pharmaceutical compositions may optionally further comprise one or more diluents, buffers, liposomes, a lipid, a lipid complex; or the tyrosine-modified rAAV vectors may be comprised within a microsphere or a nanoparticle.

Pharmaceutical formulations suitable for intramuscular, intravenous, or direct injection into an organ or tissue or a plurality of cells or tissues of a human or other mammal are particularly preferred, however, the compositions disclosed herein may also find utility in administration to discreet areas of the mammalian body, including for example, formulations that are suitable for direct injection into one or more organs, tissues, or cell types in the body. Such injection sites include, but are not limited to, the brain, a joint or joint capsule, a synovium or subsynovium tissue, tendons, ligaments, cartilages, bone, peri-articular muscle or an articular space of a mammalian joint, as well as direct administration to an organ such as the heart, liver, lung, pancreas, intestine, brain, bladder, kidney, or other site within the patient's body, including, for example, introduction of the viral vectors via intraabdominal, intrathorascic, intravascular, or intracerebroventricular delivery.

Other aspects of the invention concern recombinant adeno-associated virus virion particles, compositions, and host cells that comprise, consist essentially of, or consist of, one or more of the rAAV vectors disclosed herein, such as for example pharmaceutical formulations of the vectors intended for administration to a mammal through suitable means, such as, by intramuscular, intravenous, intra-articular, or direct injection to one or more cells, tissues, or organs of a selected mammal. Typically, such compositions may be formulated with pharmaceutically-acceptable excipients as described hereinbelow, and may comprise one or more liposomes, lipids, lipid complexes, microspheres or nanoparticle formulations to facilitate administration to the selected organs, tissues, and cells for which therapy is desired.

Kits comprising one or more of the disclosed rAAV vectors (as well as one or more virions, viral particles, transformed host cells or pharmaceutical compositions comprising such vectors); and instructions for using such kits in one or more therapeutic, diagnostic, and/or prophylactic clinical embodiments are also provided by the present invention. Such kits may further comprise one or more reagents, restriction enzymes, peptides, therapeutics, pharmaceutical compounds, or means for delivery of the composition(s) to host cells, or to an animal (e.g., syringes, injectables, and the like). Exemplary kits include those for treating, preventing, or ameliorating the symptoms of a disease, deficiency, dysfunction, and/or injury, or may include components for the large-scale production of the viral vectors themselves, such as for commercial sale, or for use by others, including e.g., virologists, medical professionals, and the like.

Another important aspect of the present invention concerns methods of use of the disclosed rAAV vectors, virions, expression systems, compositions, and host cells described herein in the preparation of medicaments for diagnosing, preventing, treating or ameliorating at least one or more symptoms of a disease, a dysfunction, a disorder, an abnormal condition, a deficiency, injury, or trauma in an animal, and in particular, in a vertebrate mammal. Such methods generally involve administration to a mammal in need thereof, one or more of the disclosed vectors, virions, viral particles, host cells, compositions, or pluralities thereof, in an amount and for a time sufficient to diagnose, prevent, treat, or lessen one or more symptoms of such a disease, dysfunction, disorder, abnormal condition, deficiency, injury, or trauma in the affected animal. The methods may also encompass prophylactic treatment of animals suspected of having such conditions, or administration of such compositions to those animals at risk for developing such conditions either following diagnosis, or prior to the onset of symptoms.

As described above, the exogenous polynucleotide will preferably encode one or more proteins, polypeptides, peptides, ribozymes, or antisense oligonucleotides, or a combination of these. In fact, the exogenous polynucleotide may encode two or more such molecules, or a plurality of such molecules as may be desired. When combinational gene therapies are desired, two or more different molecules may be produced from a single rAAV expression system, or alternatively, a selected host cell may be transfected with two or more unique rAAV expression systems, each of which will provide unique heterologous polynucleotides encoding at least two different such molecules.

Compositions comprising one or more of the disclosed rAAV vectors, expression systems, infectious AAV particles, host cells also form part of the present invention, and particularly those compositions that further comprise at least a first pharmaceutically-acceptable excipient for use in the manufacture of medicaments and methods involving therapeutic administration of such rAAV vectors. Such pharmaceutical compositions may optionally further comprise liposomes, a lipid, a lipid complex; or the rAAV vectors may be comprised within a microsphere or a nanoparticle. Pharmaceutical formulations suitable for intramuscular, intravenous, or direct injection into an organ or tissue of a human are particularly preferred.

Use of rAAV Vectors in Prophylaxis, Diagnosis, or Therapy

The present invention provides compositions including one or more of the disclosed rAAV vectors comprised within a kit for diagnosing, preventing, treating or ameliorating one or more symptoms of a mammalian disease, injury, disorder, trauma or dysfunction. Such kits may be useful in the diagnosis, prophylaxis, and/or therapy or a human disease, and may be particularly useful in the treatment, prevention, and/or amelioration of one or more symptoms of cancer, diabetes, autoimmune disease, kidney disease, cardiovascular disease, pancreatic disease, intestinal disease, liver disease, neurological disease, neuromuscular disorder, neuromotor deficit, neuroskeletal impairment, neurological disability, neurosensory dysfunction, stroke, ischemia, $\alpha_1$-antitrypsin (AAT) deficiency, Batten's disease, Alzheimer's disease, sickle cell disease, β-thalassamia, Huntington's disease, Parkinson's disease, skeletal disease, trauma, pulmonary disease in a human.

The invention also provides for the use of a composition disclosed herein in the manufacture of a medicament for treating, preventing or ameliorating the symptoms of a disease, disorder, dysfunction, injury or trauma, including, but not limited to, the treatment, prevention, and/or prophylaxis of a disease, disorder or dysfunction, and/or the amelioration of one or more symptoms of such a disease, disorder or dysfunction.

The invention also provides a method for treating or ameliorating the symptoms of such a disease, injury, disorder, or dysfunction in a mammal. Such methods generally involve at least the step of administering to a mammal in need thereof, one or more of the rAAV vectors as disclosed herein, in an amount and for a time sufficient to treat or ameliorate the symptoms of such a disease, injury, disorder, or dysfunction in the mammal. Such treatment regimens are particularly contemplated in human therapy, via administration of one or more compositions either intramuscularly, intravenously, subcutaneously, intrathecally, intrapcritoneally, or by direct injection into an organ or a tissue of the mammal under care.

The invention also provides a method for providing to a mammal in need thereof, a therapeutically-effective amount of an rAAV composition of the present invention, in an amount, and for a time effective to provide the patient with a therapeutically-effective amount of the desired therapeutic agent(s) encoded by one or more nucleic acid segments comprised within the rAAV vector. Exemplary therapeutic agents include, but are not limited to, a polypeptide, a peptide, an antibody, an antigen-binding fragment, a ribozyme, a peptide nucleic acid, an siRNA, an RNAi, an antisense oligonucleotide, an antisense polynucleotide, or a combination thereof.

Pharmaceutical Compositions

The genetic constructs of the present invention may be prepared in a variety of compositions, and may also be formulated in appropriate pharmaceutical vehicles for administration to human or animal subjects.

The invention also provides compositions comprising one or more of the disclosed rAAV vectors, expression systems, virions, viral particles, mammalian cells, or combinations thereof. In certain embodiments, the present invention provides pharmaceutical formulations of one or more rAAV vectors disclosed herein for administration to a cell or an animal, either alone or in combination with one or more other modalities of therapy, and in particular, for therapy of human cells, tissues, and diseases affecting man. Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intra-articular, intramuscular administration and formulation.

Exemplary Definitions

Unless otherwise defined, all technical terms used herein have the same meaning as commonly understood by one of ordinary skill in the art to which this invention belongs. Commonly understood definitions of molecular biology terms can be found in Rieger et al., (1991); Lewin (1994). Commonly understood definitions of virology terms can be found in Granoff and Webster (1999) and Tidona and Darai (2002). Commonly understood definitions of microbiology can be found in Singleton and Sainsbury (2002).

In accordance with long standing patent law convention, the words "a" and "an" when used in this application, including the claims, denotes "one or more."

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "carrier" is intended to include any solvent(s), dispersion medium, coating(s), diluent(s), buffer(s), isotonic agent(s), solution(s), suspension(s), colloid(s), inert(s) or such like, or a combination thereof, that is pharmaceutically acceptable for administration to the relevant animal. The use of one or more delivery vehicles for chemical compounds in general, and chemotherapeutics in particular, is well known to those of ordinary skill in the pharmaceutical arts. Except insofar as any conventional media or agent is incompatible with the active ingredient, its use in the diagnostic, prophylactic, and therapeutic compositions is contemplated. One or more supplementary active ingredient(s) may also be incorporated into, or administered in association with, one or more of the disclosed chemotherapeutic compositions.

As used herein, the term "chimeric rcAAV" refers to a replication-competent AAV-derived nucleic acid containing at least one nucleotide sequence that 1) encodes an AAV protein and 2) differs from the corresponding native nucleotide sequence in one or more bases.

As used herein, the term "DNA segment" refers to a DNA molecule that has been isolated free of total genomic DNA of a particular species. Therefore, a DNA segment obtained from a biological sample using one of the compositions disclosed herein refers to one or more DNA segments that have been isolated away from, or purified free from, total genomic DNA of the particular species from which they are obtained. Included within the term "DNA segment," are DNA segments and smaller fragments of such segments, as well as recombinant vectors, including, for example, plasmids, cosmids, phage, viruses, and the like.

The term "e.g.," as used herein, is used merely by way of example, without limitation intended, and should not be construed as referring only those items explicitly enumerated in the specification.

As used herein, "an effective amount" would be understood by those of ordinary skill in the art to provide a therapeutic, prophylactic, or otherwise beneficial effect against the organism, its infection, or the symptoms of the organism or its infection, or any combination thereof.

The phrase "expression control sequence" refers to any genetic element (e.g., polynucleotide sequence) that can exert a regulatory effect on the replication or expression (transcription or translation) of another genetic element. Common expression control sequences include promoters, polyadenylation (polyA) signals, transcription termination sequences, upstream regulatory domains, origins of replication, internal ribosome entry sites (IRES), enhancers, and the like. A "tissue specific expression control sequence" is one that exerts a regulatory effect on the replication or expression (transcription or translation) of another genetic element in only one type of tissue or a small subset of tissues.

The phrase "helper function" is meant as a functional activity performed by a nucleic acid or polypeptide that is derived from a virus such as Adenovirus (Ad) or herpesvirus and that facilitates AAV replication in a host cell.

As used herein, a "heterologous" is defined in relation to a predetermined referenced gene sequence. For example, with respect to a structural gene sequence, a heterologous promoter is defined as a promoter which does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

As used herein, the term "homology" refers to a degree of complementarity between two or more polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

As used herein, "homologous" means, when referring to polynucleotides, sequences that have the same essential nucleotide sequence, despite arising from different origins. Typically, homologous nucleic acid sequences are derived from closely related genes or organisms possessing one or more substantially similar genomic sequences. By contrast, an "analogous" polynucleotide is one that shares the same function with a polynucleotide from a different species or organism, but may have a significantly different primary nucleotide sequence that encodes one or more proteins or polypeptides that accomplish similar functions or possess similar biological activity. Analogous polynucleotides may often be derived from two or more organisms that are not closely related (e.g., either genetically or phylogenetically).

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of ordinary skill) or by visual inspection.

As used herein, the phrase "in need of treatment" refers to a judgment made by a caregiver such as a physician or veterinarian that a patient requires (or will benefit in one or more ways) from treatment. Such judgment may made based on a variety of factors that are in the realm of a caregiver's expertise, and may include the knowledge that the patient is ill as the result of a disease state that is treatable by one or more compound or pharmaceutical compositions such as those set forth herein.

The phrases "isolated" or "biologically pure" refer to material that is substantially, or essentially, free from components that normally accompany the material as it is found in its native state. Thus, isolated polynucleotides in accordance with the invention preferably do not contain materials normally associated with those polynucleotides in their natural, or in situ, environment.

As used herein, the term "kit" may be used to describe variations of the portable, self-contained enclosure that includes at least one set of components to conduct one or more of the diagnostic or therapeutic methods of the invention.

The term "library" refers to a collection of elements that differ from one another in at least one aspect. For example, a vector library is a collection of at least two vectors that differ from one another by at least one nucleotide. As another example, a "virion library" is a collection of at least two virions that differ from one another by at least one nucleotide or at least one capsid protein.

Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

As used herein, the term "master" library refers to a pool of rAAV virions composed of chimeric rcAAV vectors encapsidated in cognate chimeric capsids (e.g., capsids containing a degenerate or otherwise modified Cap protein).

When referring to a nucleic acid molecule or polypeptide, the term "native" refers to a naturally-occurring (e.g., a WT) nucleic acid or polypeptide.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally occurring animals As used herein, the phrase "nucleic acid" means a chain of two or more nucleotides such as RNA (ribonucleic acid) and DNA (deoxyribonucleic acid). The phrases "cap nucleic acid," "cap gene," and "capsid gene" as used herein mean a nucleic acid that encodes a Cap protein. Examples of cap nucleic acids include "wild-type" (WT) Cap-encoding nucleic acid sequences from AAV serotypes 1, 2, and 5; a native form cap cDNA; a nucleic acid having sequences from which a cap cDNA can be transcribed; and/or allelic variants and homologs of the foregoing.

As used herein, the term "patient" (also interchangeably referred to as "host" or "subject") refers to any host that can receive one or more of the pharmaceutical compositions disclosed herein. Preferably, the subject is a vertebrate animal, which is intended to denote any animal species (and preferably, a mammalian species such as a human being). In certain embodiments, a "patient" refers to any animal host including without limitation any mammalian host. Preferably, the term refers to any mammalian host, the latter including but not limited to, human and non-human primates, bovines, canines, caprines, cavines, corvines, epines, equines, felines, hircines, lapines, leporines, lupines, murines, ovines, porcines, ranines, racines, vulpines, and the like, including livestock, zoological specimens, exotics, as well as companion animals, pets, and any animal under the care of a veterinary practitioner.

The phrase "pharmaceutically-acceptable" refers to molecular entities and compositions that preferably do not produce an allergic or similar untoward reaction when administered to a mammal, and in particular, when administered to a human. As used herein, "pharmaceutically acceptable salt" refers to a salt that preferably retains the desired biological activity of the parent compound and does not impart any undesired toxicological effects. Examples of such salts include, without limitation, acid addition salts formed with inorganic acids (e.g., hydrochloric acid, hydrobromic acid, sulfuric acid, phosphoric acid, nitric acid, and the like); and salts formed with organic acids including, without limitation, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N'-dibenzylethylenediamine or ethylenediamine; and combinations thereof.

The term "pharmaceutically acceptable salt" as used herein refers to a compound of the present disclosure derived from pharmaceutically acceptable bases, inorganic or organic acids. Examples of suitable acids include, but are not limited to, hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkalis such as sodium and ammonia.

As used herein, the term "plasmid" or "vector" refers to a genetic construct that is composed of genetic material (i.e., nucleic acids). Typically, a plasmid or a vector contains an origin of replication that is functional in bacterial host cells, e.g., *Escherichia coli*, and selectable markers for detecting bacterial host cells including the plasmid. Plasmids and vectors of the present invention may include one or more genetic elements as described herein arranged such that an inserted coding sequence can be transcribed and translated in a suitable expression cells. In addition, the plasmid or vector may include one or more nucleic acid segments, genes, promoters, enhancers, activators, multiple cloning regions, or any combination thereof, including segments that are obtained from or derived from one or more natural and/or artificial sources. As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gin), Glutamic Acid (E; Glu), Glycine (G; Gly), Histidine (H; His), Isoleucine (I; Ile), Leucine (L Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

As used herein, the terms "prevent," "preventing," "prevention," "suppress," "suppressing," and "suppression" as used herein refer to administering a compound either alone or as contained in a pharmaceutical composition prior to the onset of clinical symptoms of a disease state so as to prevent any symptom, aspect or characteristic of the disease state. Such preventing and suppressing need not be absolute to be deemed medically useful.

The term "promoter," as used herein refers to a region or regions of a nucleic acid sequence that regulates transcription.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to any amino acid chain length, including those of short peptides from two to about 20 amino acid residues in length, oligopeptides from about 10 to about 100 amino acid residues in length, and longer polypeptides including those of about 100 or more amino acid residues in length. Furthermore, the term is also intended to include enzymes, i.e., functional biomolecules including at least one amino acid polymer. Polypeptides and proteins of the present invention also include polypeptides and proteins that are or have been post-translationally modified, and include any sugar or other derivative(s) or conjugate(s) added to the backbone amino acid chain.

The term "pseudotyped" is meant a nucleic acid or genome derived from a first AAV serotype that is encapsidated (packaged) into an AAV capsid containing at least one AAV Cap protein of a second serotype differing from the first serotype.

As used herein, the term "rcAAV vector" refers to a replication-competent AAV-derived nucleic acid capable of DNA replication in a cell without any additional AAV genes or gene products.

The term "recombinant" indicates that the material (e.g., a polynucleotide or a polypeptide) has been artificially or synthetically (non-naturally) altered by human intervention. The alteration can be performed on the material within or removed from, its natural environment or state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant AAV virus, is produced by the expression of a recombinant nucleic acid.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "RNA segment" refers to an RNA molecule that has been isolated free of total cellular RNA of a particular species. Therefore, RNA segments can refer to one or more RNA segments (either of native or synthetic origin) that have been isolated away from, or purified free from, other RNAs. Included within the term "RNA segment," are RNA segments and smaller fragments of such segments.

By the term "seed library" is meant a pool of AAV virions composed of chimeric rcAAV vectors encapsidated into AAV capsids of a single serotype.

The terms "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

As used herein, the term "structural gene" is intended to generally describe a polynucleotide, such as a gene, that is expressed to produce an encoded peptide, polypeptide, protein, ribozyme, catalytic RNA molecule, or antisense molecule.

The term "subject," as used herein, describes an organism, including a mammal such as a human primate, to which treatment with one or more of the disclosed compositions may be provided. Mammalian species that may benefit from the disclosed treatment methods include, without limitation, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like.

As used herein, the terms "terminal repeat" or "TR" mean a nucleic acid sequence derived from an AAV that is required in cis for replication and packaging of AAV.

"Transcriptional regulatory element" refers to a polynucleotide sequence that activates transcription alone or in combination with one or more other nucleic acid sequences. A transcriptional regulatory element may include, for example, one or more promoters, one or more response elements, one or more negative regulatory elements, one or more enhancers, or any combination thereof.

As used herein, a "transcription factor recognition site" and a "transcription factor binding site" refer to a polynucleotide sequence(s) or sequence motif(s) that are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted based on known consensus sequence motifs, or by other methods known to one of ordinary skill in the relevant molecular biological and virology arts.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

As used herein, the term "transformed cell" is intended to mean a host cell whose nucleic acid complement has been altered by the introduction of one or more exogenous polynucleotides into that cell.

As used herein, the term "transformation" is intended to generally describe a process of introducing an exogenous polynucleotide sequence (e.g., a viral vector, a plasmid, or a recombinant DNA or RNA molecule) into a host cell or protoplast in which the exogenous polynucleotide is incorporated into at least a first chromosome or is capable of autonomous replication within the transformed host cell. Transfection, electroporation, and "naked" nucleic acid uptake all represent examples of techniques used to transform a host cell with one or more polynucleotides.

As used herein, the terms "treat," "treating," and "treatment" refer to the administration of one or more compounds (either alone or as contained in one or more pharmaceutical compositions) after the onset of clinical symptoms of a disease state so as to reduce, or eliminate any symptom, aspect or characteristic of the disease state. Such treating need not be absolute to be deemed medically useful. As such, the terms "treatment," "treat," "treated," or "treating" may refer to therapy, or to the amelioration or the reduction, in the extent or severity of disease, of one or more symptom thereof, whether before or after its development afflicts a patient.

As used herein, the term "vector" refers to a nucleic acid molecule capable of transporting another nucleic acid to which it has been linked, e.g., a plasmid. One type of preferred vector is an episome, i.e., a nucleic acid capable of extra-chromosomal replication. Preferred vectors are those capable of autonomous replication and/or expression of nucleic acids to which they are linked. An "rAAV vector" is a recombinant AAV-derived nucleic acid containing at least one terminal repeat (TR) sequence.

The use of "virion" is meant to describe a virus particle that contains a nucleic acid and a protein coat (capsid). An "rAAV virion" is a virion that includes nucleic acid sequences and/or proteins derived from a rAAV vector.

The term "a sequence essentially as set forth in SEQ ID NO:X" means that the sequence substantially corresponds to a portion of SEQ ID NO:X and has relatively few nucleotides (or amino acids in the case of polypeptide sequences) that are not identical to, or a biologically functional equivalent of, the nucleotides (or amino acids) of SEQ ID NO:X. The term "biologically functional equivalent" is well understood in the art, and is further defined in detail herein. Accordingly, sequences that have about 85% to about 90%; or more preferably, about 91% to about 95%; or even more preferably, about 96% to about 99%; of nucleotides that are identical or functionally equivalent to one or more of the nucleotide sequences provided herein are particularly contemplated to be useful in the practice of the invention.

Suitable standard hybridization conditions for the present invention include, for example, hybridization in 50% formamide, 5×Denhardt's solution, 5×SSC, 25 mM sodium phosphate, 0.1% SDS and 100 µg/ml of denatured salmon sperm DNA at 42° C. for 16 h followed by 1 hr sequential washes with 0.1×SSC, 0.1% SDS solution at 60° C. to remove the desired amount of background signal. Lower stringency hybridization conditions for the present invention include, for example, hybridization in 35% formamide, 5×Denhardt's solution, 5×SSC, 25 mM sodium phosphate, 0.1% SDS and 100 µg/ml denatured salmon sperm DNA or *E. coli* DNA at 42° C. for 16 h followed by sequential washes with 0.8×SSC, 0.1% SDS at 55° C. Those of skill in the art will recognize that conditions can be readily adjusted to obtain the desired level of stringency.

Naturally, the present invention also encompasses nucleic acid segments that are complementary, essentially complementary, and/or substantially complementary to at least one or more of the specific nucleotide sequences specifically set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As described above, the probes and primers of the present invention may be of any length. By assigning numeric values to a sequence, for example, the first residue is 1, the second residue is 2, etc., an algorithm defining all probes or primers contained within a given sequence can be proposed:

n to n+y, where n is an integer from 1 to the last number of the sequence and y is the length of the probe or primer minus one, where n+y does not exceed the last number of the sequence. Thus, for a 25-basepair probe or primer (i.e., a "25-mer"), the collection of probes or primers correspond to bases 1 to 25, bases 2 to 26, bases 3 to 27, bases 4 to 28, and so on over the entire length of the sequence. Similarly, for a 35-basepair probe or primer (i.e., a "35-mer), exemplary primer or probe sequence include, without limitation, sequences corresponding to bases 1 to 35, bases 2 to 36, bases 3 to 37, bases 4 to 38, and so on over the entire length of the sequence. Likewise, for 40-mers, such probes or primers may correspond to the nucleotides from the first basepair to bp 40, from the second bp of the sequence to bp 41, from the third bp to bp 42, and so forth, while for 50-mers, such probes or primers may correspond to a nucleotide sequence extending from bp 1 to bp 50, from bp 2 to bp 51, from bp 3 to bp 52, from bp 4 to bp 53, and so forth.

In certain embodiments, it will be advantageous to employ one or more nucleic acid segments of the present invention in combination with an appropriate detectable marker (i.e., a "label,"), such as in the case of employing labeled polynucleotide probes in determining the presence of a given target sequence in a hybridization assay. A wide variety of appropriate indicator compounds and compositions are known in the art for labeling oligonucleotide probes, including, without limitation, fluorescent, radioactive, enzymatic or other ligands, such as avidin/biotin, etc., which are capable of being detected in a suitable assay. In particular embodiments, one may also employ one or more fluorescent labels or an enzyme tag such as urease, alkaline phosphatase or peroxidase, instead of radioactive or other environmentally less-desirable reagents. In the case of enzyme tags, colorimetric, chromogenic, or fluorigenic indicator substrates are known that can be employed to provide a method for detecting the sample that is visible to the human eye, or by analytical methods such as scintigraphy, fluorimetry, spectrophotometry, and the like, to identify specific hybridization with samples containing one or more complementary or substantially complementary nucleic acid sequences. In the case of so-called "multiplexing" assays, where two or more labeled probes are detected either simultaneously or sequentially, it may be desirable to label a first oligonucleotide probe with a first label having a first detection property or parameter (for example, an emission and/or excitation spectral maximum), which also labeled a second oligonucleotide probe with a second label having a second detection property or parameter that is different (i.e., discreet or discernable from the first label. The use of multiplexing assays, particularly in the context of genetic amplification/detection protocols are well-known to those of ordinary skill in the molecular genetic arts.

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

EXAMPLES

The following examples are included to demonstrate illustrative embodiments of the invention. It should be appreciated by those of ordinary skill in the art that the techniques disclosed in these examples represent techniques discovered to function well in the practice of the invention, and thus can be considered to constitute preferred modes for its practice. However, those of ordinary skill in the art should, in light of the present disclosure appreciate that many changes can be made in the specific embodiments which are disclosed and still obtain a like or similar result without departing from the spirit and scope of the invention.

Example 1—AAV Vector Library Construction

Methodologies to improve existing AAV vectors for gene therapy include either rational approaches or directed evolution to derive capsid variants characterized by superior transduction efficiencies in targeted tissues. In the present invention, both approaches were integrated in one unified design strategy of "virtual family shuffling" to derive a combinatorial capsid library whereby only variable regions on the surface of the capsid are modified. Individual sub-libraries were first assembled in order to pre-select compatible amino acid residues within restricted surface-exposed regions to minimize the generation of dead-end variants. Subsequently, the successful families were interbred to derive a combined library of about $1\times10^8$ complexity. Next-Gen sequencing of the packaged viral DNA revealed capsid surface areas susceptible to directed evolution thus providing guidance for future designs. The utility of the library in gene therapy applications by deriving an AAV2-based vector characterized by 20-fold higher transduction efficiency in murine liver, now equivalent to that of AAV8.

Experimental Methods

Experimental methods useful in the practice of the present invention may be found in the contemporary molecular genetics literature, and are well known to those of ordinary skill in the gene therapy arts. Detailed methods and protocols for the preparation and purification of AAV vectors may be found in U.S. Pat. No. 7,220,577 (specifically incorporate herein in its entirety by express reference thereto).

The CapLib-6 amino acid sequence of the AAV2 capsid showing altered positions in the library (X) is shown below:

(SEQ ID NO: 105)
MAADGYLPDWLEDTLSEGIRQWWKLKPGPPPPKPAERHKDDSRGLVLPGY

KYLGPFNGLDKGEPVNEADAAALEHDKAYDRQLDSGDNPYLKYNHADAEF

QERLKEDTSFGGNLGRAVFQAKKRVLEPLGLVEEPVKTAPGKKRPVEHSP

VEPDSSSGTGKAGQQPARKRLNFGQTGDADSVPDPQPLGQPPAAPSGLGT

NTMATGSGAPMADNNEGADGVGNSSGNWHCDSTWMGDRVITTSTRTWALP

TYNNHLYKQISSXXGXXNDNHYFGYSTPWGYFDFNRFHCHFSPRDWQRLI

NNNWGFRPKRLNFKLFNIQVKEVTQNDGTTTIANNLTSTVQVFTDSEYQL

PYVLGSAHQGCLPPFPADVFMVPOYGYLTLNXXXXAVGRSSFYCLEYFPS

QMLRTGNNFTFSYTFEDVPFHSSYAHSQSLDRLMNPLIDQYLYFLSRTNX

XXGXXTXSXLXFSQXXASDIRDQSRNWLPGPCYRQQRVSXXXXXNNNSXF

SWXGATKYHLNGRDSLVNPGPAMASHXDXXXXFFPQSGVLIFGKXXXXXX

XXXXXXXVMITDEEEIRTTNPVATEQYGSVSTNLQXXXXXAAXXXVXTQGV

LPGMVWQDRDVYLQGPIWAKIPHTDGHFHPSPLMGGFGLKHPPPQILIKN

TPVPANPSTTFSAAKFASFITQYSTGQVSVEIEWELQKENSKRWNPEIQY

TSNXXXXXXVXXTVDTNGVYSEPRPIGTRFLTRNL

The library was injected in the bloodstream of mice, and capsid DNA was amplified from the liver three days later and used to generate a new viral library. After three such rounds of in vivo selection, the following variants were obtained:

based on the knowledge of virus biology (Wu et al., 2000; Zhong et al., 2008; Lochric et al., 2005; Aslanidi et al., 2012; Li et al., 2012; Gabriel et al., 2013; Pandya et al., 2013; Sen et al., 2013; Aslanidi et al., 2013); and 2) utilizing a process of directed evolution, a high-throughput method of introducing molecular modifications into the AAV capsids, manipulating both diversity and selection in a vastly hastened emulation of natural evolution (Müller et al., 2003; Perabo et al., 2003; Maheshri et al., 2006; Michelfelder et al., 2007; Kwon and Schaffer, 2008; Li et al., 2008; Koerber et al., 2008; Li et al., 2009; Yang et al., 2009; (Koerber et al., 2009; Maguire et al., 2010; Gray et al., 2010; Jang et al., 2011: Yang et al., 2011; Asuri et al., 2012; Dalkara et al., 2013; Yang and Xiao, 2013). Although both methodologies have been successful in creating vectors with superior transduction capabilities, their utility is limited by an understanding of AAV life cycle, and by the technical boundaries of the protocols for directed evolution.

The strategy adopted in the present invention integrated both approaches into one unified design. Using detailed knowledge of known AAV capsid structures (Xie et al., 2002; Kaludov et al., 2003; Walters et al., 2004; Padron et al., 2005; Lane et al., 2005; DiMattia et al., 2005; Miller et al., 2006; Nam et al., 2007; Quesada et al., 2007; DiPrimio et al., 2008; Mitchell et al., 2009; Ng et al., 2010; Agbandje-McKennaand Kleinschmidt, 2011; DiMattia et al., 2012; Govindasamy et al., 2013) and the sequence of 150 naturally-occurring variants, a process of "virtual family shuffling" in silico has been conducted to derive a combinatorial capsid library whereby only variable regions on the surface of the structure are modified.

The utility of the resulting library was demonstrated by enhancing the transduction of murine liver by 20-fold with

| Loop | I | 444 | IV | V | clones | subst | (SEQ ID NOS) |
|---|---|---|---|---|---|---|---|
| AAV2 | SQSGASN | Y | NTPSGTTTQSRLQFSTSADNNNSEYSWTGATKYH | | | | (SEQ ID NO: 106) |
| LI-A | SASGASN | F | NSEGGSLTQSSLGFSTDGENNNSDFSWTGATKYH | | 21 | 14 | (SEQ ID NO: 107) |
| LI-B | SQSGASN | Y | NTPSGTTTQSRLQFSTDGENNNSDFSWTGATKYH | | 4 | 5 | (SEQ ID NO: 108) |
| LI-C | SASGASN | Y | NTPSGTTTQSRLQFSTSADNNNSEFSWPGATTYH | | 3 | 4 | (SEQ ID No: 109) |
| LI-D | SQSGASN | F | NSEGGSLTQSSLGFSTDGENNNSDFSWTGATKYH | | 3 | 13 | (SEQ ID NO: 110) |
| LI-E | SASGASN | Y | NTPSGSLTQSSLGFSTDGENNNSDFSWTGATKYH | | 2 | 10 | (SEQ ID NO: 111) |
| LI-F | SQSGASN | Y | NTPSGTTTQSRLQFSTSADNNNSDFSWTGATKYH | | 2 | 2 | (SEQ ID NO: 112) |
| LI-G | SGAGASN | F | NSEGGSLTQSSLGFSTDGENNNSDFSWTGATKYH | | 2 | 15 | (SEQ ID NO: 113) |

Example 2—Integrating Combinatorial and Rational Approaches to Derive Novel AAV Variants AAV is a single-stranded DNA virus belonging to the Parvoviridae family (Muzyezka and Berns, 2001). AAV-derived vectors are promising tools for human gene therapy applications because of their absence of pathogenicity, episomal localization and stable transgene expression (Wu et al., 2006). However, significant limitations to the clinical use of AAV are its promiscuity and its susceptibility to neutralization by human antibodies (Louis-Jeune et al., 2013). Both of these limitations are determined by the nature of amino acid residues exposed at the surface of the capsid. Two main strategies are generally employed to improve AAV vectors: 1) mutagenizing capsid residues to facilitate binding, entry, and/or intracellular trafficking through a rational approach an AAV2-derived vector containing only four mutations—a combination of rational mutagenesis and directed evolution.

Materials and Methods

Library Construction.

The library was built in two steps: first, individual VR lineages (each with mutations in only one or two variable regions) were derived, selecting for amino acid combinations compatible with capsid assembly; then, structurally-compatible sequences were combined to generate the final library. DNA fragments were synthesized by Degenerate Homoduplex Gene Family Recombination (DHGFR) as described previously (Coco et al., 2002):

Fragments were assembled by Enzymatic Ligation Assisted by Nucleases (ELAN) as described (Cost and Cozzarelli, 2007). Fragments for the six individual VR lineages were generated by overlap extension (Horton et al., 1989) of PCR products derived from pSub201 (Samulski et al., 1987) for the wild-type regions and from DHGFR products (or from the ELAN product if no suitable DHGFR template was available) for the variable regions. The assembled fragments were inserted into linearized pSubEagApa (a pSub201 derivative containing a deletion between ApaI sites at 3764 and 4049 and including an EagI site at position 4373, a silent mutation, thus allowing reconstitution of a full-length cap gene after insertion of a fragment between the ApaI and EagI sites), using isothermal DNA assembly (Gibson et al., 2009). Viral libraries were generated as previously described (Maheshri et al., 2006) except that HEK 293 cells were co-transfected with 10 ng of the library plasmid and 70 µg of pHelper (a molar ratio of 1:5000) for each 15-cm dish. AAV was purified using iodixanol gradient (Zolotukhin et al., 1999) and titered by qPCR using primers specific to the rep gene (forward: 5'-GCAAGACCGGATGTTCAAAT-3' (SEQ ID NO:165), reverse: 5'-CCTCAACCACGTGATCCTT-3', (SEQ ID NO: 166). In order to generate the final library, overlapping fragments containing variable regions were amplified from purified DNA isolated from the individual viral libraries, and assembled using overlap extension. The product was inserted into linearized pSubEagApa as described above. The final viral library was generated, purified and quantified as described above.

Library Sequencing.

Purified viral DNA was amplified using the following primers:

5'-CAACCACCTCTACAAACAAATTTCCAG-3' (SEQ ID NO: 167) and

5'-CACGCCATTAGTGTTCCACAG-3' (SEQ ID NO: 168) as forward and reverse, respectively.

The resulting amplification product was gel-purified. It was then processed at the UF ICBR NextGen core laboratory on a PacBio RS instrument using one SMRT cell. In order to analyze the data, dedicated code was written using the Python 2.7 programming language. The code interpreted the original fastq file containing the CCS reads, corrected reads by aligning them to a reference sequence, translated the corrected reads into protein sequences, and then analyzed the results. Despite a high occurrence of sequencing errors, useful reads could be recovered, because most of the capsid sequence is conserved, and only the sequences in the variable regions are needed.

In this example, the variable regions included 182 nucleotides out of 1399. The corrected reads generated by caplib were therefore derived from the CCS reads that likely had no errors in the variable regions (exact match with the reference sequence, including the ambiguous nucleotides). Obviously, this approach excludes all reads with possible insertions or deletions in the variable regions, and ignores any possible variation in the conserved regions.

In Vivo Selection.

In each round of the in vivo selection approach, 2 male C57BL/6J mice, 8 to 10 weeks old, were injected with $1\times10^{10}$ to $1\times10^{11}$ vg of viral preparation (original library for the first round, target-enriched libraries in subsequent rounds) via the tail vein. Mice were euthanized 3 to 4 days later by cervical dislocation after being anesthetized with isoflurane. Episomal DNA was purified from harvested livers using modified Hirt DNA extraction (Arad, 1998) and used as template to amplify capsid DNA sequences using the following primers:

```
                                      (SEQ ID NO: 169)
forward: 5'-GGATGGGCGACAGAGTCATC-3'
and (SEQ ID NO: 170)
reverse: 5'-CAAGCAATTACAGATTACGAGTCAGG-3'
```

After gel-purification, amplification products were inserted into linearized pSubEagApa as described above. Liver-enriched libraries were then generated, purified and quantified as described above. After the third round of selection, amplified capsid DNA was inserted into linearized pACG2-m56, a vector derived from pACG-2 (Li et al., 1997) with the same modifications as pSubEagApa (deletion between two ApaI sites and introduction of an EagI site allowing cloning of amplified capsid fragments between the ApaI and EagI sites). Random clones were then analyzed by sequencing.

Luciferase Expression.

HEK 293 cells were co-transfected with selected capsid variants in pACG2-m56, luciferase-expressing barcoded vector pTR-UF50-BC (GenBank accession #KF926476) and pHelper in equimolar amounts, in a separate transfection for each variant. Each capsid variant was therefore physically linked to a different sequence identifier (barcode). Resulting transgenic AAVs were purified and quantified as described above, except that primers specific to the CBA promoter were used for qPCR:

```
                                      (SEQ ID NO: 171)
forward: 5'-TCCCATAGTAACGCCAATTAGG-3'

(SEQ ID NO: 172)
reverse: 5'-CTTGGCATATGATACACTTGATG-3'
```

An equimolar mixture (calculated from the qPCR-derived titers) was used as template to amplify the barcode region, which was then added to an IonTorrent sequencing reaction. Precise relative titering was achieved by quantifying barcodes specific to each variant. Nine-weeks-old male BALB/c mice (Charles River Laboratories) were injected via tail-vein with $1\times10^{11}$ vg (according to barcode-corrected titers) of viral preparation, three mice for each variant. Luciferase expression was monitored every 5 days during 40 days on a Xenogen IVIS imaging system 10 to 12 min after intra-peritoncal injection of 150 µg luciferin per g of body weight.

Barcode Sequencing.

Sequencing of barcoded DNA was performed at the UF ICBR NextGen core laboratory using an IonTorrent PGM system. Samples were amplified using the following barcoded primers:

```
forward:
                                      (SEQ ID NO: 173)
5'-CCATCTCATCCCTGCGTGTCTCCGACTCAGNNGGACGAGCTGTACAA
GTAAATCG-3'
and reverse:
                                      (SEQ ID NO: 174)
5'-CCTCTCTATGGGCAGTCGGTGATNNCCATTATAAGCTGCAATAAACA
AG-3'
``` where "NN" designates a unique sequence. Each read therefore contains 3 barcodes: one identifying the capsid variant, located in the template, and two identifying the tissue sample, located in the primers. Sequencing data was analyzed by dna-barcode, a dedicated script written in Python 2.7.

hFIX Expression.

Viral vectors containing either AAV8 or LiC capsid and ApoE-hAAT-hF9 vector (Manno et al., 2006) were produced as described above. Male C57BL/6 mice (Jackson Laboratories), 6 to 8 weeks old, were injected in the tail vein with $1\times10^{10}$ vg of either preparation, 4 mice for each vector. Injected mice were followed for three months and bled monthly from the retro-orbital plexus using heparinized microcapillary tubes. Plasma levels of hFIX antigen were measured by ELISA as published (Mingozzi et al., 2003; Cao et al., 2009).

Biodistribution.

An equimolar mixture of viral preparations of barcoded capsid variants was tail vein-injected into three 9-weeks-old male BALB/c mice (Charles River Laboratories), at a dose of $2\times10^1$ vg per mouse. Mice were euthanized 3 weeks later as described above. Total DNA was isolated from tissue samples and quantified. Occurrence of AAV genomes in tissues was quantified by qPCR using primers specific to the CBA promoter as described above. Relative amounts of the various capsid variants in each sample were calculated from barcode sequencing data.

Results

Library Design.

Structural comparison of the AAV capsid protein among various serotypes has revealed highly homologous sequences interspersed with more evolutionary divergent areas. These amino acid stretches are commonly designated as variable regions I through IX (VRs, also known as "loops") (Govindasamy et al., 2006). Incidentally, VRs are localized at the surface of the assembled capsid and are assumed to be responsible for the interaction with cell surface receptors and other host factors. Because of their location, VRs are also predicted to be less critical for capsid assembly. Therefore, the guiding principle of the library's design was to modify only surface VRs while keeping the backbone sequence unchanged to maintain the integrity of the assembling scaffold. All candidate positions for mutagenesis were selected from the alignment of 150 AAV naturally-occurring variants, and then evaluated on a 3D model of the AAV2 capsid (Xie et al., 2002).

Only those residues which were clearly exposed to the surface were selected for modification. To reduce the incidence of discordant residues, the selection of the introduced substitutions was restricted to those appearing in a given position in at least one from the analyzed 150 homologues. Adding to the rational design strategy, four more positions were modified: surface Y444F and Y500F to increase the transduction efficiency (Zhong et al., 2008) and surface R585F and R588F to de-target binding to heparan sulfate proteoglycan (Opie et al., 2003), the primary receptor for AAV2 (Summerford and Samulski, 1998).

Detailed composition of each variable region, including nucleotide sequence and resulting amino acid diversity, is shown in the accompanying figures. To achieve the desired composition, in some cases more than one nucleotide needed to be changed per codon, resulting in additional amino acid diversity. The AAV2 capsid gene fragment incorporating all substitutions was assembled from synthetic oligonucleotides and inserted into a plasmid vector containing the AAV2 genome from which the corresponding WT sequence had been removed.

The plasmid library, with an estimated complexity of $1\times10^8$, was analyzed by sequencing random clones and was found to reflect accurately the library's design, including expected nucleotide substitutions positions and types. This highly representative plasmid library, however, failed to produce packaged virus of higher titer. An apparent explanation was the presence of an alternative open reading frame (ORF) coding for the assembly-activating protein (AAP) (Sonntag et al., 2010). As the AAP ORF overlaps with coding regions for VRs I and II, their mutagenesis would potentially interfere with AAP structure and function, likely preventing many capsid variants from being assembled. Disruption of AAP, however, was not the only reason for the low viral library complexity from the initial design. Apparently, the high diversity rendered the library non-functional as some of the substitutions were incompatible within the context of the 3D structure. For example, both plasmid and encapsidated viral DNA showed the expected complexity when a single VR-III library was packaged, with all variable positions incorporating nucleotides as designed (CapLib3A). However, when the same VR-III was combined with VR-IV through VR-VIII plasmid libraries, the packaged virions incorporated mostly WT AAV2 genomes despite having expected diversity at the plasmid level (CapLib3B). Apparently, the presence of a multitude of simultaneous substitutions increased the likelihood of combinations that are incompatible with capsid folding and/or assembly, resulting in a dramatic decrease in the fraction of viable variants.

Structural Compatibility as a Selection Trait.

As single VRs libraries appeared to produce both expected diversity and high titer viral stocks, a new strategy was undertaken to generate as much diversity as possible by selecting for compatibility with capsid folding for each individual VR. The recovered encapsidated viral DNAs were then used to create a final library by combining preselected structure-compatible variants. After sequence analysis of the constructed individual libraries, the viral DNA revealed no diversity (WT sequence only) in VR-II (as expected due to the overlapping AAP ORF), low diversity in VRs III and VI, and high diversity in all other VRs. The sequences from these VR lineages were then combined to generate the final library. The resulting sequence includes 136 degenerate positions and encodes 59 variable amino acid positions, each with 2 to 16 permutations resulting in a theoretical complexity (total number of possible amino acid combinations) of $4\times10$ (Govindasamy et al., 2006). Three-dimensional models of the VP3 monomer and the assembled capsid were rendered with variable amino acid positions colored according to VR identity.

A plasmid library was generated, with an estimated complexity of $9.2\times10^7$, as deduced by extrapolating colony counts and correcting for positive clones. Its quality was assessed by sequencing a random sample of 21 clones where all corresponding 21 protein sequences were found to be unique. Each differed from the reference AAV2 sequence by 24 to 41 amino acid substitutions. Substitutions were distributed among five to seven VRs per sequence. VRs II and III were WT in all cases. Because of the assembly procedure, positions 444 and 500 exhibited Y/F polymorphism, with 1/21 and 8/21 containing WT Tyr residues in the respective positions.

Viral Library Characterization.

Extrapolating colony counts and sequencing random individual clones always overestimates the library complexity because a fraction of the variant genomes fails to form viable capsids. To assess the library's complexity under more stringent conditions, the encapsidated viral DNA was subjected to Next-Gen sequencing. The distance between VRs, as well as their small size, would not allow accurate reconstruction of full-length sequence contigs from short reads. Therefore, despite its lower throughput and high error rate, the PacBio Circular Consensus Sequencing (CCS) platform was selected as the one with a compatible read length most suited for the current methodology. Because no software support existed to analyze the resulting dataset, the inventors also was developed a dedicated code (caplib) to process and analyze sequencing data. From the 19,455 original CCS reads, the caplib software generated a list of 840 corrected reads and translated them into protein sequences analyzed as described above.

As a convenient way of illustrating the complexity of each permutated VR, Shannon entropy (Shannon et al., 1948) was computed from an alignment of the 840 individual protein sequences. As the data revealed, entropy was highest in VRs I, IV and VII, moderate in VRs V, VI and VIII, very low in VR IX and almost non-existent in VR III. A comparison of the 840 protein sequences identified 699 distinct sequences, including 41 which were present in more than one copy. Each sequence had up to 43 mutations (substitutions), with an average of 19.16.

VRs III, VIII and IX were completely WT, which suggested that these regions may be most sensitive to changes affecting the efficiency of virion assembly. Interestingly, the consensus sequence itself was not identified among the 840 analyzed sequences.

Amino acid composition at each variable position was determined. Although some level of diversity is visible at most positions (only position 383 has a single identity), in many cases a single amino acid is predominant. However, 14 positions in which no single variant occurs in more than 50% of the sequences can be found, in VRs I (position 263), IV (450 to 461) and VII (548 to 550, 555 and 556).

The observed complexity of variable amino acid positions compared to theoretical values was also calculated. Experimental complexities vary between 1 and 14 with an average of 5.93, compared to a range of 1 to 16 and an average of 6.79 for theoretical complexities. Only position 383 has an observed complexity of 1, probably the result of sampling bias as only 14 sequences out of 840 have a mutation in VR III. Complexities of the eight variable regions were also computed as well (see Table 1).

TABLE 1

AMINO ACID COMPLEXITY IN CAPLIB VARIABLE REGIONS

| Variable Region | Theoretical Complexity from Design | Theoretical from Observed Amino Acid Complexity | Maximum Possible Complexity in the Sample | Experimental Complexity | Number of Single-Copy Sequences |
|---|---|---|---|---|---|
| Loop I    | 288               | 396               | 396 | 76  | 23  |
| Loop III  | 168               | 12                | 12  | 6   | 3   |
| Loop IV   | $7.6 \times 10^8$ | $4.8 \times 10^8$ | 699 | 247 | 169 |
| Loop V    | $7.4 \times 10^4$ | $1.4 \times 10^4$ | 699 | 47  | 29  |
| Loop VI   | $2.7 \times 10^3$ | $2.0 \times 10^3$ | 699 | 89  | 45  |
| Loop VII  | $2.4 \times 10^8$ | $1.1 \times 10^8$ | 699 | 197 | 135 |
| Loop VIII | $9.7 \times 10^8$ | $8.0 \times 10^8$ | 699 | 122 | 110 |
| Loop IX   | $2.4 \times 10^6$ | $3.8 \times 10^5$ | 699 | 18  | 12  |

The frequency distribution and interdependence of mutagenized VRs revealed a majority (75%) of sequences have mutations in three to five VRs (average 3.76). Almost half of the sequences (414 or 49.3%) have one of the three mutant VR combinations I-IV-V-VII (179), I-IV-V-VI-VII (134) or I-IV-VII (101). Two thirds of the sequences (557 or 66.3%) have mutations in the 3 VRs 1, IV and VII. Over 4/5 (677 or 80.6%) have mutations in at least VRs I and IV.

A comparison of expected and observed—both in the plasmid and viral libraries—percentages of mutant residues at each variable amino acid position is shown in the accompanying figures. Comparing theoretical and plasmid libraries shows the effect of mutations in individual VRs on virion assembly, as the combined plasmid library was constructed from packaged viral DNA originating from individual VR libraries. Mutations in VRs IV, VI and VIII alone seem not to interfere significantly with capsid assembly, while mutations in VRs III and IX are strongly selected against. Comparing plasmid and viral libraries allows us to evaluate the effect of combining multiple mutated VRs. Mutant VRs I, IV and V seem to tolerate well additional mutations in other VRs (very little difference can be seen between numbers from plasmid and viral libraries), unlike VR VIII, and to a lesser extent VRs VI, VII and IX.

A consensus of the 840 sequences was aligned with the nine sequences that were found in more than four copies (only regions with mutations are displayed). In all cases, Interestingly, they were, in most cases, much smaller than expected. It appears that very few combinations were compatible with capsid assembly, or that different combinations resulted in dramatic differences in assembly efficiency, in effect reducing complexity at the VR level. Note however, that actual VR complexities were probably much higher than observed in the sample, as many sequences occurred as single copies. As for the complexity of the exemplary library itself, the small sample size did not permit its determination with confidence. The total number of possible VR combinations, however, based on the observed complexities (which are underestimated as explained above) is $2.0 \times 10^{14}$. Applying the lowest observed to expected ratio obtained with amino acid combinations in VRs (18/699) would give $5.0 \times 10^{12}$, still a much higher number than the limit of $9.2 \times 10^7$ described above. That limit needs to be adjusted according to the ratio between observed complexity and sample size (699/840). Therefore, an upper limit of $7.7 \times 10^7$ could be confidently estimated for the complexity of the library.

In Vivo Selection of Liver-Targeted AAV Variants.

Liver is an important gene therapy target to treat many inherited disorders (Sands, 2011; Sharland et al., 2010). Several serotypes target liver preferentially, with the highest transduction efficiency shown by AAV8 (Gao et al., 2002; Nakai et al., 2004) in murine liver, with expression levels two orders of magnitude higher than those of AAV2. However, this does not translate to primates, in which the efficiency of AAV8 is dramatically lower (Hurlbut et al., 2010), although AAV8 is still being considered one of the best candidate vectors for human liver-directed gene therapy. Because AAV2 was used as the library's backbone, we asked whether a novel capsid variant could be isolated targeting the liver with an efficiency comparable to that of AAV8.

TABLE 2

LOSS OF DIVERSITY DURING FINAL LIBRARY VIRUS PRODUCTION ESTIMATED FROM VARIATIONS IN THE OCCURRENCE OF MUTANT AMINO ACID POSITIONS WITHIN VARIABLE REGIONS

| VR | Average % mutant positions in plasmid library | Average % mutant positions in viral library | Ratio |
|---|---|---|---|
| I + VI | 59.3 | 33.2 | 0.56 |
| III + V | 25.8 | 22.6 | 0.88 |
| IV | 70.6 | 59.2 | 0.84 |
| VII | 64.3 | 46.8 | 0.73 |
| VIII | 89.4 | 12.1 | 0.14 |
| IX | 11.3 | 2.8 | 0.25 |
|  |  | Product | 0.010 |

After three rounds of in vivo selection, 41 clones were sequenced, and an alignment of the recurrent sequences' variable regions was generated. None of the 7 liver-selected sequences could be found among the 840 translated sequence reads, which indicates that their abundance in not the result of a pre-existing prevalence in the original library, but is most likely the result of genuine selection. Interestingly, the K507T substitution in LiC was not included into the library's design. A comparison of motif enrichments in the liver-selected variants is summarized in Table 3.

TABLE 3

MOTIF ENRICHMENT IN SEQUENCED LIVER-SELECTED VARIANTS

| Region | Motif | CapLib | Liver-Targeted Variants |
|---|---|---|---|
| 262-268 | SASGASN (SEQ ID NO: 175) | 56/840 (6.7%) | 26/41 (63.4%) |
| 262-268 | SGAGASN (SEQ ID NO: 176) | 18/840 (2.1%) | 2/41 (4.9%) |
| 449-463 | NSEGGSLTQSSLGFS (SEQ ID NO: 177) | 3/840 (0.4%) | 26/41 (63.4%) |
| 491-501 | TDGENNNSDFS (SEQ ID NO: 178) | 299/840 (35.6%) | 32/41 (78.0%) |
| 498-506 | SEFSWPGATT (SEQ ID NO: 179) | 23/840 (2.7%) | 4/41 (9.8%) |
| 507 | T | 0/840 (0.0%) | 4/41 (9.8%) |
| 491-503 | TSADNNNSDFSWT (SEQ ID NO: 180) | 77/840 (9.2%) | 2/41 (4.9%) |

Bold characters in motifs indicate amino acid substitutions (compared to the AAV2 reference). The 2 columns on the right show the motif occurrences in the library sequencing sample (CapLib) and in the sequenced liver-selected variants.

Motifs with the highest enrichment are SASGASN (SEQ ID NO:175) in VR I, NSEGGSLTQSSLGFS (SEQ ID NO:177) in VR IV and SEFSWPGATT (SEQ ID NO:179) in VR V, suggesting that variants LiA and LiC were the most strongly selected.

Characterization of Liver-Selected Variants LiA and LiC.

Variant capsids LiA and LiC, as well as controls AAV2 and AAV8, were packaged with luciferase-expressing barcoded vector pTR-UF50-BC. The dynamics of luciferase expression in the liver were considerably different for all serotypes and variants: AAV8 mediated a fast initial increase followed by a slow leveling off. LiA followed a similar trend at a lower level of expression. LiC, on the other hand, provided steady gain converging with the levels of AAV8 after about 30 days. At day 40, the AAV8 and LiC-mediated luciferase expression exceeded that of AAV2 by 20-fold. Consistent with luciferase expression, hFIX transgene expression driven by ApoE-hAAT promoter followed the same pattern showing similar efficiencies for AAV8 and LiC, and a two-fold lower efficiency for LiA.

TABLE 4

SYNTHETIC OLIGONUCLEOTIDES USED TO ASSEMBLE THE ORIGINAL CAPSID LIBRARY

| DESIGNATION | NUCLEIC ACID SEQUENCE | SEQ ID NO: |
|---|---|---|
| 1TS1 | CCTGGGCCCTGCCCACCTACAACAACCACCT | (SEQ ID NO: 114) |
| 1TS2 | CTACAAACAAATTTCCAGCVVMDCAGGARSCASCAACGACAATCACTACTTTGGCTACAG | (SEQ ID NO: 115) |
| 1TS3 | CACCCCTTGGGGGTATTTTGACTTCAACAGATTCCACTGCCACTTTTCACCACGGGACTG | (SEQ ID NO: 116) |
| 1TS4 | GCAAAGACTCATCAACAACAACTGGGGATTCCGCCCCAAGAGACTCAACTTCAAGCTCTT | (SEQ ID NO: 117) |
| 1TS5 | TAACATTCAAGTCAAAGAGGTCACAMMGMRSRRSRGCRHGAMGACAATTGCCAATAACCT | (SEQ ID NO: 118) |
| 1TS6 | TACCAGCACAGTTCAGGTGTTTACTGACTCTGAGTACCAGCTCCCATACGTCCTCGGCAG | (SEQ ID NO: 119) |
| 1TS7 | CGCGCATCAAGGATGCCTCCCACCCTTCCCAGCAGACGTCTTCATGATGCCAC | (SEQ ID NO: 120) |
| 2TS1 | GTCTCCATGGTGCCACAGTATGGATACCTCACCCTGAACRACRRSMRSMAGGCAGTCGGACGC | (SEQ ID NO: 121) |
| 2TS2 | TCTTCATTTTACTGCCTGGAGTACTTTCCTTCTCAGATGCTGCGCACCGGAAAC | (SEQ ID NO: 122) |

TABLE 4-continued

SYNTHETIC OLIGONUCLEOTIDES USED TO ASSEMBLE THE ORIGINAL CAPSID LIBRARY

| DESIGNATION | NUCLEIC ACID SEQUENCE | SEQ ID NO: |
|---|---|---|
| 2TS3 | AACTTTACCTTCAGCTACACTTTTGAGGACGTTCCTTTCCACAGCAGCTACG | (SEQ ID NO: 123) |
| 2TS4 | CTCACAGCCAGAGTCTGGACCGCCTGATGAATCCTCTCATCGACCAGTACCTGTA | (SEQ ID NO: 124) |
| 2TS5 | TTTCTTGAGCAGAACAAACRVCVVSRSCGGAMNCVHSACCMHSTCAVVSCTTVDSTTTTCTCAGSBC RGSGCGAGTGACA | (SEQ ID NO: 125) |
| 2TS6 | TTCGGGACCAGTCTAGAAAC | (SEQ ID NO: 126) |
| 3TS1 | CAGCCTAGGAACTGGCTTCCTGGACCCTGTTACCGCCA | (SEQ ID NO: 127) |
| 3TS2 | GCAGAGAGTCTCAAMAMMAVNSRVCSRSAACAACAACAGTRASTTCTCCTGGMMAGGAGC | (SEQ ID NO: 128) |
| 3TS3 | TACCAAGTACCACCTCAATGGCAGAGACTCTCTGGTGAATCCCGGACC | (SEQ ID NO: 129) |
| 3TS4 | AGCTATGGCAAGCCACRRGGACRRCRMSRRSARSTTTTTTCCTCAGAGCGGGGTTCTCA | (SEQ ID NO: 130) |
| 3TS5 | TCTTTGGGAAGSAARRCRSCRVSRVARVCRATRYCGMSNHCRVMVRSGTGATGATTACAGACGAAGA GGAGATCTGGAC | (SEQ ID NO: 131) |
| 4TS1 | GAAGAGGTGATCAGGACAACCAATCCCGTGGCTACAGAGCAGTATGGTTCT | (SEQ ID NO: 132) |
| 4TS2 | GTCTCTACCAACCTCCAGVVSVVSMRSRVCVNSGCAGCTDHCVVSRNSGTCVMSACACAAGGCGTTC TTC | (SEQ ID NO: 133) |
| 4TS3 | CAGGCATGGTCTGGCAGGACAGAGATGTGTACCTTCAGGGACCCATCTGGGCA | (SEQ ID NO: 134) |
| 4TS4 | AAGATTCCACACACAGACGGACATTTTCACCCCTCTCCCCTCATGGGTGGATTCG | (SEQ ID NO: 135) |
| 4TS5 | GACTTAAACACCCTCCTCCACAGATTCTCATCAAGAACACCCCGTACGTGC | (SEQ ID NO: 136) |
| 5TS1 | ACCCCGGTACCTGCGAATCCTTCTACCACCTTCAGTGCGGCAAAGTTTG | (SEQ ID NO: 137) |
| 5TS2 | CTTCCTTCATCACACAGTACTCCACAGGACAGGTCAGCGTGGAGA | (SEQ ID NO: 138) |
| 5TS3 | TCGAGTGGGAGCTGCAGAAGGAAAACAGCAAACGCTGGAATCCCGA | (SEQ ID NO: 139) |
| 5TS4 | AATTCAGTACACTTCCAACTWCRVSVSASMVSVHSDDTGTGSWSTKSACTGTGGACACTAATGGC | (SEQ ID NO: 140) |
| 5TS5 | GTGTATTCAGAGCCTCGGCCGATTG | (SEQ ID NO: 141) |
| 1PS1 | GCTGGAAATTTGTTTGTAGAGGTGGTTGTTGTAGGTG | (SEQ ID NO: 142) |
| 1PS2 | CCCCCAAGGGGTGCTGTAGCCAAAGTAGTGATT | (SEQ ID NO: 143) |
| 1PS3 | GTTGTTGATGAGTCTTTGCCAGTCCCGTGGTGAAA | (SEQ ID NO: 144) |
| 1PS4 | CCTCTTTGACTTGAATGTTAAAGAGCTTGAAGTTGAGTCT | (SEQ ID NO: 145) |
| 1PS5 | ACCTGAACTGTGCTGGTAAGGTTATTGGCAATTGTC | (SEQ ID NO: 146) |
| 1PS6 | ATCCTTGATGCGCGCTGCCGAGGACGTATG | (SEQ ID NO: 147) |
| 2PS1 | CAGGCAGTAAAATGAAGAGCGTCCGACTGCCT | (SEQ ID NO: 148) |
| 2PS2 | AGTGTAGCTGAAGGTAAAGTTGTTTCCGGTGCGC | (SEQ ID NO: 149) |
| 2PS3 | CCAGACTCTGGCTGTGAGCGTAGCTGCTGTGGAA | (SEQ ID NO: 150) |
| 2PS4 | GTTTGTTCTGCTCAAGAAATACAGGTACTGGTCGATGA | (SEQ ID NO: 151) |
| 2PS5 | TCTAGACTGGTCCCGAATGTCACTCGCSCYG | (SEQ ID NO: 152) |
| 3PS1 | TKKTKTTGAGACTCTCTGCTGGCGGTAACAGGGT | (SEQ ID NO: 153) |
| 3PS2 | ATTGAGGTGGTACTTGGTAGCTCCTKKCCAGGAGA | (SEQ ID NO: 154) |
| 3PS3 | GTGGCTTGCCATAGCTGGTCCGGGATTCACC | (SEQ ID NO: 155) |
| 3PS4 | GYYTTSCTTCCCAAAGATGAGAACCCCGCTCT | (SEQ ID NO: 156) |
| 4PS1 | CTGGAGGTTGGTAGAGACAGAACCATACTGCTCTGTAG | (SEQ ID NO: 157) |
| 4PS2 | GCCAGACCATGCCTGGAAGAACGCCTTGTGT | (SEQ ID NO: 158) |

TABLE 4-continued

SYNTHETIC OLIGONUCLEOTIDES USED TO ASSEMBLE THE ORIGINAL CAPSID LIBRARY

| DESIGNATION | NUCLEIC ACID SEQUENCE | SEQ ID NO: |
|---|---|---|
| 4PS3 | CGTCTGTGTGTGGAATCTTTGCCCAGATGGGTC | (SEQ ID NO: 159) |
| 4PS4 | GAGGAGGGTGTTTAAGTCCGAATCCACCCATGAG | (SEQ ID NO: 160) |
| 5PS1 | GTACTGTGTGATGAAGGAAGCAAACTTTGCCGCAC | (SEQ ID NO: 161) |
| 5PS2 | GCAGCTCCCACTCGATCTCCACGCTGACCTG | (SEQ ID NO: 162) |
| 5PS3 | AGTTGGAAGTGTACTGAATTTCGGGATTCCAGCG | (SEQ ID NO: 163) |
| 5PS4 | CCGAGGCTCTGAATACACGCCATTAGTGTCCACAGT | (SEQ ID NO: 164) |

Mice were euthanized 42 days after injection to examine biodistribution of viral genomes in various tissues and organs. Total DNA was isolated from samples, quantitated and used as template for qPCR to determine viral genome copy numbers.

DISCUSSION

Recent advances in clinical trials involving AAV vectors, concomitant with a more favorable regulatory climate, stimulated efforts to derive vehicles with higher transduction efficiencies, higher target tropism, and lower immunogenicity. One of the most prolific approaches so far has been the isolation of novel AAV serotypes. In spite of its apparent success, characterization of new serotypes, one at a time, is very laborious. An alternative methodology has been to generate combinatorial capsid libraries of high complexity in hope to randomly create a new variant meeting the demands of a particular application. However, the various strategies available to generate capsid libraries suffer from sequence bias or limited diversity. Finally, a rational approach of mutagenizing amino acid residues based on understanding of the capsid structure may have its practical limits, as many favorable mutations apparently cannot be combined to produce additive effects (Aslanidi et al., 2013). In the present example, all three strategies (utilizing naturally existing serotypes, applying directed evolution, and rational mutagenesis) were developed in one unified approach to greatly improve the availability of AAV vectors for use in gene therapy and related methodologies.

A bioinformatic analysis of the existing sequence database of 150 AAV naturally-occurring variants was used to create a consensus AAV capsid template whereby nine variable regions incorporated alternative residues present in a given position in at least one of the serotypes. This in silico-derived algorithm was converted into a combinatorial plasmid DNA library using the only feasible approach—de novo DNA synthesis. Even though the plasmid library was found to reflect faithfully the initial design, a new selection trait of 3D structural compatibility had to be introduced to isolate structurally sound variants within each individual VR. Subsequently, the successful families were interbred to derive a combined viral library of about 1×10 complexity, which was characterized in depth using Next-Gen sequencing.

The utility of the library was demonstrated by reiterative selection of an AAV2 variant (LiC) targeting murine liver with a 20-fold enhanced efficiency while differing from the WT parent by only four capsid residues. All mutations in both liver-specific variant that were analyzed are located in known antigenic sites for the AAV capsids and regions that control tissue transduction. Residue 263 in VR-I is within the binding site of the A20 monoclonal antibody (Lochrie et al., 2005), and within the ADK1b footprint on AAV1. This region is also known to control transduction (Lochrie et al., 2005). The Q263A mutation is also one of the mutations in AAV2.5, the muscle tropic vector derived from AAV2 (Bowles et al., 2011). The VR-V residues are within the ADKla footprint on AAV1 and the 4E4 footprint on AAV1 (Gurda et al., 2013). Residues 490-500 are within the C37B footprint on AAV2 and 5H7 footprint on AAV1 (Gurda et al., 2013), and have been reported to affect liver tropism in AAV9 (Pulicherla et al., 2011).

The stepwise approach for the library's construction, as well as the Next-Gen sequencing of encapsidated viral genomes, was helpful in understanding the structural requirements of each individual VR for the whole capsid integrity. For example, a nucleotide sequence coding for VR-II, as it is overlapping with AAP ORF, appears to be critical, and cannot be mutagenized. VRs III and IX showed a low complexity value, indicating the importance of these regions for capsid structure. The residues in these VRs are closest to the 2-fold axis, which was shown to be important for assembly (Naumer et al., 2012). On the other hand, VRs I, IV and VII are the most tolerant and substitutions of their residues are compatible with mutations in other VRs. Sterically, VR-I is raised on the capsid and is not interacting with other monomers; VR-IV protrudes the furthest from the surface and only the base of this VR is interacting with other VP monomers. VRs I, IV, VII, V and VI have the highest content of mutant positions, while VRs III, IX and, to a lesser extent, VIII are mostly invariable, consistent with previous reports (Ng et al., 2010). These data provide a clear guidance for the design of next generation capsid libraries with an even higher complexity whereby structural compatibility of particular VRs may be successfully utilized as an indispensable selection trait.

REFERENCES

The following references, to the extent that they provide exemplary procedural or other details supplementary to those set forth herein, are specifically incorporated herein in their entirety by express reference thereto:

U.S. Pat. No. 7,220,577 to Zolotukhin.

Agbandje-McKenna, M, and Kleinschmidt, J, "AAV capsid structure and cell interactions," *Methods Mol. Biol.* (Clifton, N.J.), 807:47-92 (2011).

Arad, U, "Modified Hirt procedure for rapid purification of extrachromosomal DNA from mammalian cells," *BioTechniques.* 24:760-762 (1998).

Aslanidi, G V et al., "High-efficiency transduction of human monocyte-derived dendritic cells by capsid-modified recombinant AAV2 vectors," *Vaccine*, 30:3908-3917 (2012).

Aslanidi, G V et al., "Optimization of the capsid of recombinant adeno-associated virus 2 (AAV2) vectors: the final threshold?" *PloS One*, 8:e59142 (2013).

Asuri, P et al., "Directed evolution of adeno-associated virus for enhanced gene delivery and gene targeting in human pluripotent stem cells," *Mol. Ther. J. Am. Soc. Gene Ther.*, 20:329-338 (2012).

Bowles, D E et al., "Phase 1 gene therapy for Duchenne muscular dystrophy using a translational optimized AAV vector," *Mol. Ther.*, 20:443-455 (2011).

Cao, O et al., "Impact of the underlying mutation and the route of vector administration on immune responses to factor IX in gene therapy for hemophilia B," *Mol. Ther. J. Am. Soc. Gene Ther.*, 17:1733-1742 (2009).

Coco, W M et al., "Growth factor engineering by degenerate homoduplex gene family recombination," *Nat. Biotechnol.*, 20:1246-1250 (2002).

Cost, G and Cozzarelli, N, "Directed assembly of DNA molecules via simultaneous ligation and digestion," *BioTechniques*, 42:84-89 (2007).

Dalkara, D et al., "In vivo-directed evolution of a new adeno-associated virus for therapeutic outer retinal gene delivery from the vitreous," *Sci. Transl. Med.*, 5:189ra76 (2013).

DiMattia, M et al., "Production, purification, crystallization and preliminary X-ray structural studies of adeno-associated virus serotype 5," *Acta Crystallograph. Sect. F Struct. Biol. Cryst. Commun.*, 61:917-921 (2005).

DiMattia, M A et al., "Structural insight into the unique properties of adeno-associated virus serotype 9," *J. Virol.*, 86:6947-6958 (2012).

DiPrimio, N et al., "Surface loop dynamics in adeno-associated virus capsid assembly,"*J. Virol.*, 82:5178-5189 (2008).

Gabriel, N et al., "Bioengineering of AAV2 capsid at specific serine, threonine, or lysine residues improves its transduction efficiency in vitro and in vivo," *Hum. Gene Ther. Methods.* 24:80-93 (2013).

Gao, G P et al., "Novel adeno-associated viruses from rhesus monkeys as vectors for human gene therapy," *Proc. Nat'l. Acad. Sci. USA*, 99:11854-11859 (2002).

Gibson, D G et al., "Enzymatic assembly of DNA molecules up to several hundred kilobases," *Nat. Methods*, 6:343-345 (2009).

Govindasamy, L et al., "Structural insights into adeno-associated virus serotype 5," *J. Virol.* 87:11187-11199 (2013).

Govindasamy, L, et al., "Structurally mapping the diverse phenotype of adeno-associated virus serotype 4,". *J. Virol.*, 80(23): 11556-11570 (2006).

Granoff and Webster, *Encyclopedia of Virology*, 2nd edition, Academic Press: San Diego, Calif. (1999).

Gray, S J et al., "Directed evolution of a novel adeno-associated virus (AAV) vector that crosses the seizure-compromised blood-brain barrier (BBB)," *Mol. Ther. J. Am. Soc. Gene Ther.*, 18:570-578 (2010).

Gurda, B L et al., "Capsid antibodies to different adeno-associated virus serotypes bind common regions," *J. Virol.*, 87:9111-9124 (2013).

Hauck, B et al., "Generation and characterization of chimeric recombinant AAV vectors," *Mol. Ther.*, 7:419-425 (2003).

Horton, R M et al., "Engineering hybrid genes without the use of restriction enzymes: gene splicing by overlap extension," *Gene*, 77:61-68 (1989).

Hurlbut, G D et al., "Preexisting immunity and low expression in primates highlight translational challenges for liver-directed AAV8-mediated gene therapy," *Mol. Ther.*, 18:1983-1994 (2010).

Jang, J-H et al., "An evolved adeno-associated viral variant enhances gene delivery and gene targeting in neural stem cells," *Mol. Ther. J. Am. Soc. Gene Ther.*, 19:667-675 (2011).

Jeune, V L et al., "Pre-existing anti-adeno-associated virus antibodies as a challenge in AAV gene therapy," *Hum. Gene Ther. Methods*, 24(2):59-67 (2013).

Kaludov, N et al., "Production, purification and preliminary X-ray crystallographic studies of adeno-associated virus serotype 4," *Virology*, 306:1-6 (2003).

Koerber, J T et al., "DNA shuffling of adeno-associated virus yields functionally diverse viral progeny," *Mol. Ther. J. Am. Soc. Gene Ther.*, 16:1703-1709 (2008).

Koerber, J T et al., "Molecular evolution of adeno-associated virus for enhanced glial gene delivery," *Mol. Ther. J. Am. Soc. Gene Ther.*, 17:2088-2095 (2009).

Kwon, I, and Schaffer, D V, "Designer gene delivery vectors: molecular engineering and evolution of adeno-associated viral vectors for enhanced gene transfer," *Pharm. Res.*, 25:489-499 (2008).

Lane, M D et al., "Production, purification, crystallization and preliminary X-ray analysis of adeno-associated virus serotype 8," *Acta Crystallograph. Sect. F Struct. Biol. Cryst. Commun.*, 61:558-561 (2005).

Lewin, A, *Genes V*, Oxford University Press: New York, N.Y. (1994).

Li, C et al., "Single amino acid modification of adeno-associated virus capsid changes transduction and humoral immune profiles," *J. Virol.*, 86:7752-7759 (2012).

Li, J et al., "Role for highly regulated rep gene expression in adeno-associated virus vector production," *J. Virol.*, 71:5236-5243 (1997).

Li, W et al., "Engineering and selection of shuffled AAV genomes: a new strategy for producing targeted biological nanoparticles," *Mol. Ther. J. Am. Soc. Gene Ther.*, 16:1252-1260 (2008).

Li, W et al., "Generation of novel AAV variants by directed evolution for improved CFTR delivery to human ciliated airway epithelium," *Mol. Ther. J. Am. Soc. Gene Ther.*, 17:2067-2077 (2009).

Lochrie, M A et al., "Mutations on the external surfaces of adeno-associated virus type 2 capsids that affect transduction and neutralization," *J. Virol.*, 80:821-834 (2005).

Louis Jeune, V et al., "Pre-existing anti-adeno-associated virus antibodies as a challenge in AAV gene therapy," *Hunm. Gene Ther. Methods*, 24:59-67 (2013).

Maguire, C A et al., "Directed evolution of adeno-associated virus for glioma cell transduction. *J. Neurooncol.* 96:337-347 (2010).

Maheshri, N et al., "Directed evolution of adeno-associated virus yields enhanced gene delivery vectors," *Nat. Biotechnol.*, 24:198-204 (2006).

Manno, C S et al., "Successful transduction of liver in hemophilia by AAV-Factor IX and limitations imposed by the host immune response," *Nat. Med.*, 12:342-347 (2006).

Michelfelder, S et al., "Vectors selected from adeno-associated viral display peptide libraries for leukemia cell-targeted cytotoxic gene therapy," *Exp. Hematol.*, 35:1766-1776 (2007).

Miller, E B et al., "Production, purification and preliminary X-ray crystallographic studies of adeno-associated virus serotype 1," *Acta Crystallograph. Sect. F Struct. Biol. Cryst. Commun.*, 62:1271-1274 (2006).

Mingozzi, F et al., "Induction of immune tolerance to coagulation factor IX antigen by in vivo hepatic gene transfer," *J. Clin. Invest.*, 111:1347-1356 (2003).

Mitchell, M et al., "Production, purification and preliminary X-ray crystallographic studies of adeno-associated virus serotype 9," *Acta Crystallograph. Sect. F Struct. Biol. Cryst. Commun.*, 65:715-718 (2009).

Müller, O J et al., "Random peptide libraries displayed on adeno-associated virus to select for targeted gene therapy vectors," *Nat. Biotechnol.*, 21:1040-1046 (2003).

Muzyezka, N, and Berns, K I, in *Fields Virol. 4th Edn* 2327-2359 (Lippincott Williams & Wilkins) (2001).

Nakai, H et al., "Unrestricted hepatocyte transduction with adeno-associated virus serotype 8 vectors in mice," *J. Virol.*, 79:214-224 (2004).

Nam, H-J et al., "Structure of adeno-associated virus serotype 8, a gene therapy vector. *J. Virol.* 81:12260-12271 (2007).

Naumer, M et al., "Properties of the adeno-associated virus assembly-activating protein," *J. Virol.* 86:13038-13048 (2012).

Ng, R et al., "Structural characterization of the dual glycan binding adeno-associated virus serotype 6," *J. Virol.*, 84:12945-12957 (2010).

Opie, S R et al., "Identification of amino acid residues in the capsid proteins of adeno-associated virus type 2 that contribute to heparan sulfate proteoglycan binding," *J. Virol.*, 77(12):6995-7006 (2003).

Padron, E et al., "Structure of adeno-associated virus type 4," *J. Virol.*, 79:5047-5058 (2005).

Pandya, J et al., "Rationally designed capsid and transgene cassette of AAV6 vectors for dendritic cell-based cancer immunotherapy," *Immunol. Cell Biol.*, 92:116-123 (2014).

Perabo, L et al., "In vitro selection of viral vectors with modified tropism: the adeno-associated virus display," *Mol. Ther J. Am. Soc. Gene Ther.*, 8:151-157 (2003).

Pulicherla, N et al., "Engineering liver-detargeted AAV9 vectors for cardiac and musculoskeletal gene transfer," *Mol. Ther.*, 19:1070-1078 (2011).

Quesada, O et al., "Production, purification and preliminary X-ray crystallographic studies of adeno-associated virus serotype 7," *Acta Crystallograph. Sect. F Struct. Biol. Cryst. Commun.*, 63:1073-1076 (2007).

Rieger et al., *Glossary of Genetics: Classical and Molecular*, 5th edition, *Springer-Verlag*: New York, N.Y. (1991).

Samulski, R J et al., "A recombinant plasmid from which an infectious adeno-associated virus genome can be excised in vitro and its use to study viral replication," *J. Virol.*, 61:3096-3101 (1987).

Sands, M S, "AAV-mediated liver-directed gene therapy," *Methods Mol Biol* 807:141-57 (2011).

Sen, D et al., "Targeted modifications in adeno-associated virus serotype 8 capsid improves its hepatic gene transfer efficiency in vivo," *Hum. Gene Ther. Methods*, 24:104-116 (2013).

Shannon, C E "The mathematical theory of communication," *Bell Syst. Tech. J.*, 27:379-423, 623-656 (1948).

Sharland, A et al., "Liver-directed gene expression using recombinant AAV 2/8 vectors—a tolerogenic strategy for gene delivery?" *Discov. Med.*, 9:519-27 (2010).

Sharma et al., "2A peptides provide distinct solutions to driving stop-carry on translational recoding," *Nucleic Acids Res.*, 40:3143-3151 (2012).

Shen, X et al., "Characterization of the relationship of AAV capsid domain swapping to liver transduction efficiency," *Mol. Ther.*, 15:1955-1962 (2007).

Singleton and Sainsbury, *Dictionary of Microbiology and Molecular Biology*, 3rd edition, John Wiley & Sons: New York, N.Y. (2002).

Sonntag, F et al., "A viral assembly factor promotes AAV2 capsid formation in the nucleolus," *Proc. Nat'l. Acad. Sci. USA*, 107:10220-10225 (2010).

Stachler, M D and Bartlett, J S, "Mosaic vectors comprised of modified AAV1 capsid proteins for efficient vector purification and targeting to vascular endothelial cells," *Gene Ther.*, 13:926-931 (2006).

Summerford, C, and Samulski, R J, "Membrane-associated heparan sulfate proteoglycan is a receptor for adeno-associated virus type 2 virions," *J. Virol.*, 72:1438-1445 (1998).

Tidona and Darai, *The Springer Index of Viruses*, 1st edition, Springer-Verlag: New York, N.Y. (2002).

Walters, R W et al. "Structure of adeno-associated virus serotype 5," *J. Virol.*, 78:3361-3371 (2004).

Wu, P et al., "Mutational analysis of the adeno-associated virus type 2 (AAV2) capsid gene and construction of AAV2 vectors with altered tropism," *J. Virol.* 74:8635-8647 (2000).

Wu, P et al., Mutational analysis of the adeno-associated virus type 2 (AAV2) capsid gene and construction of AAV2 vectors with altered tropism," *J. Virol.*, 74:8635-8647 (2000).

Wu, Z et al., "Adeno-associated virus serotypes: vector toolkit for human gene therapy," *Mol. Ther. J. Am. Soc. Gene Ther.*, 14:316-327 (2006).

Xie, Q et al., "The atomic structure of adeno-associated virus (AAV-2), a vector for human gene therapy," *Proc. Nat'l. Acad. Sci. USA*, 99:10405-10410 (2002).

Yang, L and Xiao, X, "Creation of a cardiotropic adeno-associated virus: the story of viral directed evolution," *Virol. J.*, 10:50 (2013).

Yang, L. et al., "A myocardium tropic adeno-associated virus (AAV) evolved by DNA shuffling and in vivo selection," *Proc. Nat'l. Acad. Sci. USA*, 106:3946-3951 (2009).

Yang, L et al., "Directed evolution of adeno-associated virus (AAV) as vector for muscle gene therapy," *Methods Mol. Biol.* (Clifton, N.J.), 709:127-139 (2011).

Zhong, L et al., "Next generation of adeno-associated virus 2 vectors: point mutations in tyrosines lead to high-efficiency transduction at lower doses," *Proc. Nat'l. Acad. Sci. USA*, 105:7827-7832 (2008).

Zolotukhin, S et al., "Recombinant adeno-associated virus purification using novel methods improves infectious titer and yield," *Gene Ther.*, 6:973-985 (1999). Gigout, L et al., "Altering AAV tropism with mosaic viral capsids," *Mol. Ther.*, 11:856-865 (2005).

It should be understood that the examples and embodiments described herein are for illustrative purposes only and that various modifications or changes in light thereof will be suggested to persons skilled in the art and are to be included within the spirit and purview of this application and the scope of the appended claims.

All references cited herein (including publications, patent applications and patents) are hereby incorporated by reference to the same extent as if each reference was individually and specifically indicated to be incorporated by reference and was set forth in its entirety herein.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order, unless otherwise indicated herein, or otherwise clearly contradicted by context.

The use of any and all examples, or exemplary language (e.g., "such as") provided herein, is intended merely to better illustrate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically and/or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A composition comprising a modified AAV2 capsid protein, wherein the protein comprises SEQ ID NO: 176, SEQ ID NO: 177, or SEQ ID NO: 179.

2. A pharmaceutical formulation comprising the composition of claim 1, further comprising one or more pharmaceutically acceptable carriers, buffers, diluents or excipients.

3. A nucleic acid vector comprising a nucleic acid segment that encodes a modified AAV2 capsid protein comprising SEQ ID NO: 176, SEQ ID NO: 177, or SEQ ID NO: 179.

4. The nucleic acid vector of claim 3, wherein the nucleic acid segment is incorporated into a host cell.

5. The nucleic acid vector of claim 4, wherein the host cell is a mammalian cell.

6. A pharmaceutical formulation comprising the host cell of claim 4, further comprising one or more pharmaceutically acceptable carriers, buffers, diluents or excipients.

7. An rAAV virion comprising a modified AAV2 capsid protein and a nucleic acid segment that encodes one or more diagnostic, therapeutic, and/or prophylactic agents, wherein the protein comprises SEQ ID NO: 176, SEQ ID NO: 177, or SEQ ID NO: 179.

8. The rAAV virion of claim 7, wherein the nucleic acid segment further comprises an enhancer, a post-transcriptional regulatory sequence, a polyadenylation signal, or any combination thereof, operably linked to the nucleic acid segment.

9. The rAAV virion of claim 7, wherein the therapeutic agent is a polypeptide, a peptide, a ribozyme, a peptide nucleic acid, an siRNA, an RNAi, an antisense oligonucleotide, an antisense polynucleotide, an antibody, an antigen binding fragment, or any combination thereof.

10. The rAAV virion of claim 7, wherein the therapeutic agent is an agonist, an antagonist, an anti-apoptosis factor, an inhibitor, a receptor, a cytokine, a cytotoxin, an erythropoietic agent, a glycoprotein, a growth factor, a growth factor receptor, a hormone, a hormone receptor, an interferon, an interleukin, an interleukin receptor, a nerve growth factor, a neuroactive peptide, a neuroactive peptide receptor, a protease, a protease inhibitor, a protein decarboxylase, a protein kinase, a protein kinase inhibitor, an enzyme, a receptor binding protein, a transport protein or an inhibitor thereof, a serotonin receptor or an uptake inhibitor thereof, a serpin, a serpin receptor, a tumor suppressor, a chemotherapeutic, or any combination thereof.

11. A pharmaceutical formulation comprising the rAAV virion of claim 7, further comprising one or more pharmaceutically acceptable carriers, buffers, diluents or excipients.

12. A method of administering a therapeutically effective amount of the rAAV virion of claim 7 to a subject in need thereof.

13. A composition comprising a modified AAV2 capsid protein having a sequence consisting of the following amino acid substitutions: S492D, A493G, D494E, E499D, and Y500F in a naturally-occurring AAV2 capsid sequence.

14. A nucleic acid vector comprising a nucleic acid segment that encodes a modified AAV2 capsid protein in accordance with claim 13.

15. The nucleic acid vector of claim 14, wherein the nucleic acid segment is incorporated into a host cell.

16. A pharmaceutical formulation comprising the host cell of claim 15, further comprising one or more pharmaceutically acceptable carriers, buffers, diluents or excipients.

17. The nucleic acid vector of claim 16, wherein the host cell is a mammalian cell.

18. An rAAV virion comprising a modified AAV2 capsid protein in accordance with claim 13 and a nucleic acid segment that encodes one or more diagnostic, therapeutic, and/or prophylactic agents.

19. The rAAV virion of claim 18, wherein the nucleic acid segment further comprises an enhancer, a post-transcriptional regulatory sequence, a polyadenylation signal, or any combination thereof, operably linked to the nucleic acid segment.

20. The rAAV virion of claim 18, wherein the therapeutic agent is a polypeptide, a peptide, a ribozyme, a peptide nucleic acid, an siRNA, an RNAi, an antisense oligonucleotide, an antisense polynucleotide, an antibody, an antigen binding fragment, or any combination thereof.

21. The rAAV virion of claim 18, wherein the therapeutic agent is an agonist, an antagonist, an anti-apoptosis factor, an inhibitor, a receptor, a cytokine, a cytotoxin, an erythropoietic agent, a glycoprotein, a growth factor, a growth factor receptor, a hormone, a hormone receptor, an interferon, an interleukin, an interleukin receptor, a nerve growth factor, a neuroactive peptide, a neuroactive peptide receptor, a protease, a protease inhibitor, a protein decarboxylase, a protein kinase, a protein kinase inhibitor, an enzyme, a receptor binding protein, a transport protein or an inhibitor thereof, a serotonin receptor or an uptake inhibitor thereof, a serpin, a serpin receptor, a tumor suppressor, a chemotherapeutic, or any combination thereof.

22. A pharmaceutical formulation comprising the rAAV virion of claim 18, further comprising one or more pharmaceutically acceptable carriers, buffers, diluents or excipients.

23. A method of administering a therapeutically effective amount of the rAAV virion of claim 18 to a subject in need thereof.

\* \* \* \* \*